(12) United States Patent
Guzzo et al.

(10) Patent No.: US 9,096,546 B2
(45) Date of Patent: Aug. 4, 2015

(54) ARYL- AND HETEROARYL-SUBSTITUTED TETRAHYDROBENZO-1,4-DIAZEPINES AND USE THEREOF TO BLOCK REUPTAKE OF NOREPINEPHRINE, DOPAMINE, AND SEROTONIN

(75) Inventors: Peter R. Guzzo, Niskayuna, NY (US); Bruce F. Molino, Slingerlands, NY (US); Wenge Cui, Clifton Park, NY (US); Shuang Liu, Schenectady, NY (US); Richard E. Olson, Orange, CT (US); Larry Yet, Mobile, AL (US)

(73) Assignees: Albany Molecular Research, Inc., Albany, NY (US); Bristol-Myers Squibb Company, Princeton, NJ (US)

( * ) Notice: Subject to any disclaimer, the term of this patent is extended or adjusted under 35 U.S.C. 154(b) by 356 days.

(21) Appl. No.: 12/598,882

(22) PCT Filed: May 8, 2008

(86) PCT No.: PCT/US2008/063039
§ 371 (c)(1),
(2), (4) Date: Feb. 3, 2010

(87) PCT Pub. No.: WO2008/141081
PCT Pub. Date: Nov. 20, 2008

(65) Prior Publication Data
US 2010/0137287 A1      Jun. 3, 2010

Related U.S. Application Data

(60) Provisional application No. 60/917,189, filed on May 10, 2007.

(51) Int. Cl.
| | |
|---|---|
| *A61K 31/5513* | (2006.01) |
| *C07D 243/14* | (2006.01) |
| *C07D 401/02* | (2006.01) |
| *C07D 403/02* | (2006.01) |
| *C07D 401/04* | (2006.01) |
| *C07D 403/04* | (2006.01) |
| *C07D 403/12* | (2006.01) |
| *C07D 405/14* | (2006.01) |
| *C07D 471/04* | (2006.01) |

(52) U.S. Cl.
CPC ............ *C07D 243/14* (2013.01); *C07D 401/04* (2013.01); *C07D 403/04* (2013.01); *C07D 403/12* (2013.01); *C07D 405/14* (2013.01); *C07D 471/04* (2013.01)

(58) Field of Classification Search
CPC ............ A61K 31/5513; C07D 243/14; C07D 401/02; C07D 403/02
USPC ................... 514/221; 540/569, 573
See application file for complete search history.

(56) References Cited

U.S. PATENT DOCUMENTS

| | | |
|---|---|---|
| 3,144,439 A | 8/1964 | Reeder et al. |
| 3,384,635 A | 5/1968 | Carabateas |
| 3,415,814 A | 12/1968 | Carabateas |
| 3,457,258 A | 7/1969 | Santilli et al. |
| 3,517,061 A | 6/1970 | Santilli et al. |
| 3,523,939 A | 8/1970 | Fryer et al. |
| 3,985,731 A | 10/1976 | Vogt |
| 4,666,913 A | 5/1987 | Kubla et al. |
| 4,820,834 A | 4/1989 | Evans et al. |
| 4,933,445 A | 6/1990 | Pelletier et al. |
| 4,957,915 A | 9/1990 | Kim et al. |
| 4,975,439 A | 12/1990 | Van Daele et al. |
| 5,153,191 A | 10/1992 | Woodruff |
| 5,175,159 A | 12/1992 | Bock et al. |
| 5,206,238 A | 4/1993 | Bock et al. |
| 5,244,898 A | 9/1993 | Ogawa et al. |
| 5,258,510 A | 11/1993 | Ogawa et al. |
| 5,498,609 A | 3/1996 | Ogawa et al. |
| 5,550,126 A | 8/1996 | Horwell et al. |
| 5,593,988 A | 1/1997 | Tahara et al. |

(Continued)

FOREIGN PATENT DOCUMENTS

| | | |
|---|---|---|
| BE | 659443 A | 9/1965 |
| CA | 2160092 | 4/1996 |

(Continued)

OTHER PUBLICATIONS

Lehmann et al., Zur Synthese von 1-Aryl-, 1-Aroyl- und 1-Benzyl-2,3,4-5-Tetrahydro-1H-1,4-Benzodiazepinen, Archive Pharmazie, vol. 317, No. 7, pp. 595-606, 1984.*
International Search Report for International Patent Application No. PCT/US08/63039 (Aug. 4, 2008).
Written Opinion for International Patent Application No. PCT/US08/63039 (Aug. 4, 2008).
Examination Report for Australian Application No. 2008251557 dated Nov. 10, 2011.
Office Action for Chinese Application No. 200880024332.6 dated Jul. 5, 2011 (translation).
Decision on Rejection for Chinese Application No. 200880024332.6 dated Apr. 24, 2012 (translation).
Official Action for Eurasian Application No. 200971044/28 dated Jul. 18, 2011 (translation).

(Continued)

*Primary Examiner* — Brenda Coleman
(74) *Attorney, Agent, or Firm* — LeClairRyan, a Professional Corporation

(57) ABSTRACT

The aryl- and heteroaryl-substituted tetrahydrobenzo-1,4-diazepine derivative compounds of the present invention are represented by formulae 1(A-D) having the following structure: where the substituents X and $R^1$-$R^8$ are as defined herein.

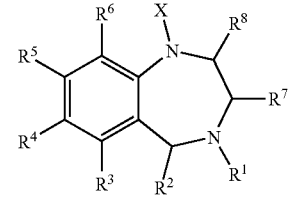

I(A-D)

21 Claims, No Drawings

(56) References Cited

U.S. PATENT DOCUMENTS

| | | | |
|---|---|---|---|
| 5,618,792 A | 4/1997 | Gyorkos et al. |
| 5,618,812 A | 4/1997 | Pineiro et al. |
| 5,674,909 A | 10/1997 | Montanari et al. |
| 5,677,298 A | 10/1997 | Yukimasa et al. |
| 5,681,833 A | 10/1997 | Pineiro et al. |
| 5,770,438 A | 6/1998 | Nakahama et al. |
| 5,852,010 A | 12/1998 | Graham et al. |
| 5,977,132 A | 11/1999 | Suzuki et al. |
| 6,008,214 A | 12/1999 | Kwon et al. |
| 6,011,029 A | 1/2000 | Ding et al. |
| 6,015,789 A | 1/2000 | Suzuki et al. |
| 6,096,735 A | 8/2000 | Ogawa et al. |
| 6,100,254 A | 8/2000 | Budde et al. |
| 6,333,321 B1 | 12/2001 | Scarborough |
| 6,352,982 B1 | 3/2002 | Mabuchi et al. |
| 6,429,205 B1 | 8/2002 | Jacobson et al. |
| 6,455,529 B1 | 9/2002 | Gante et al. |
| 6,458,783 B1 | 10/2002 | Ding et al. |
| 6,476,029 B1 | 11/2002 | Niewoehner et al. |
| 6,482,838 B2 | 11/2002 | Pratt |
| 6,503,901 B1 | 1/2003 | Thompson et al. |
| 6,503,902 B2 | 1/2003 | Olson et al. |
| 6,552,041 B2 | 4/2003 | Lauffer et al. |
| 6,632,812 B2 | 10/2003 | Han et al. |
| 6,649,366 B2 | 11/2003 | Chubinskaya et al. |
| 6,713,476 B2 | 3/2004 | Yang et al. |
| 6,759,404 B2 | 7/2004 | Olson et al. |
| 6,809,092 B2 | 10/2004 | Ohmoto et al. |
| 6,825,191 B2 | 11/2004 | Nakagawa et al. |
| 6,831,080 B2 | 12/2004 | Wu et al. |
| 6,916,805 B2 | 7/2005 | Dudley et al. |
| 6,930,104 B2 | 8/2005 | Kakihana et al. |
| 6,943,159 B1 | 9/2005 | Gouliaev et al. |
| 7,001,901 B2 | 2/2006 | Yang |
| 7,067,512 B2 | 6/2006 | Lu et al. |
| 7,074,781 B2 | 7/2006 | Ashworth et al. |
| 7,074,783 B2 | 7/2006 | Holcomb et al. |
| 7,081,453 B2 | 7/2006 | Van Emelen et al. |
| 7,105,509 B2 | 9/2006 | Pineiro et al. |
| 7,109,341 B2 | 9/2006 | Horwitz et al. |
| 7,176,195 B2 | 2/2007 | Ashworth et al. |
| 7,192,950 B2 | 3/2007 | Aissaoui et al. |
| 7,196,079 B2 | 3/2007 | Burgey et al. |
| 7,220,739 B2 | 5/2007 | Glick |
| 7,238,685 B2 | 7/2007 | Bolli et al. |
| 7,250,410 B2 | 7/2007 | Bourguignon et al. |
| 7,279,468 B2 | 10/2007 | Geneste et al. |
| 7,323,455 B2 | 1/2008 | Zhang et al. |
| 7,476,665 B2 | 1/2009 | Burgey et al. |
| 7,763,605 B2 | 7/2010 | Matthews et al. |
| 2002/0022636 A1 | 2/2002 | Li et al. |
| 2002/0032262 A1 | 3/2002 | Zhang et al. |
| 2002/0128208 A1 | 9/2002 | Snyder et al. |
| 2003/0134846 A1 | 7/2003 | Windsor et al. |
| 2004/0009972 A1 | 1/2004 | Ding et al. |
| 2004/0063750 A1 | 4/2004 | Nishimoto et al. |
| 2004/0192732 A1 | 9/2004 | Pratt et al. |
| 2004/0235753 A1 | 11/2004 | Pitt et al. |
| 2005/0272722 A1 | 12/2005 | Lansbury et al. |
| 2005/0272723 A1 | 12/2005 | Glick |
| 2006/0018839 A1 | 1/2006 | Ieni et al. |
| 2006/0052369 A1 | 3/2006 | Glick |
| 2006/0069086 A1 | 3/2006 | Michalow |
| 2006/0079495 A1 | 4/2006 | Blum |
| 2006/0135507 A1 | 6/2006 | Yokoyama et al. |
| 2006/0148790 A1 | 7/2006 | Burgey et al. |
| 2007/0099938 A1 | 5/2007 | Ohmoto et al. |

FOREIGN PATENT DOCUMENTS

| | | |
|---|---|---|
| DE | 21 65 310 A1 | 7/1973 |
| EP | 411751 A1 | 2/1991 |
| EP | 705607 A2 | 4/1996 |
| GB | 1 173 540 A | 12/1969 |
| GB | 2259013 A1 | 3/1993 |
| JP | 02169569 A2 | 6/1990 |
| JP | 06016643 A2 | 1/1994 |
| JP | 09087260 A2 | 3/1997 |
| JP | 09221476 A2 | 8/1997 |
| WO | 9401113 A1 | 1/1994 |
| WO | 9633723 A2 | 10/1996 |
| WO | 9723202 A1 | 7/1997 |
| WO | 9724119 A1 | 7/1997 |
| WO | 9736879 A1 | 10/1997 |
| WO | 9915524 A1 | 4/1999 |
| WO | 9918951 A1 | 4/1999 |
| WO | 0012547 A2 | 3/2000 |
| WO | 0038618 A2 | 7/2000 |
| WO | 01/10846 A2 | 2/2001 |
| WO | 0119797 A2 | 3/2001 |
| WO | 0140215 A1 | 6/2001 |
| WO | 0155121 A1 | 8/2001 |
| WO | 02051232 A2 | 7/2002 |
| WO | 02080895 A2 | 10/2002 |
| WO | 03002147 A1 | 1/2003 |
| WO | 03024456 A1 | 3/2003 |
| WO | 03092606 A2 | 11/2003 |
| WO | 03095625 A2 | 11/2003 |
| WO | 2004067008 A1 | 8/2004 |
| WO | 2004091628 A1 | 10/2004 |
| WO | 2004106310 A1 | 12/2004 |
| WO | 2005087226 A1 | 9/2005 |
| WO | 2006/009734 A1 | 1/2006 |
| WO | 2006004201 A1 | 1/2006 |
| WO | 2006018443 A1 | 2/2006 |
| WO | 2006021213 A2 | 3/2006 |
| WO | 2007011820 A2 | 1/2007 |
| WO | 2009145357 A1 | 12/2009 |

OTHER PUBLICATIONS

Official Action for Eurasian Application No. 200971044/28 dated Feb. 2, 2012 (translation).

Examination Report for New Zealand Application No. 580801 dated Oct. 15, 2010.

Examination Report for New Zealand Application No. 580801 dated Apr. 12, 2012.

Examination Report for Singapore Application No. 200907253-9 dated Aug. 25, 2011.

Examination Report for Israeli Application No. 201922 dated Jun. 12, 2012 (translation)(redacted).

Office Action for European Application No. 08780604.8 dated Nov. 21, 2012.

Examination Report for Singapore Application No. 200907253-9 dated Dec. 17, 2010.

Office Action for Colombian Application 09 139.244 dated Oct. 12, 2012 (translation).

Office Action for Colombian Application 09 139.244 dated Mar. 14, 2013 (translation).

Office Action for Mexican Application MA/a/2009/011923 dated May 28, 2013 (translation).

Notice of Reasons for Rejection for Japanese Application 2010-507653 dated Jun. 6, 2013 (translation).

Translation of Notice of Reexamination for Chinese Patent Application No. 200880024332.6 (Jul. 29, 2013).

Office Action for Canadian Patent Application No. 2,685,860 (Jan. 27, 2014).

Translation of Notice of Defects for Israeli Patent Application No. 210922 (Dec. 10, 2013).

Hino et al., "Agents Acting on the Central Nervous System. Synthesis of 3-Phenyl-2-piperazinyl-1-benzazocines, 3-Substituted-2-piperazinyl-1-benzazepines and Related Compounds," Chem. Pharm. Bull. 36(7):2386-2400 (1988).

Bolli et al., "Novel Benzo [1,4] diazepin-2-one Derivatives as Endothelin Receptor Antagonists," J. Med. Chem. 47(11):2776-2795 (2004).

Ding et al., "Discovery and Structure-Activity Relationships of Imidazole-Containing Tetrahydrobenzodiazepine Inhibitors of Farnesyltransferase," J. Med. Chem. 42(25):5241-5253 (1999).

(56) References Cited

OTHER PUBLICATIONS

Matsuhisa et al., "Nonpeptide Arginine Vasopressin Antagonists for Both V1A and V2 Receptors: Synthesis and Pharmacological Properties of 2-Phenyl-4'-(2,3,4,5-tetrahydro-1H-1,5-benzodiazepine-1-carbonyl)benzanilide Derivatives," Chem. and Pharm. Bulletin 46(10):1566-1579 (1998).

Raza et al., "Structure and Relative Stability of Dirhodium Tetracamphanate Adducts with 5-pyrido-1,4-benzodiazepines and their 4,5-dihydro Congeners; First Representatives of Non-Symmetric Bidentate 1,4-bisnitrogen Ligands," Croatica Chemica Acta 69(1):241-259 (1996).

Kukla et al., "Synthesis and Anti-HIV-1 Activity of 4,5,6,7-tetrahydro-5-methylimidazo [4,5,1-jk] [1,4] benzodiazepin-2 (1H)-one (TIBO) Derivatives," J. Med. Chem. 34(11):3187-97 (1991).

Lehmann et al., "Amphiphilic Compounds, I. Synthesis of 1-aryl-1-aroyl- and 1-benzyl-2,3,4,5-tetrahydro-1H-1,4-benzodiazepines," Archiv der Pharmazie (Weinheim, Germany) 317(7):595-606 (1984).

Moitessier et al., "Combining Pharmacophore Search, Automated Docking, and Molecular Dynamics Simulations as a Novel Strategy for Flexible Docking. Proof of Concept: Docking of Arginine-Glycine-Aspartic Acid-like Compounds into the alpha v beta 3 Binding Site," J. Med. Chem. 47(17):4178-4187 (2004).

Im et al., "Solid-Phase Synthesis of Tetrahydro-1,4-benzodiazepin-2-one Derivatives as a Beta-Turn Peptidomimetic Library," J. Combinatorial Chem. 6(2):207-213 (2004).

Carabateas et al., "Analgesic Antagonists. I. 4-Substituted 1-acyl-2,3,4,5-tetrahydro-1H-1,4-benzodiazepines," J. Med. Chem. 9(1):6-10 (1966).

Klaic et al., "NMR Spectroscopic Study of Camphanic Acid, Rh2 [camphanate]4, and its Adducts with 1,4-benzodiazepines," Spectroscopy Letters 28(5):683-697 (1995).

Vinkovic et al., "13C NMR and IR Evidence for the Two Types of Copper(I) and (II) Complexes with 5-pyrido-1,4-benzodiazepin-2-ones," Spectroscopy Letters 27(2):269-279 (1994).

Gatta et al., "Synthesis of 1,4-benzodiazepines and 1,5-benzodiazocines by Oxidative Fission of the Double Bonds in Indole Derivatives," Farmaco, Edizione Scientifica 32(1):33-39 (1977).

Misiti et al., "1,2,3,5-Tetrahydro-4H-1,5-benzodiazepin-4-ones and 1,2,3,4-tetrahydro-5H-1,4-benzodiazepin-5-ones from the Reaction of Hydrozoic Acid on 1,2,3,4-tetrahydroquinolin-4-one-5," J. Heterocyclic Chemistry 8(2):231-236 (1971).

Santilli et al., "5H-1, 4-Benzodiazepin-5-ones from Substituted O-Aminobenzamides," J. Organic Chem. 31(12):4268-4271 (1966).

Ichii, "Phenothiazine Derivatives. V. Beckmann Rearrangement and Schmidt Reaction of 3H-pyrido-[3,2,1-kl] phenothiazin-3-one derivatives," Yakugaku Zasshi 82:999-1004 (1962).

Hunt et al., "Discovery of (R)-7-Cyano-2,3,4,5-tetrahydro-1-(1H-imidazol-4-ylmethyl)-3-(phenylmethyl)-4-(2-thienylsulfonyl)-1H-1, 4-benzodiazepine (BMS-214662), a Farnesyltransferase Inhibitor with Potent Preclinical Antitumor Activity," J. Med. Chem. 43(20):3587-3595 (2000).

CAS Registry Compound 865528-28-5 (Oct. 18, 2005).
CAS Registry Compound 794458-70-1 (Dec. 8, 2004).
CAS Registry Compound 791555-35-6 (Dec. 2, 2004).
CAS Registry Compound 787485-28-3 (Nov. 23, 2004).
CAS Registry Compound 782418-93-3 (Nov. 16, 2004).
CAS Registry Compound 780738-13-8 (Nov. 15, 2004).
CAS Registry Compound 777823-01-5 (Nov. 10, 2004).
CAS Registry Compound 775515-11-2 (Nov. 7, 2004).
CAS Registry Compound 774118-24-0 (Nov. 2, 2004).
CAS Registry Compound 768341-61-3 (Oct. 24, 2004).
CAS Registry Compound 767256-43-9 (Oct. 22, 2004).
CAS Registry Compound 766489-87-6 (Oct. 21, 2004).
CAS Registry Compound 761336-68-9 (Oct. 12, 2004).
CAS Registry Compound 755722-64-6 (Oct. 1, 2004).
CAS Registry Compound 755710-21-5 (Oct. 1, 2004).
CAS Registry Compound 753406-58-5 (Sep. 28, 2004).
CAS Registry Compound 749143-96-2 (Sep. 21, 2004).
CAS Registry Compound 742034-39-5 (Sep. 10, 2004).
CAS Registry Compound 737691-49-5 (Sep. 2, 2004).
CAS Registry Compound 736866-52-7 (Sep. 1, 2004).
CAS Registry Compound 732923-90-9 (Aug. 25, 2004).
CAS Registry Compound 715653-61-5 (Jul. 23, 2004).
CAS Registry Compound 703400-15-1 (Jul. 2, 2004).
CAS Registry Compound 694424-78-7 (Jun. 16, 2004).
CAS Registry Compound 687627-75-4 (May 31, 2004).
CAS Registry Compound 687601-24-7 (May 30, 2004).
CAS Registry Compound 19005-14-2 (Nov. 16, 1984).

Communication and Supplementary European Search Report for EP 08780604.8 (Jul. 6, 2011).

Examination Report for New Zealand Application No. 580801 (Aug. 24, 2011).

Written Opinion for Singapore Application No. 200907253-7 (Dec. 17, 2010).

* cited by examiner

ARYL- AND HETEROARYL-SUBSTITUTED TETRAHYDROBENZO-1,4-DIAZEPINES AND USE THEREOF TO BLOCK REUPTAKE OF NOREPINEPHRINE, DOPAMINE, AND SEROTONIN

This application claims the benefit of U.S. Provisional Patent Application Ser. No. 60/917,189, filed May 10, 2007, which is hereby incorporated by reference in its entirety.

FIELD OF THE INVENTION

The present invention relates to compounds, compositions, methods for the treatment of various neurological and psychological disorders, and the use of the compounds in combination therapy. In particular, the present invention relates to such compounds, compositions, and methods, where the compounds are novel aryl- and heteroaryl-substituted tetrahydrobenzo-1,4-diazepine derivatives.

BACKGROUND OF THE INVENTION

It is well known that the neurotransmitters, dopamine (DA), norepinephrine (NE), and serotonin (5-HT), regulate a number of biological processes and that decreased levels of DA, NE, and 5-HT are associated with a number of neurological disorders and their physical manifestations. Significant effort has been expended on devising methods for adjusting the levels of these neurotransmitters in order to produce a desired pharmacological effect. Preventing the reuptake of these neurotransmitters in any combination of one, two, or all three of them is likely to be effective in treating these disorders. Targeting the dopamine transporter (DAT), norepinephrine transporter (NET), and the serotonin transporter (SERT) proteins has proven to be an effective way of increasing the levels of the respective monoamines.

Methylphenidate, currently used for the treatment of attention deficit-hyperactivity disorder, is known to be selective for inhibition of the DAT. Also, U.S. Pat. No. 5,444,070 discloses selective inhibitors of the dopamine reuptake as treatments for Parkinson's disease, drug addiction or abuse including cocaine and amphetamines.

Selective norepinephrine reuptake inhibitors (NARI) have also been disclosed. U.S. Pat. No. 6,352,986 describes methods of treating attention deficit-hyperactivity disorder (ADHD), addictive disorders, and psychoactive substance use disorders with Reboxetine. Also, Atomoxetine (STRATTERA®) is currently marketed as a selective NET reuptake inhibitor for ADHD.

The use of selective serotonin reuptake inhibitors (SSRI) has been shown to be effective in treating depressive disorders. Sertraline, Citalopram, and Paroxetine are well known examples of SSRIs used to treat disorders, such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy.

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1D antagonist for the treatment of a wide variety of conditions.

Also advantageous is the use of compounds that inhibit one or more of the neurotransmitters at the same time. The antidepressant qualities of the dual NET and SERT reuptake inhibitor duloxetine is disclosed in European Patent No. EP 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are also disclosed in U.S. Pat. No. 6,136,083 for the treatment of depression. It is also recognized that compounds which inhibit the reuptake of NE, DA, and 5-HT in varying ratios not specifically mentioned here would also be advantageous.

Treating illnesses by inhibiting the reuptake of all three of the monoamines either through combination therapy or "triple inhibitors" may have clinical benefit as well. Rationale for inclusion of a dopamine enhancing component in anti-depressant therapy includes observed deficits in dopaminergic function, the success of combination therapy with dopamine agonists and traditional antidepressants, and an increased sensitivity in dopamine receptors due to chronic anti-depressant administration (Skolnick et al., *Life Sciences,* 73:3175-3179 (2003)). Combination therapy with an SSRI and a noradrenaline and dopamine reuptake inhibitor was shown to be more efficacious in patients with treatment-resistant depression (Lam et al, *J. Clin. Psychiatry,* 65(3):337-340 (2004)). Another study using a combination of a serotonin and norepinephrine reuptake inhibitor with a norepinephrine and dopamine reuptake inhibitor reported a significant decrease in depressive symptoms in patients with refractory major depressive disorder who had failed to respond previously to either agent alone (Papkostas, G. I., *Depression and Anxiety,* 23:178-181 (2006)). In addition, the combination of bupropion-SR with either SSRIs or norepinephrine and dopamine reuptake inhibitors was found to induce less sexual dysfunction than monotherapy (Kennedy et al, *J. Clin. Psychiatry,* 63(3):181-186 (2002)). As such, inhibitory activity against DA reuptake, in addition to NE and 5-HT reuptake, is expected to provide a more rapid onset of anti-depressant effect than other mixed inhibitors which are selective for NET and SERT over DAT. PCT International Publication Nos. WO 03/101453 and WO 97/30997 disclose a class of compounds which are active against all three monoamine transporters. Also, PCT International Publication No. WO 03/049736 discloses a series of 4-substituted piperidines, each of which displays similar activity against DA, NE, and 5-HT transporters. Bicyclo[2.2.1]heptanes (Axford et al., *Bioorg. Med. Chem. Lett.,* 13:3277-3280 (2003)) and azabicyclo[3.1.0] hexanes (Skolnick et al., *Eur. J. Pharm.,* 461:99-104 (2003)) are also described as triple inhibitors of the three monoamine transporters.

Lehman et al., *Archiv der Pharmazie,* 317(7):595-606 (1984) describes compounds of formula (1) as products of cyclization and reduction of 2-[chloroacetyl(phenyl)amino] benzoates. No biological activity of these compounds was reported in the above-mentioned reference.

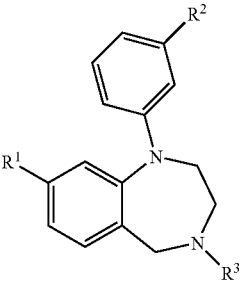

| R¹ | R² | R³ |
|----|-----|-----|
| H  | H   | —CH₂C₆H₅ |
| H  | H   | -n-C₃H₇ |
| Cl | H   | -n-C₃H₇ |
| H  | CF₃ | -n-C₃H₇ |
| H  | H   | H |

Misiti et al., *Journal of Heterocyclic Chemistry*, 8:231-236 (1971) describes the compound of formula (2) as a product of the Schmidt reaction on 1,2,3,4-tetrahydroquinolin-4-ones, followed by reduction. The compound was prepared in order to clarify structural details. No biological activity of this compound was reported in the above-mentioned reference.

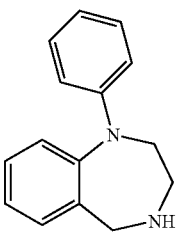

There is still a large need for compounds that block the reuptake of norepinephrine, dopamine, and serotonin and treat various neurological and psychological disorders.

The present invention is directed to achieving this objective.

SUMMARY OF THE INVENTION

The present invention relates to compounds represented by formulae I(A-D) having the following structure:

I(A-D)

where:
X represents a 5- or 6-membered aromatic or non-aromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^9$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^9$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydrobenzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^9$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^1$ and $R^2$ are each independently selected from the group consisting of H, $C_1$-$C_6$ alkyl, $C_2$-$C_6$ alkenyl, $C_2$-$C_6$-alkynyl, $C_3$-$C_6$ cycloalkyl, and $C_4$-$C_7$ cycloalkylalkyl, each of which is optionally substituted from 1 to 3 times with substituents as defined below in $R^{10}$; or $R^2$ is gem-dimethyl;

$R^3$, $R^5$, and $R^6$ are each independently selected from the group consisting of H, halogen, —$OR^{11}$, —$NR^{12}R^{13}$, $S(O)_n R^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^9$;

$R^4$ is H, halogen, —$OR^{11}$, —$NR^{12}R^{13}$, —$S(O)_n R^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; or $R^4$ is phenyl, pyridyl, 2-oxo-pyridin-1(2H)-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted monocyclic or bicyclic aryl or monocyclic or bicyclic heteroaryl and $R^4$ is H, —$OR^{11}$, —$NR^{12}R^{13}$, —$S(O)_nR^{14}$, —$C(O)R^{15}$, —CN, halogen or $C_1$-$C_6$ alkyl, wherein each of the $C_1$-$C_6$ alkyl is optionally substituted from 1 to 3 times with substituents as defined below in $R^{10}$; and provided that for compounds of formula ID, X is substituted monocyclic heteroaryl and $R^4$ is substituted monocyclic or bicyclic aryl or heteroaryl;

$R^7$ and $R^8$ are each independently selected from the group consisting of H, $C_1$-$C_6$ alkyl, $C_2$-$C_6$ alkenyl, $C_2$-$C_6$-alkynyl, $C_3$-$C_6$ cycloalkyl, and $C_4$-$C_7$ cycloalkylalkyl, each of which is optionally substituted from 1 to 3 times with substituents as defined below in $R^{10}$; or $R^2$, $R^7$, and $R^8$ are gem-dimethyl, with the proviso that only one of $R^7$ and $R^8$ is gem-dimethyl;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;

$R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$;

$R^{11}$ is selected from the group consisting of H, $C_1$-$C_4$ alkyl, $C_3$-$C_6$ cycloalkyl, $C_4$-$C_7$ cycloalkylalkyl, and —$C(O)R^{15}$, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{11}$ is selected from the group consisting of phenyl, benzyl, pyridazinyl, pyrimidinyl, pyrazinyl, other 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{12}$ and $R^{13}$ are each independently selected from the group consisting of H, —$C(O)R^{15}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$;

$R^{12}$ and $R^{13}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^9$;

$R^{12}$ and $R^{13}$ are each independently a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —$S(O)_nR^{14}$, and —$C(O)R^{15}$, with the proviso that only one of $R^{12}$ and $R^{13}$ is a bridged bicyclic ring;

$R^{12}$ and $R^{13}$ are taken together with the nitrogen to which they are attached to form a saturated or partially saturated monocyclic or bicyclic heterocycle selected from the group consisting of piperidine, pyrrolidine, morpholine, thiomorpholine, [1,2]oxazinane, isoxazolidine, 2-oxopiperidine, 2-oxopyrrolidine, 3-oxomorpholine, 3-oxothiomorpholine, 5,6,7,8-tetrahydroimidazo[1,2-c]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, —$OR^{11}$, —$NR^{12}R^{13}$, —$S(O)_n R^{14}$, —$C(O)R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in thr ring, where the heterocycle is optionally substituted on a ring carbon with from 1 to 3 times with a substituent selected independently at each occurrence thereof from the group consisting of halogen, cyano, —$OR^{11}$, —$NR^{12}R^{13}$, —$S(O)_nR^{14}$, —$C(O)R^{15}$, and $C_1$-$C_4$ alkyl, or on the additional nitrogen atom from 1 to 3 times with a substituent selected independently at each occurrence thereof from the group consisting of $S(O)_nR^{14}$, —$C(O)R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^9$; or when $R^4$ is —$NR^{12}R^{13}$ or —$C(O)NR^{12}R^{13}$, either $R^{12}$ or $R^{13}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{15}$, and —$S(O)_nR^{14}$, or either $R^{12}$ or $R^{13}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{15}$, and —$S(O)_nR^{14}$;

$R^{14}$ is selected from the group consisting of H, —$NR^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{14}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{15}$ is selected from the group consisting of H, —$OR^{11}$, —$NR^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{15}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

n is 0, 1 or 2;

with the following provisos that (1) when $R^1$ is H or benzyl, X cannot be phenyl; and (2) when $R^1$ is n-propyl, X cannot be phenyl or 3-(trifluoromethyl)phenyl;

or an oxide of, or a pharmaceutically acceptable salt thereof.

Results of recent clinical investigations with drugs, such as duloxetine, venlafaxine, atomoxetine, and others that work mechanistically through transporter reuptake inhibition provide evidence that potency and selectivity are important factors in leading to drugs with an improved efficacy, improved therapeutic index, and utility for treatment of new clinical indications. Duloxetine, a dual action transporter reuptake inhibitor, is a selective inhibitor for serotonin transporter protein and norepinephrine transporter protein reuptake (Sorbera et al., Drugs of the Future, 25(9):907-916 (2000), which is hereby incorporated by reference in its entirety) and has been marketed for the treatment of depression and diabetic peripheral neuropathic pain. In clinical studies, researchers attribute the effect of the medication on a broad spectrum of depression symptoms, which include emotional and painful physical symptoms as well as anxiety, to its dual reuptake inhibition of both serotonin and norepinephrine. Venlafaxine, which is also reported to be a selective serotonin and norepinephrine reuptake inhibitor (SNRI class), has been reported to exhibit a more rapid onset of action. The late onset of action has been a drawback with the first generation antidepressants, i.e., the single action serotonin selective reuptake inhibitors (SSRI class). For example, PROZAC®, the prototype drug in this class, can take four weeks or longer for full anti-depressive activity to take effect.

Atomoxetine (STRATTERA®), a norepinephrine selective transporter reuptake inhibitor, has been marketed for the treatment of ADHD. Unlike RITALIN®, one of the most frequently used drugs for treatment of ADHD, atomoxetine has little or no activity at the dopamine transporter. As a result, atomoxetine has the advantage that it is not scheduled as a controlled substance because it has minimal potential for substance abuse.

In a manner similar to the newer clinical agents like atomoxetine, duloxetine, and venlafaxine, the compounds of the present invention may exhibit improved efficacy towards broader symptoms of depression. The compounds of the present invention may also exhibit more rapid onset of action in the treatment of central nervous system (CNS) diseases, such as depression. In addition to providing improved efficacy, the compounds of the present invention may also exhibit fewer undesirable side effects. Finally, because the compounds of the present invention possess a diverse transporter reuptake inhibition profile, they are expected to be useful for a wider variety of CNS disorders.

DETAILED DESCRIPTION OF THE INVENTION

The present invention relates to compounds represented by formulae I(A-D) having the following structure:

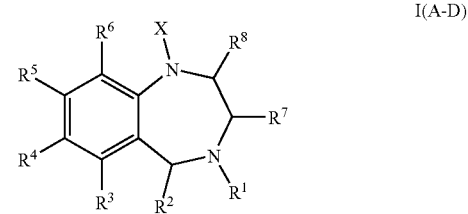

I(A-D)

where:
X represents a 5- or 6-membered aromatic or non-aromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^9$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^9$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^9$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^1$ and $R^2$ are each independently selected from the group consisting of H, $C_1$-$C_6$ alkyl, $C_2$-$C_6$ alkenyl, $C_2$-$C_6$-alkynyl, $C_3$-$C_6$ cycloalkyl, and $C_4$-$C_7$ cycloalkylalkyl, each of which is optionally substituted from 1 to 3 times with substituents as defined below in $R^{10}$; or $R^2$ is gem-dimethyl;

$R^3$, $R^5$, and $R^6$ are each independently selected from the group consisting of H, halogen, —$OR^{11}$, —$NR^{12}R^{13}$, $S(O)_n R^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^9$;

$R^4$ is H, halogen, —$OR^{11}$, —$NR^{12}R^{13}$, —$S(O)_n R^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; or $R^4$ is phenyl, pyridyl, 2-oxo-pyridin-1(2H)-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted monocyclic or bicyclic aryl or monocyclic or bicyclic heteroaryl and $R^4$ is H, —$OR^{11}$, —$NR^{12}R^{13}$, —$S(O)_n R^{14}$, —$C(O)R^{15}$, —CN, halogen or $C_1$-$C_6$ alkyl, wherein each of the $C_1$-$C_6$ alkyl is optionally substituted from 1 to 3 times with substituents as defined below in $R^{10}$; and provided that for compounds of formula ID, X is substituted monocyclic heteroaryl and $R^4$ is substituted monocyclic or bicyclic aryl or heteroaryl;

$R^7$ and $R^8$ are each independently selected from the group consisting of H, $C_1$-$C_6$ alkyl, $C_2$-$C_6$ alkenyl, $C_2$-$C_6$-alkynyl, $C_3$-$C_6$ cycloalkyl, and $C_4$-$C_7$ cycloalkylalkyl, each of which is optionally substituted from 1 to 3 times with substituents as defined below in $R^{10}$; or $R^2$, $R^7$, and $R^8$ are gem-dimethyl, with the proviso that only one of $R^7$ and $R^8$ is gem-dimethyl;

$R^9$ is independently selected at each occurrence from a substituent in the group consisting of halogen, —$NO_2$, —CN, —$OR^{11}$, —$NR^{12}R^{13}$, —$NR^{12}C(O)_2 R^{13}$, —$NR^{12}C(O)NR^{12}R^{13}$, —$S(O)_n R^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;

$R^{10}$ is independently selected at each occurrence from a substituent in the group consisting of —CN, halogen, $C_1$-$C_3$ alkyl, —$OR^{11}$, —$NR^{12}R^{13}$, —$S(O)_n R^{14}$, $C(O)R^{15}$, aryl, and heteroaryl, wherein each of the aryl or heteroaryl groups is optionally substituted from 1 to 4 times with substituents as defined above in $R^9$;

$R^{11}$ is selected from the group consisting of H, $C_1$-$C_4$ alkyl, $C_3$-$C_6$ cycloalkyl, $C_4$-$C_7$ cycloalkylalkyl, and —$C(O)R^{15}$, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{11}$ is selected from the group consisting of phenyl, benzyl, pyridazinyl, pyrimidinyl, pyrazinyl, other 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{12}$ and $R^{13}$ are each independently selected from the group consisting of H, —C(O)$R^{15}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$;

$R^{12}$ and $R^{13}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^9$;

$R^{12}$ and $R^{13}$ are each independently a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —S(O)$_n$$R^{14}$, and —C(O)$R^{15}$, with the proviso that only one of $R^{12}$ and $R^{13}$ is a bridged bicyclic ring;

$R^{12}$ and $R^{13}$ are taken together with the nitrogen to which they are attached to form a saturated or partially saturated monocyclic or bicyclic heterocycle selected from the group consisting of piperidine, pyrrolidine, morpholine, thiomorpholine, [1,2]oxazinane, isoxazolidine, 2-oxopiperidine, 2-oxopyrrolidine, 3-oxomorpholine, 3-oxothiomorpholine, 5,6,7,8-tetrahydroimidazo[1,2-c]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, —O$R^{11}$, —N$R^{12}R^{13}$, —S(O)$_n$$R^{14}$, —C(O)$R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in thr ring, where the heterocycle is optionally substituted on a ring carbon with from 1 to 3 times with a substituent selected independently at each occurrence thereof from the group consisting of halogen, cyano, —O$R^{11}$, —N$R^{12}R^{13}$, —S(O)$_n$$R^{14}$, —C(O)$R^{15}$, and $C_1$-$C_4$ alkyl, or on the additional nitrogen atom from 1 to 3 times with a substituent selected independently at each occurrence thereof from the group consisting of S(O)$_n$$R^{14}$, —C(O)$R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^9$; or when $R^4$ is —N$R^{12}R^{13}$ or —C(O)N$R^{12}R^{13}$, either $R^{12}$ or $R^{13}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{15}$, and —S(O)$_n$$R^{14}$, or either $R^{12}$ or $R^{13}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —C(O)$R^{15}$, and —S(O)$_n$$R^{14}$;

$R^{14}$ is selected from the group consisting of H, —N$R^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{14}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{15}$ is selected from the group consisting of H, —O$R^{11}$, —N$R^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{15}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

n is 0, 1 or 2;

with the following provisos that (1) when $R^1$ is H or benzyl, X cannot be phenyl; and (2) when $R^1$ is n-propyl, X cannot be phenyl or 3-(trifluoromethyl)phenyl;

or an oxide of, or a pharmaceutically acceptable salt thereof.

As used above, and throughout the description of the invention, the following terms, unless otherwise indicated, shall be understood to have the following meanings.

The term "monocyclic carbocycle" means a monocyclic ring system of 5 to about 8 ring carbon atoms, preferably 5 or 6. The ring is nonaromatic, but may contain one or more carbon-carbon double bonds. Representative monocyclic carbocycles include cyclopentyl, cyclohexyl, cyclopentenyl, cyclohexenyl, and the like.

The term "monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is nonaromatic, but may be fused to an aromatic ring. Representative monocyclic heterocycles include pyrrolidine, piperidine, piperazine, and the like.

The term "aromatic monocyclic carbocycle" means a monocyclic ring system of 5 to about 8 ring carbon atoms, preferably 6. The ring is aromatic. Representative monocyclic carbocycles include phenyl, and the like.

The term "aromatic monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is aromatic. Representative aromatic monocyclic heterocycles include pyrrole, pyridine, oxazole, thiazole, and the like. For lactam analogues of "aromatic monocyclic heterocycles" such as pyridin-2(1H)-one, pyridazin-3(2H)-one, and the like, when these lactam analogues are structurally connected through the nitrogen atom adjacent to the lactam carbonyl, these lactam analogues of aromatic monocyclic heterocycles are considered as "aromatic monocyclic heterocycles" in accordance with the present invention.

The term "fused bicyclic carbocycle" means a bicyclic ring system consisting of about 8 to 11 ring carbon atoms, preferably 9 or 10. One or both of the rings is/are aromatic. Representative fused bicyclic carbocycles include indenyl, indanyl, naphthyl, dihydronaphthyl, tetrahydronaphthyl, benzocycloheptenyl, dihydrobenzocycloheptenyl, tetrahydrobenzocycloheptenyl, and the like.

The term "fused bicyclic heterocycle" means a bicyclic ring system consisting of about 8 to 13 ring atoms, preferably 9 or 10, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. One or both of the rings is/are aromatic. Representative fused bicyclic heterocycles include benzofuranyl, benzothiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, 5,6,7,8-tetrahydro-[1,2,4]triazolo[4,3-a]pyrazinyl, [1,2,4]triazolo[4,3-a]pyrazinyl, thieno[2,3-b]pyridinyl, thieno[3,2-b]pyridinyl, 1H-pyrrolo[2,3-b]pyridinyl, chromenyl, dihydrobenzothiophenyl, dihydrobenzofuranyl, indolinyl, quinolinyl, isoquinolinyl, 4H-quinolizinyl, 9aH-quinolizinyl, quinazolinyl, cinnolinyl, quinoxalinyl, benzo[1,2,3]triazinyl, benzo[1,2,4]triazinyl, and the like. For lactam analogues of "fused bicyclic heterocycles" such as [1,2,4]triazolo[4,3-a]pyridin-3(2H)-one, and the like, when these lactams analogues are structurally connected through the nitrogen atom adjacent to the lactam carbonyl, these lactam analogues of aromatic monocyclic heterocycles are considered as "fused bicyclic heterocycles" in accordance with the present invention.

The term "bridged bicyclic ring" means a bridged bicyclic ring containing 6-12 carbon atoms and optionally containing one or more heteroatoms selected from the group consisting of oxygen, nitrogen, and sulfur. Representative bridged bicyclic rings include quinuclidine, 9-azabicyclo[3.3.1]nonane, 7-azabicyclo[2.2.1]heptane, 2,5-diazabicyclo[2.2.2]octane, and the like.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Representative alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Representative alkenyl groups include ethenyl, propenyl, n-butenyl, and i-butenyl.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Representative alkynyl groups include ethynyl, propynyl, n-butynyl, 2-butynyl, 3-methylbutynyl, and n-pentynyl.

The term "cycloalkyl" means a non-aromatic mono- or multicyclic ring system of about 3 to about 7 carbon atoms, preferably of about 5 to about 7 carbon atoms. Representative monocyclic cycloalkyl include cyclopentyl, cyclohexyl, cycloheptyl, and the like.

The term "cycloalkylalkyl" means a cycloalkyl-alkyl-group in which the cycloalkyl and alkyl are as defined herein. Representative cycloalkylalkyl groups include cyclopropylmethyl and cyclopentylmethyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of 6 to about 14 ring atoms, preferably of 6 to about 10 ring atoms, in which one or more of the atoms in the ring system is/are element(s) other than carbon, for example, nitrogen, oxygen or sulfur. Representative heteroaryl groups include pyridinyl, pyridazinyl and quinolinyl.

The term "alkoxy" means an alkyl-O-group where the alkyl group is as herein described. Representative alkoxy groups include methoxy, ethoxy, n-propoxy, i-propoxy, n-butoxy and heptoxy.

The term "halo" or "halogen" means fluoro, chloro, bromo, or iodo.

The term "haloalkyl" means both branched and straight-chain alkyl substituted with 1 or more halogen, where the alkyl group is as herein described.

The term "haloalkoxy" means a $C_{1-4}$ alkoxy group substituted by at least one halogen atom, where the alkoxy group is as herein described.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compounds of the invention", and equivalent expressions, are meant to embrace compounds of general formulae I(A-D), as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example Berge et al., *J Pharm Sci*, 66:1-sup.19 (1977) and *Remington's Pharmaceutical Sciences*, 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., *Methods in Enzymology*, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, *Advanced Drug Delivery Reviews*, 8:1-38 (1992); Bundgaard et al., *Journal of Pharmaceutical Sciences*, 77:285 (1988); Nakeya et al., *Chem Pharm Bull*, 32:692 (1984); Higuchi, "Pro-drugs as Novel Delivery Systems" Roche, ed., *A.C.S. Symposium Series*, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate and benzoate derivatives of alcohol and amine functional groups in the compounds of the invention.

The term "therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formulae I(A-D) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in *Remington's Pharmaceutical Sciences*, 17th ed, Easton, Pa., Mack Publishing Company (1985), which is hereby incorporated by reference in its entirety.

One embodiment of the present invention relates to the compound of formula (IA), where X is substituted phenyl and $R^4$ is substituted monocyclic or bicyclic aryl or heteroaryl.

Another embodiment of the present invention relates to the compound of formula (IB), where X is substituted bicyclic aryl or heteroaryl and $R^4$ is substituted monocyclic or bicyclic aryl or heteroaryl.

Another embodiment of the present invention relates to the compound of formula (IC), where X is substituted monocyclic or bicyclic aryl or monocyclic or bicyclic heteroaryl and $R^4$ is H, $-OR^{11}$, $-NR^{12}R^{13}$, $-S(O)_nR^{14}$, $-C(O)R^{15}$, $-CN$, halogen or $C_1$-$C_6$ alkyl, wherein each of the $C_1$-$C_6$ alkyl is optionally substituted from 1 to 3 times with substituents as defined below in $R^{10}$.

Another embodiment of the present invention relates to the compound of formula (ID), where X is substituted monocyclic heteroaryl and $R^4$ is substituted monocyclic or bicyclic aryl or heteroaryl.

Another embodiment of the present invention relates to the compound of formulae I(A-D) where:
X is phenyl, optionally substituted from 1 to 4 times with substituents as defined below in $R^9$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, or trifluoromethoxy;
$R^4$ is H, halogen, $-OR^{11}$, $-NR^{12}R^{13}$, $-S(O)_nR^{14}$, $-CN$, $-C(O)R^{15}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;
$R^5$ is H, methyl, hydroxyl, methoxy, fluoro, chloro, cyano, trifluoromethyl, or trifluoromethoxy;
$R^6$ is H, methyl, hydroxyl, methoxy, fluoro, chloro, cyano, trifluoromethyl, or trifluoromethoxy;
$R^7$ is H, gem-dimethyl, or $C_1$-$C_4$ alkyl, where each of the $C_1$-$C_4$ alkyl is optionally substituted from 1 to 3 times with substituents as defined below in $R^{10}$;
$R^8$ is H, gem-dimethyl, or $C_1$-$C_4$ alkyl, where each of the $C_1$-$C_4$ alkyl is optionally substituted from 1 to 3 times with substituents as defined below in $R^{10}$;
$R^9$ is independently selected at each occurrence from a substituent in the group consisting of halogen, $-NO_2$, $-CN$, $-OR^{11}$, $-NR^{12}R^{13}$, $-NR^{12}C(O)_2R^{13}$, $-NR^{12}C(O)NR^{12}R^{13}$, $-S(O)_nR^{14}$, $-C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and
$R^{10}$ is independently selected at each occurrence from a substituent in the group consisting of $-CN$, halogen, $C_1$-$C_3$ alkyl, $-OR^{11}$, $-NR^{12}R^{13}$, $-S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:
X is phenyl, optionally substituted from 1 to 4 times with substituents as defined below in $R^9$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, or trifluoromethoxy;
$R^4$ is phenyl, pyridyl, 2-oxo-pyridin-1(2H)-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:

X represents a 5- or 6-membered aromatic or non-aromatic monocyclic carbocycle or heterocycle selected from the group consisting of pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^9$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^4$ is H, halogen, —$OR^{11}$, —$NR^{12}R^{13}$, —$S(O)_nR^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:

X represents a 5- or 6-membered aromatic or non-aromatic monocyclic carbocycle or heterocycle selected from the group consisting of pyridyl, 2-oxo-pyridin-1(2H)-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^9$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^4$ is phenyl, pyridyl, 2-oxo-pyridin-1(2H)-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-c]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^9$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^4$ is H, halogen, —$OR^{11}$, —$NR^{12}R^{13}$, —$S(O)_nR^{14}$, —CN, —$C(O)R^{15}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^9$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^4$ is phenyl, pyridyl, 2-oxo-pyridin-1(2H)-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^9$;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Another embodiment of the present invention relates to the compound of formulae I(A-D) where:

X is a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^9$;

$R^1$ is H, methyl, ethyl, or isopropyl;

$R^2$ is H, methyl, or gem-dimethyl;

$R^4$ is H, methyl, hydroxyl, methoxy, fluoro, chloro, cyano, trifluoromethyl, or trifluoromethoxy;

$R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^9$, with the proviso that only one of $R^3$, $R^5$, and $R^6$ is 5- or 6-membered monocyclic carbocycle or heterocycle or a [5,5]-, [6,5]-, [6,6]-, or [6,7]-fused bicyclic carbocycle or heterocycle;

$R^7$ is H, gem-dimethyl, or $C_1$-$C_4$ alkyl, where each of the $C_1$-$C_4$ alkyl is optionally substituted from 1 to 3 times with substituents as defined below in $R^{10}$;

$R^8$ is H, gem-dimethyl, or $C_1$-$C_4$ alkyl, where each of the $C_1$-$C_4$ alkyl is optionally substituted from 1 to 3 times with substituents as defined below in $R^{10}$;

$R^9$ is independently selected at each occurrence from a substituent in the group consisting of halogen, —$NO_2$, —CN, —$OR^{11}$, —$NR^{12}R^{13}$, —$NR^{12}C(O)_2R^{13}$, —$NR^{12}C(O)NR^{12}R^{13}$, —$S(O)_nR^{14}$, —$C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; and $R^{10}$ is independently selected at each occurrence from a substituent in the group consisting of —CN, halogen, $C_1$-$C_3$ alkyl, —$OR^{11}$, —$NR^{12}R^{13}$, —$S(O)_nR^{14}$, $C(O)R^{15}$, aryl, and heteroaryl, wherein each of the aryl or heteroaryl groups is optionally substituted from 1 to 4 times with substituents as defined above in $R^9$.

Specific compounds of formulae I(A-D) of the present invention are the following tetrahydrobenzo-1,4-diazepine compounds:

1-phenyl-2,3,4,5-tetrahydro-1H-benzo[e][1,4]diazepine;

7-methyl-1-phenyl-2,3,4,5-tetrahydro-1H-benzo[e][1,4]diazepine;

7-fluoro-1-phenyl-2,3,4,5-tetrahydro-1H-benzo[e][1,4]diazepine;

1-phenyl-2,3,4,5-tetrahydro-1H-benzo[e][1,4]diazepine-7-carbonitrile;

1-phenyl-7-(trifluoromethyl)-2,3,4,5-tetrahydro-1H-benzo[e][1,4]diazepine 7-methoxy-1-phenyl-2,3,4,5-tetrahydro-1H-benzo[e][1,4]diazepine;

1-phenyl-7-(trifluoromethoxy)-2,3,4,5-tetrahydro-1H-benzo[e][1,4]diazepine;

4-methyl-1-phenyl-2,3,4,5-tetrahydro-1H-benzo[e][1,4]diazepine;

4-ethyl-1-phenyl-2,3,4,5-tetrahydro-1H-benzo[e][1,4]diazepine;

4-isopropyl-1-phenyl-2,3,4,5-tetrahydro-1H-benzo[e][1,4]diazepine;

4,7-dimethyl-1-phenyl-2,3,4,5-tetrahydro-1H-benzo[e][1,4]diazepine;

7-fluoro-4-methyl-1-phenyl-2,3,4,5-tetrahydro-1H-benzo[e][1,4]diazepine;

7-chloro-4-methyl-1-phenyl-2,3,4,5-tetrahydro-1H-benzo[e][1,4]diazepine;

7-bromo-4-methyl-1-phenyl-2,3,4,5-tetrahydro-1H-benzo[e][1,4]diazepine;

4-methyl-1-phenyl-2,3,4,5-tetrahydro-1H-benzo[e][1,4]diazepine-7-carbonitrile;

4-methyl-1-phenyl-7-(trifluoromethyl)-2,3,4,5-tetrahydro-1H-benzo[e][1,4]diazepine;

7-methoxy-4-methyl-1-phenyl-2,3,4,5-tetrahydro-1H-benzo[e][1,4]diazepine;

4-methyl-1-phenyl-7-(trifluoromethoxy)-2,3,4,5-tetrahydro-1H-benzo[e][1,4]diazepine;

4-methyl-1-phenyl-2,3,4,5-tetrahydro-1H-benzo[e][1,4]diazepin-7-ol;

1-(2-fluorophenyl)-4-methyl-2,3,4,5-tetrahydro-1H-benzo[e][1,4]diazepine;
1-(3-fluorophenyl)-4-methyl-2,3,4,5-tetrahydro-1H-benzo[e][1,4]diazepine;
1-(4-fluorophenyl)-4-methyl-2,3,4,5-tetrahydro-1H-benzo[e][1,4]diazepine;
1-(2-chlorophenyl)-4-methyl-2,3,4,5-tetrahydro-1H-benzo[e][1,4]diazepine;
1-(3-chlorophenyl)-4-methyl-2,3,4,5-tetrahydro-1H-benzo[e][1,4]diazepine;
1-(4-chlorophenyl)-4-methyl-2,3,4,5-tetrahydro-1H-benzo[e][1,4]diazepine;
1-(2-fluorophenyl)-4-methyl-2,3,4,5-tetrahydro-1H-benzo[e][1,4]diazepine-7-carbonitrile;
1-(3-fluorophenyl)-4-methyl-2,3,4,5-tetrahydro-1H-benzo[e][1,4]diazepine-7-carbonitrile;
1-(4-fluorophenyl)-4-methyl-2,3,4,5-tetrahydro-1H-benzo[e][1,4]diazepine-7-carbonitrile;
1-(2-chlorophenyl)-4-methyl-2,3,4,5-tetrahydro-1H-benzo[e][1,4]diazepine-7-carbonitrile;
1-(3-chlorophenyl)-4-methyl-2,3,4,5-tetrahydro-1H-benzo[e][1,4]diazepine-7-carbonitrile;
1-(4-chlorophenyl)-4-methyl-2,3,4,5-tetrahydro-1H-benzo[e][1,4]diazepine-7-carbonitrile;
7-fluoro-1-(2-fluorophenyl)-4-methyl-2,3,4,5-tetrahydro-1H-benzo[e][1,4]diazepine;
7-fluoro-1-(3-fluorophenyl)-4-methyl-2,3,4,5-tetrahydro-1H-benzo[e][1,4]diazepine;
7-fluoro-1-(4-fluorophenyl)-4-methyl-2,3,4,5-tetrahydro-1H-benzo[e][1,4]diazepine;
1-(2-chlorophenyl)-7-fluoro-4-methyl-2,3,4,5-tetrahydro-1H-benzo[e][1,4]diazepine;
1-(3-chlorophenyl)-7-fluoro-4-methyl-2,3,4,5-tetrahydro-1H-benzo[e][1,4]diazepine;
1-(4-chlorophenyl)-7-fluoro-4-methyl-2,3,4,5-tetrahydro-1H-benzo[e][1,4]diazepine;
1-(2-fluorophenyl)-4-methyl-7-(trifluoromethyl)-2,3,4,5-tetrahydro-1H-benzo[e][1,4]diazepine;
1-(3-fluorophenyl)-4-methyl-7-(trifluoromethyl)-2,3,4,5-tetrahydro-1H-benzo[e][1,4]diazepine;
1-(4-fluorophenyl)-4-methyl-7-(trifluoromethyl)-2,3,4,5-tetrahydro-1H-benzo[e][1,4]diazepine;
1-(2-chlorophenyl)-4-methyl-7-(trifluoromethyl)-2,3,4,5-tetrahydro-1H-benzo[e][1,4]diazepine;
1-(3-chlorophenyl)-4-methyl-7-(trifluoromethyl)-2,3,4,5-tetrahydro-1H-benzo[e][1,4]diazepine;
1-(4-chlorophenyl)-4-methyl-7-(trifluoromethyl)-2,3,4,5-tetrahydro-1H-benzo[e][1,4]diazepine;
1-(2-fluorophenyl)-7-methoxy-4-methyl-2,3,4,5-tetrahydro-1H-benzo[e][1,4]diazepine;
1-(3-fluorophenyl)-7-methoxy-4-methyl-2,3,4,5-tetrahydro-1H-benzo[e][1,4]diazepine;
1-(4-fluorophenyl)-7-methoxy-4-methyl-2,3,4,5-tetrahydro-1H-benzo[e][1,4]diazepine;
1-(2-chlorophenyl)-7-methoxy-4-methyl-2,3,4,5-tetrahydro-1H-benzo[e][1,4]diazepine;
1-(3-chlorophenyl)-7-methoxy-4-methyl-2,3,4,5-tetrahydro-1H-benzo[e][1,4]diazepine;
1-(4-chlorophenyl)-7-methoxy-4-methyl-2,3,4,5-tetrahydro-1H-benzo[e][1,4]diazepine;
1-(2-fluorophenyl)-4-methyl-7-(trifluoromethoxy)-2,3,4,5-tetrahydro-1H-benzo[e][1,4]diazepine;
1-(3-fluorophenyl)-4-methyl-7-(trifluoromethoxy)-2,3,4,5-tetrahydro-1H-benzo[e][1,4]diazepine;
1-(4-fluorophenyl)-4-methyl-7-(trifluoromethoxy)-2,3,4,5-tetrahydro-1H-benzo[e][1,4]diazepine;
1-(2-chlorophenyl)-4-methyl-7-(trifluoromethoxy)-2,3,4,5-tetrahydro-1H-benzo[e][1,4]diazepine;
1-(3-chlorophenyl)-4-methyl-7-(trifluoromethoxy)-2,3,4,5-tetrahydro-1H-benzo[e][1,4]diazepine;
1-(4-chlorophenyl)-4-methyl-7-(trifluoromethoxy)-2,3,4,5-tetrahydro-1H-benzo[e][1,4]diazepine;
1-(1-(4-fluorophenyl)-4-methyl-2,3,4,5-tetrahydro-1H-benzo[e][1,4]diazepin-7-yl)ethanone;
1-(1-(4-chlorophenyl)-4-methyl-2,3,4,5-tetrahydro-1H-benzo[e][1,4]diazepin-7-yl)ethanone;
1-(3,5-difluorophenyl)-4-methyl-2,3,4,5-tetrahydro-1H-benzo[e][1,4]diazepine;
1-(2,4-difluorophenyl)-4-methyl-2,3,4,5-tetrahydro-1H-benzo[e][1,4]diazepine;
1-(3,4-difluorophenyl)-4-methyl-2,3,4,5-tetrahydro-1H-benzo[e][1,4]diazepine;
1-(3,5-difluorophenyl)-4-methyl-2,3,4,5-tetrahydro-1H-benzo[e][1,4]diazepine-7-carbonitrile;
1-(2,4-difluorophenyl)-4-methyl-2,3,4,5-tetrahydro-1H-benzo[e][1,4]diazepine-7-carbonitrile;
1-(3,4-difluorophenyl)-4-methyl-2,3,4,5-tetrahydro-1H-benzo[e][1,4]diazepine-7-carbonitrile;
1-(3,5-difluorophenyl)-7-fluoro-4-methyl-2,3,4,5-tetrahydro-1H-benzo[e][1,4]diazepine;
1-(2,4-difluorophenyl)-7-fluoro-4-methyl-2,3,4,5-tetrahydro-1H-benzo[e][1,4]diazepine;
1-(3,4-difluorophenyl)-7-fluoro-4-methyl-2,3,4,5-tetrahydro-1H-benzo[e][1,4]diazepine;
7-bromo-1-(3,5-difluorophenyl)-4-methyl-2,3,4,5-tetrahydro-1H-benzo[e][1,4]diazepine;
7-bromo-1-(2,4-difluorophenyl)-4-methyl-2,3,4,5-tetrahydro-1H-benzo[e][1,4]diazepine;
7-bromo-1-(3,4-difluorophenyl)-4-methyl-2,3,4,5-tetrahydro-1H-benzo[e][1,4]diazepine;
1-(3,5-difluorophenyl)-4-methyl-7-(trifluoromethyl)-2,3,4,5-tetrahydro-1H-benzo[e][1,4]diazepine;
1-(2,4-difluorophenyl)-4-methyl-7-(trifluoromethyl)-2,3,4,5-tetrahydro-1H-benzo[e][1,4]diazepine;
1-(3,4-difluorophenyl)-4-methyl-7-(trifluoromethyl)-2,3,4,5-tetrahydro-1H-benzo[e][1,4]diazepine;
1-(3,5-difluorophenyl)-4-methyl-7-(trifluoromethoxy)-2,3,4,5-tetrahydro-1H-benzo[e][1,4]diazepine;
1-(2,4-difluorophenyl)-4-methyl-7-(trifluoromethoxy)-2,3,4,5-tetrahydro-1H-benzo[e][1,4]diazepine;
1-(3,4-difluorophenyl)-4-methyl-7-(trifluoromethoxy)-2,3,4,5-tetrahydro-1H-benzo[e][1,4]diazepine;
1-(3,5-difluorophenyl)-7-methoxy-4-methyl-2,3,4,5-tetrahydro-1H-benzo[e][1,4]diazepine;
1-(2,4-difluorophenyl)-7-methoxy-4-methyl-2,3,4,5-tetrahydro-1H-benzo[e][1,4]diazepine;
1-(3,4-difluorophenyl)-7-methoxy-4-methyl-2,3,4,5-tetrahydro-1H-benzo[e][1,4]diazepine;
1-(3,4-dichlorophenyl)-4-methyl-2,3,4,5-tetrahydro-1H-benzo[e][1,4]diazepine-7-carbonitrile;
1-(3,4-dichlorophenyl)-4-methyl-7-(trifluoromethoxy)-2,3,4,5-tetrahydro-1H-benzo[e][1,4]diazepine;
1-(3,4-dichlorophenyl)-7-fluoro-4-methyl-2,3,4,5-tetrahydro-1H-benzo[e][1,4]diazepine;
1-(3,4-dichlorophenyl)-7-methoxy-4-methyl-2,3,4,5-tetrahydro-1H-benzo[e][1,4]diazepine;
7-bromo-1-(3,4-dichlorophenyl)-4-methyl-2,3,4,5-tetrahydro-1H-benzo[e][1,4]diazepine;
4-methyl-1-(naphthalen-2-yl)-2,3,4,5-tetrahydro-1H-benzo[e][1,4]diazepine;
4-methyl-1-(naphthalen-2-yl)-2,3,4,5-tetrahydro-1H-benzo[e][1,4]diazepine-7-carbonitrile;

7-fluoro-4-methyl-1-(naphthalen-2-yl)-2,3,4,5-tetrahydro-1H-benzo[e][1,4]diazepine;
7-bromo-4-methyl-1-(naphthalen-2-yl)-2,3,4,5-tetrahydro-1H-benzo[e][1,4]diazepine;
4-methyl-1-(naphthalen-2-yl)-7-(trifluoromethoxy)-2,3,4,5-tetrahydro-1H-benzo[e][1,4]diazepine;
4-methyl-1-(naphthalen-2-yl)-7-(trifluoromethyl)-2,3,4,5-tetrahydro-1H-benzo[e][1,4]diazepine;
1-(4-methyl-1-(naphthalen-2-yl)-2,3,4,5-tetrahydro-1H-benzo[e][1,4]diazepin-7-yl)ethanone;
1-(4-methyl-1-(naphthalen-2-yl)-2,3,4,5-tetrahydro-1H-benzo[e][1,4]diazepin-7-yl)pyridin-2(1H)one;
4-methyl-1-(naphthalen-2-yl)-2,3,4,5-tetrahydro-1H-benzo[e][1,4]diazepine-7-carbonitrile;
7-fluoro-4-methyl-1-(naphthalen-1-yl)-2,3,4,5-tetrahydro-1H-benzo[e][1,4]diazepine;
7-bromo-4-methyl-1-(naphthalen-1-yl)-2,3,4,5-tetrahydro-1H-benzo[e][1,4]diazepine;
4-methyl-1-(naphthalen-1-yl)-7-(trifluoromethoxy)-2,3,4,5-tetrahydro-1H-benzo[e][1,4]diazepine;
4-methyl-1-(naphthalen-1-yl)-7-(trifluoromethyl)-2,3,4,5-tetrahydro-1H-benzo[e][1,4]diazepine;
1-(4-methyl-1-(naphthalen-1-yl)-2,3,4,5-tetrahydro-1H-benzo[e][1,4]diazepin-7-yl)ethanone;
1-(1-fluoronaphthalen-2-yl)-4-methyl-2,3,4,5-tetrahydro-1H-benzo[e][1,4]diazepine-7-carbonitrile;
1-(4-fluoronaphthalen-2-yl)-4-methyl-2,3,4,5-tetrahydro-1H-benzo[e][1,4]diazepine-7-carbonitrile;
1-(5-fluoronaphthalen-2-yl)-4-methyl-2,3,4,5-tetrahydro-1H-benzo[e][1,4]diazepine-7-carbonitrile;
1-(1-(1-fluoronaphthalen-2-yl)-4-methyl-2,3,4,5-tetrahydro-1H-benzo[e][1,4]diazepin-7-yl)ethanone;
1-(1-(4-fluoronaphthalen-2-yl)-4-methyl-2,3,4,5-tetrahydro-1H-benzo[e][1,4]diazepin-7-yl)ethanone;
1-(1-(5-fluoronaphthalen-2-yl)-4-methyl-2,3,4,5-tetrahydro-1H-benzo[e][1,4]diazepin-7-yl)ethanone;
1-(benzo[d][1,3]dioxol-5-yl)-4-methyl-2,3,4,5-tetrahydro-1H-benzo[e][1,4]diazepine;
1-(benzo[d][1,3]dioxol-5-yl)-7-bromo-4-methyl-2,3,4,5-tetrahydro-1H-benzo[e][1,4]diazepine;
1-(benzo[d][1,3]dioxol-5-yl)-4-methyl-2,3,4,5-tetrahydro-1H-benzo[e][1,4]diazepine-7-carbonitrile;
1-(benzo[d][1,3]dioxol-5-yl)-4-methyl-7-(trifluoromethyl)-2,3,4,5-tetrahydro-1H-benzo[e][1,4]diazepine;
1-(benzo[d][1,3]dioxol-5-yl)-4-methyl-7-(trifluoromethoxy)-2,3,4,5-tetrahydro-1H-benzo[e][1,4]diazepine;
1-(benzo[d][1,3]dioxol-5-yl)-7-methoxy-4-methyl-2,3,4,5-tetrahydro-1H-benzo[e][1,4]diazepine;
1-(benzo[b]thiophen-2-yl)-4-methyl-2,3,4,5-tetrahydro-1H-benzo[e][1,4]diazepine-7-carbonitrile;
1-(benzo[b]thiophen-5-yl)-4-methyl-2,3,4,5-tetrahydro-1H-benzo[e][1,4]diazepine-7-carbonitrile;
1-(benzo[b]thiophen-6-yl)-4-methyl-2,3,4,5-tetrahydro-1H-benzo[e][1,4]diazepine-7-carbonitrile;
1-(benzofuran-2-yl)-4-methyl-2,3,4,5-tetrahydro-1H-benzo[e][1,4]diazepine-7-carbonitrile;
1-(benzofuran-5-yl)-4-methyl-2,3,4,5-tetrahydro-1H-benzo[e][1,4]diazepine-7-carbonitrile;
1-(benzofuran-6-yl)-4-methyl-2,3,4,5-tetrahydro-1H-benzo[e][1,4]diazepine-7-carbonitrile;
4-(4-methyl-1-phenyl-2,3,4,5-tetrahydro-1H-benzo[e][1,4]diazepin-7-yl)morpholine;
4-methyl-1-phenyl-7-(piperazin-1-yl)-2,3,4,5-tetrahydro-1H-benzo[e][1,4]diazepine;
4-methyl-7-(4-methylpiperazin-1-yl)-1-phenyl-2,3,4,5-tetrahydro-1H-benzo[e][1,4]diazepine;
7-(4-(ethylsulfonyl)piperazin-1-yl)-4-methyl-1-phenyl-2,3,4,5-tetrahydro-1H-benzo[e][1,4]diazepine;
1-(4-(4-methyl-1-phenyl-2,3,4,5-tetrahydro-1H-benzo[e][1,4]diazepin-7-yl)piperazin-1-yl)ethanone;
3-(4-methyl-1-phenyl-2,3,4,5-tetrahydro-1H-benzo[e][1,4]diazepin-7-yl)oxazolidin-2-one;
1-(4-methyl-1-phenyl-2,3,4,5-tetrahydro-1H-benzo[e][1,4]diazepin-7-yl)pyrrolidin-2-one;
1-(4-methyl-1-phenyl-2,3,4,5-tetrahydro-1H-benzo[e][1,4]diazepin-7-yl)piperidin-2-one;
4-(1-(4-fluorophenyl)-4-methyl-2,3,4,5-tetrahydro-1H-benzo[e][1,4]diazepin-7-yl)morpholine;
1-(4-fluorophenyl)-4-methyl-7-(piperazin-1-yl)-2,3,4,5-tetrahydro-1H-benzo[e][1,4]diazepine;
1-(4-fluorophenyl)-4-methyl-7-(4-methylpiperazin-1-yl)-2,3,4,5-tetrahydro-1H-benzo[e][1,4]diazepine;
7-(4-(ethylsulfonyl)piperazin-1-yl)-1-(4-fluorophenyl)-4-methyl-2,3,4,5-tetrahydro-1H-benzo[e][1,4]diazepine;
1-(4-(1-(4-fluorophenyl)-4-methyl-2,3,4,5-tetrahydro-1H-benzo[e][1,4]diazepin-7-yl)piperazin-1-yl)ethanone;
3-(1-(4-fluorophenyl)-4-methyl-2,3,4,5-tetrahydro-1H-benzo[e][1,4]diazepin-7-yl)oxazolidin-2-one;
1-(1-(4-fluorophenyl)-4-methyl-2,3,4,5-tetrahydro-1H-benzo[e][1,4]diazepin-7-yl)pyrrolidin-2-one;
1-(1-(4-fluorophenyl)-4-methyl-2,3,4,5-tetrahydro-1H-benzo[e][1,4]diazepin-7-yl)piperidin-2-one;
4-(1-(2-fluorophenyl)-4-methyl-2,3,4,5-tetrahydro-1H-benzo[e][1,4]diazepin-7-yl)morpholine;
1-(2-fluorophenyl)-4-methyl-7-(piperazin-1-yl)-2,3,4,5-tetrahydro-1H-benzo[e][1,4]diazepine;
1-(2-fluorophenyl)-4-methyl-7-(4-methylpiperazin-1-yl)-2,3,4,5-tetrahydro-1H-benzo[e][1,4]diazepine;
7-(4-(ethylsulfonyl)piperazin-1-yl)-1-(2-fluorophenyl)-4-methyl-2,3,4,5-tetrahydro-1H-benzo[e][1,4]diazepine;
1-(4-(1-(2-fluorophenyl)-4-methyl-2,3,4,5-tetrahydro-1H-benzo[e][1,4]diazepin-7-yl)piperazin-1-yl)ethanone;
3-(1-(2-fluorophenyl)-4-methyl-2,3,4,5-tetrahydro-1H-benzo[e][1,4]diazepin-7-yl)oxazolidin-2-one;
1-(1-(2-fluorophenyl)-4-methyl-2,3,4,5-tetrahydro-1H-benzo[e][1,4]diazepin-7-yl)pyrrolidin-2-one;
1-(1-(2-fluorophenyl)-4-methyl-2,3,4,5-tetrahydro-1H-benzo[e][1,4]diazepin-7-yl)piperidin-2-one;
4-(1-(4-chlorophenyl)-4-methyl-2,3,4,5-tetrahydro-1H-benzo[e][1,4]diazepin-7-yl)morpholine;
4-(1-(4-chlorophenyl)-4-methyl-2,3,4,5-tetrahydro-1H-benzo[e][1,4]diazepin-7-yl)benzamide;
1-(4-chlorophenyl)-4-methyl-7-(piperazin-1-yl)-2,3,4,5-tetrahydro-1H-benzo[e][1,4]diazepine;
1-(4-chlorophenyl)-4-methyl-7-(4-methylpiperazin-1-yl)-2,3,4,5-tetrahydro-1H-benzo[e][1,4]diazepine;
7-(4-(ethylsulfonyl)piperazin-1-yl)-1-(4-chlorophenyl)-4-methyl-2,3,4,5-tetrahydro-1H-benzo[e][1,4]diazepine;
1-(4-(1-(4-chlorophenyl)-4-methyl-2,3,4,5-tetrahydro-1H-benzo[e][1,4]diazepin-7-yl)piperazin-1-yl)ethanone;
3-(1-(4-chlorophenyl)-4-methyl-2,3,4,5-tetrahydro-1H-benzo[e][1,4]diazepin-7-yl)oxazolidin-2-one;
1-(1-(4-chlorophenyl)-4-methyl-2,3,4,5-tetrahydro-1H-benzo[e][1,4]diazepin-7-yl)pyrrolidin-2-one;
1-(1-(4-chlorophenyl)-4-methyl-2,3,4,5-tetrahydro-1H-benzo[e][1,4]diazepin-7-yl)piperidin-2-one;
1-(1-(4-chlorophenyl)-4-methyl-2,3,4,5-tetrahydro-1H-benzo[e][1,4]diazepin-7-yl)pyridin-2(1H)-one;
4-(1-(3,5-difluorophenyl)-4-methyl-2,3,4,5-tetrahydro-1H-benzo[e][1,4]diazepin-7-yl)morpholine;
1-(3,5-difluorophenyl)-4-methyl-7-(piperazin-1-yl)-2,3,4,5-tetrahydro-1H-benzo[e][1,4]diazepine;

1-(3,5-difluorophenyl)-4-methyl-7-(4-methylpiperazin-1-yl)-2,3,4,5-tetrahydro-1H-benzo[e][1,4]diazepine;
1-(3,5-difluorophenyl)-7-(4-(ethylsulfonyl)piperazin-1-yl)-4-methyl-2,3,4,5-tetrahydro-1H-benzo[e][1,4]diazepine;
1-(4-(1-(3,5-difluorophenyl)-4-methyl-2,3,4,5-tetrahydro-1H-benzo[e][1,4]diazepin-7-yl)piperazin-1-yl)ethanone;
3-(1-(3,5-difluorophenyl)-4-methyl-2,3,4,5-tetrahydro-1H-benzo[e][1,4]diazepin-7-yl)oxazolidin-2-one;
1-(1-(3,5-difluorophenyl)-4-methyl-2,3,4,5-tetrahydro-1H-benzo[e][1,4]diazepin-7-yl)pyrrolidin-2-one;
1-(1-(3,5-difluorophenyl)-4-methyl-2,3,4,5-tetrahydro-1H-benzo[e][1,4]diazepin-7-yl)piperidin-2-one;
4-(1-(2,4-difluorophenyl)-4-methyl-2,3,4,5-tetrahydro-1H-benzo[e][1,4]diazepin-7-yl)morpholine;
1-(2,4-difluorophenyl)-4-methyl-7-(pyridazin-3-yl)-2,3,4,5-tetrahydro-1H-benzo[e][1,4]diazepine;
1-(2,4-difluorophenyl)-4-methyl-7-(piperazin-1-yl)-2,3,4,5-tetrahydro-1H-benzo[e][1,4]diazepine;
1-(2,4-difluorophenyl)-4-methyl-7-(4-methylpiperazin-1-yl)-2,3,4,5-tetrahydro-1H-benzo[e][1,4]diazepine;
1-(2,4-difluorophenyl)-7-(4-(ethylsulfonyl)piperazin-1-yl)-4-methyl-2,3,4,5-tetrahydro-1H-benzo[e][1,4]diazepine;
1-(4-(1-(2,4-difluorophenyl)-4-methyl-2,3,4,5-tetrahydro-1H-benzo[e][1,4]diazepin-7-yl)piperazin-1-yl)ethanone;
3-(1-(2,4-difluorophenyl)-4-methyl-2,3,4,5-tetrahydro-1H-benzo[e][1,4]diazepin-7-yl)oxazolidin-2-one;
1-(1-(2,4-difluorophenyl)-4-methyl-2,3,4,5-tetrahydro-1H-benzo[e][1,4]diazepin-7-yl)pyrrolidin-2-one;
1-(1-(2,4-difluorophenyl)-4-methyl-2,3,4,5-tetrahydro-1H-benzo[e][1,4]diazepin-7-yl)piperidin-2-one;
4-(1-(3,4-difluorophenyl)-4-methyl-2,3,4,5-tetrahydro-1H-benzo[e][1,4]diazepin-7-yl)morpholine;
1-(3,4-difluorophenyl)-4-methyl-7-(piperazin-1-yl)-2,3,4,5-tetrahydro-1H-benzo[e][1,4]diazepine;
1-(3,4-difluorophenyl)-4-methyl-7-(4-methylpiperazin-1-yl)-2,3,4,5-tetrahydro-1H-benzo[e][1,4]diazepine;
1-(3,4-difluorophenyl)-7-(4-(ethylsulfonyl)piperazin-1-yl)-4-methyl-2,3,4,5-tetrahydro-1H-benzo[e][1,4]diazepine;
1-(4-(1-(3,4-difluorophenyl)-4-methyl-2,3,4,5-tetrahydro-1H-benzo[e][1,4]diazepin-7-yl)piperazin-1-yl)ethanone;
3-(1-(3,4-difluorophenyl)-4-methyl-2,3,4,5-tetrahydro-1H-benzo[e][1,4]diazepin-7-yl)oxazolidin-2-one;
1-(1-(3,4-difluorophenyl)-4-methyl-2,3,4,5-tetrahydro-1H-benzo[e][1,4]diazepin-7-yl)pyrrolidin-2-one;
1-(1-(3,4-difluorophenyl)-4-methyl-2,3,4,5-tetrahydro-1H-benzo[e][1,4]diazepin-7-yl)piperidin-2-one;
4-(1-(3,4-dichlorophenyl)-4-methyl-2,3,4,5-tetrahydro-1H-benzo[e][1,4]diazepin-7-yl)morpholine;
1-(3,4-dichlorophenyl)-4-methyl-7-(piperazin-1-yl)-2,3,4,5-tetrahydro-1H-benzo[e][1,4]diazepine;
1-(3,4-dichlorophenyl)-4-methyl-7-(4-methylpiperazin-1-yl)-2,3,4,5-tetrahydro-1H-benzo[e][1,4]diazepine;
1-(3,4-dichlorophenyl)-7-(4-(ethylsulfonyl)piperazin-1-yl)-4-methyl-2,3,4,5-tetrahydro-1H-benzo[e][1,4]diazepine;
1-(4-(1-(3,4-dichlorophenyl)-4-methyl-2,3,4,5-tetrahydro-1H-benzo[e][1,4]diazepin-7-yl)piperazin-1-yl)ethanone;
3-(1-(3,4-dichlorophenyl)-4-methyl-2,3,4,5-tetrahydro-1H-benzo[e][1,4]diazepin-7-yl)oxazolidin-2-one;
1-(1-(3,4-dichlorophenyl)-4-methyl-2,3,4,5-tetrahydro-1H-benzo[e][1,4]diazepin-7-yl)pyrrolidin-2-one;
1-(1-(3,4-dichlorophenyl)-4-methyl-2,3,4,5-tetrahydro-1H-benzo[e][1,4]diazepin-7-yl)piperidin-2-one;
4-methyl-7-(2-(methylsulfonyl)phenyl)-1-phenyl-2,3,4,5-tetrahydro-1H-benzo[e][1,4]diazepine;
4-methyl-7-(3-(methylsulfonyl)phenyl)-1-phenyl-2,3,4,5-tetrahydro-1H-benzo[e][1,4]diazepine;
4-methyl-7-(4-(methylsulfonyl)phenyl)-1-phenyl-2,3,4,5-tetrahydro-1H-benzo[e][1,4]diazepine;
2-(4-methyl-1-phenyl-2,3,4,5-tetrahydro-1H-benzo[e][1,4]diazepin-7-yl)benzonitrile;
3-(4-methyl-1-phenyl-2,3,4,5-tetrahydro-1H-benzo[e][1,4]diazepin-7-yl)benzonitrile;
4-(4-methyl-1-phenyl-2,3,4,5-tetrahydro-1H-benzo[e][1,4]diazepin-7-yl)benzonitrile;
(4-fluorophenyl)-4-methyl-7-(2-(methylsulfonyl)phenyl)-2,3,4,5-tetrahydro-1H-benzo[e][1,4]diazepine;
1-(4-fluorophenyl)-4-methyl-7-(3-(methylsulfonyl)phenyl)-2,3,4,5-tetrahydro-1H-benzo[e][1,4]diazepine;
1-(4-fluorophenyl)-4-methyl-7-(4-(methylsulfonyl)phenyl)-2,3,4,5-tetrahydro-1H-benzo[e][1,4]diazepine;
1-(4-chlorophenyl)-4-methyl-7-(2-(methylsulfonyl)phenyl)-2,3,4,5-tetrahydro-1H-benzo[e][1,4]diazepine;
1-(4-chlorophenyl)-4-methyl-7-(3-(methylsulfonyl)phenyl)-2,3,4,5-tetrahydro-1H-benzo[e][1,4]diazepine;
1-(4-chlorophenyl)-4-methyl-7-(4-(methylsulfonyl)phenyl)-2,3,4,5-tetrahydro-1H-benzo[e][1,4]diazepine;
1-(3,5-difluorophenyl)-4-methyl-7-(2-(methylsulfonyl)phenyl)-2,3,4,5-tetrahydro-1H-benzo[e][1,4]diazepine;
1-(3,5-difluorophenyl)-4-methyl-7-(3-(methylsulfonyl)phenyl)-2,3,4,5-tetrahydro-1H-benzo[e][1,4]diazepine;
1-(3,5-difluorophenyl)-4-methyl-7-(4-(methylsulfonyl)phenyl)-2,3,4,5-tetrahydro-1H-benzo[e][1,4]diazepine;
1-(3,4-difluorophenyl)-4-methyl-7-(2-(methylsulfonyl)phenyl)-2,3,4,5-tetrahydro-1H-benzo[e][1,4]diazepine;
1-(3,4-difluorophenyl)-4-methyl-7-(3-(methylsulfonyl)phenyl)-2,3,4,5-tetrahydro-1H-benzo[e][1,4]diazepine;
1-(3,4-difluorophenyl)-4-methyl-7-(4-(methylsulfonyl)phenyl)-2,3,4,5-tetrahydro-1H-benzo[e][1,4]diazepine;
4-methyl-7-(2-(methylsulfonyl)phenyl)-1-(naphthalen-2-yl)-2,3,4,5-tetrahydro-1H-benzo[e][1,4]diazepine;
4-methyl-7-(4-(methylsulfonyl)phenyl)-1-(naphthalen-2-yl)-2,3,4,5-tetrahydro-1H-benzo[e][1,4]diazepine;
2-(4-methyl-1-phenyl-2,3,4,5-tetrahydro-1H-benzo[e][1,4]diazepin-7-yl)thiazole;
2-(4-methyl-1-phenyl-2,3,4,5-tetrahydro-1H-benzo[e][1,4]diazepin-7-yl)oxazole;
4-methyl-1-phenyl-7-(1H-pyrazol-4-yl)-2,3,4,5-tetrahydro-1H-benzo[e][1,4]diazepine;
4-methyl-1-phenyl-7-(1H-pyrazol-1-yl)-2,3,4,5-tetrahydro-1H-benzo[e][1,4]diazepine;
2-(4-methyl-1-phenyl-2,3,4,5-tetrahydro-1H-benzo[e][1,4]diazepin-7-yl)-1,3,4-thiadiazole;
5-(4-methyl-1-phenyl-2,3,4,5-tetrahydro-1H-benzo[e][1,4]diazepin-7-yl)-1,2,4-thiadiazole;
2-(4-methyl-1-phenyl-2,3,4,5-tetrahydro-1H-benzo[e][1,4]diazepin-7-yl)-1,3,4-oxadiazole;
4-methyl-1-phenyl-7-(1H-1,2,4-triazol-1-yl)-2,3,4,5-tetrahydro-1H-benzo[e][1,4]diazepine;
2-(1-(4-fluorophenyl)-4-methyl-2,3,4,5-tetrahydro-1H-benzo[e][1,4]diazepin-7-yl)thiazole;
2-(1-(4-fluorophenyl)-4-methyl-2,3,4,5-tetrahydro-1H-benzo[e][1,4]diazepin-7-yl)oxazole;
1-(4-fluorophenyl)-4-methyl-7-(1H-pyrazol-1-yl)-2,3,4,5-tetrahydro-1H-benzo[e][1,4]diazepine;
1-(4-fluorophenyl)-4-methyl-7-(1H-pyrazol-4-yl)-2,3,4,5-tetrahydro-1H-benzo[e][1,4]diazepine;
2-(1-(4-fluorophenyl)-4-methyl-2,3,4,5-tetrahydro-1H-benzo[e][1,4]diazepin-7-yl)-1,3,4-oxadiazole;
2-(1-(4-fluorophenyl)-4-methyl-2,3,4,5-tetrahydro-1H-benzo[e][1,4]diazepin-7-yl)-1,3,4-thiadiazole;
5-(1-(4-fluorophenyl)-4-methyl-2,3,4,5-tetrahydro-1H-benzo[e][1,4]diazepin-7-yl)-1,2,4-thiadiazole;

1-(4-fluorophenyl)-4-methyl-7-(1H-1,2,4-triazol-1-yl)-2,3,4,5-tetrahydro-1H-benzo[e][1,4]diazepine;
2-(1-(4-chlorophenyl)-4-methyl-2,3,4,5-tetrahydro-1H-benzo[e][1,4]diazepin-7-yl)thiazole;
2-(1-(4-chlorophenyl)-4-methyl-2,3,4,5-tetrahydro-1H-benzo[e][1,4]diazepin-7-yl)oxazole;
1-(4-chlorophenyl)-4-methyl-7-(1H-pyrazol-1-yl)-2,3,4,5-tetrahydro-1H-benzo[e][1,4]diazepine;
1-(4-chlorophenyl)-4-methyl-7-(1H-pyrazol-4-yl)-2,3,4,5-tetrahydro-1H-benzo[e][1,4]diazepine;
2-(1-(4-chlorophenyl)-4-methyl-2,3,4,5-tetrahydro-1H-benzo[e][1,4]diazepin-7-yl)-1,3,4-oxadiazole;
2-(1-(4-chlorophenyl)-4-methyl-2,3,4,5-tetrahydro-1H-benzo[e][1,4]diazepin-7-yl)-1,3,4-thiadiazole;
5-(1-(4-chlorophenyl)-4-methyl-2,3,4,5-tetrahydro-1H-benzo[e][1,4]diazepin-7-yl)-1,2,4-thiadiazole;
1-(4-chlorophenyl)-4-methyl-7-(1H-1,2,4-triazol-1-yl)-2,3,4,5-tetrahydro-1H-benzo[e][1,4]diazepine;
2-(1-(3,5-difluorophenyl)-4-methyl-2,3,4,5-tetrahydro-1H-benzo[e][1,4]diazepin-7-yl)oxazole;
2-(1-(3,5-difluorophenyl)-4-methyl-2,3,4,5-tetrahydro-1H-benzo[e][1,4]diazepin-7-yl)thiazole;
1-(3,5-difluorophenyl)-4-methyl-7-(1H-pyrazol-1-yl)-2,3,4,5-tetrahydro-1H-benzo[e][1,4]diazepine;
1-(3,5-difluorophenyl)-4-methyl-7-(1H-pyrazol-4-yl)-2,3,4,5-tetrahydro-1H-benzo[e][1,4]diazepine;
2-(1-(3,5-difluorophenyl)-4-methyl-2,3,4,5-tetrahydro-1H-benzo[e][1,4]diazepin-7-yl)-1,3,4-oxadiazole;
2-(1-(3,5-difluorophenyl)-4-methyl-2,3,4,5-tetrahydro-1H-benzo[e][1,4]diazepin-7-yl)-1,3,4-thiadiazole;
5-(1-(3,5-difluorophenyl)-4-methyl-2,3,4,5-tetrahydro-1H-benzo[e][1,4]diazepin-7-yl)-1,2,4-thiadiazole;
1-(3,5-difluorophenyl)-4-methyl-7-(1H-1,2,4-triazol-1-yl)-2,3,4,5-tetrahydro-1H-benzo[e][1,4]diazepine;
2-(1-(3,4-difluorophenyl)-4-methyl-2,3,4,5-tetrahydro-1H-benzo[e][1,4]diazepin-7-yl)oxazole;
2-(1-(3,4-difluorophenyl)-4-methyl-2,3,4,5-tetrahydro-1H-benzo[e][1,4]diazepin-7-yl)thiazole;
1-(3,4-difluorophenyl)-4-methyl-7-(1H-pyrazol-1-yl)-2,3,4,5-tetrahydro-1H-benzo[e][1,4]diazepine;
1-(3,4-difluorophenyl)-4-methyl-7-(1H-pyrazol-4-yl)-2,3,4,5-tetrahydro-1H-benzo[e][1,4]diazepine;
2-(1-(3,4-difluorophenyl)-4-methyl-2,3,4,5-tetrahydro-1H-benzo[e][1,4]diazepin-7-yl)-1,3,4-oxadiazole;
2-(1-(3,4-difluorophenyl)-4-methyl-2,3,4,5-tetrahydro-1H-benzo[e][1,4]diazepin-7-yl)-1,3,4-thiadiazole;
5-(1-(3,4-difluorophenyl)-4-methyl-2,3,4,5-tetrahydro-1H-benzo[e][1,4]diazepin-7-yl)-1,2,4-thiadiazole;
1-(3,4-difluorophenyl)-4-methyl-7-(1H-1,2,4-triazol-1-yl)-2,3,4,5-tetrahydro-1H-benzo[e][1,4]diazepine;
2-(4-methyl-1-(naphthalen-2-yl)-2,3,4,5-tetrahydro-1H-benzo[e][1,4]diazepin-7-yl)oxazole;
2-(4-methyl-1-(naphthalen-2-yl)-2,3,4,5-tetrahydro-1H-benzo[e][1,4]diazepin-7-yl)thiazole;
4-methyl-1-(naphthalen-2-yl)-7-(1H-pyrazol-1-yl)-2,3,4,5-tetrahydro-1H-benzo[e][1,4]diazepine;
4-methyl-1-(naphthalen-2-yl)-7-(1H-pyrazol-4-yl)-2,3,4,5-tetrahydro-1H-benzo[e][1,4]diazepine;
2-(4-methyl-1-(naphthalen-2-yl)-2,3,4,5-tetrahydro-1H-benzo[e][1,4]diazepin-7-yl)-1,3,4-oxadiazole;
2-(4-methyl-1-(naphthalen-2-yl)-2,3,4,5-tetrahydro-1H-benzo[e][1,4]diazepin-7-yl)-1,3,4-thiadiazole;
5-(4-methyl-1-(naphthalen-2-yl)-2,3,4,5-tetrahydro-1H-benzo[e][1,4]diazepin-7-yl)-1,2,4-thiadiazole;
4-methyl-1-(naphthalen-2-yl)-7-(1H-1,2,4-triazol-1-yl)-2,3,4,5-tetrahydro-1H-benzo[e][1,4]diazepine;
4-methyl-1-phenyl-7-(pyridin-2-yl)-2,3,4,5-tetrahydro-1H-benzo[e][1,4]diazepine;
4-methyl-1-phenyl-7-(pyridin-3-yl)-2,3,4,5-tetrahydro-1H-benzo[e][1,4]diazepine;
4-methyl-1-phenyl-7-(pyridin-4-yl)-2,3,4,5-tetrahydro-1H-benzo[e][1,4]diazepine;
6-(4-methyl-1-phenyl-2,3,4,5-tetrahydro-1H-benzo[e][1,4]diazepin-7-yl)pyridin-2-amine;
4-methyl-1-phenyl-7-(pyridazin-3-yl)-2,3,4,5-tetrahydro-1H-benzo[e][1,4]diazepine;
4-methyl-7-(6-methylpyridazin-3-yl)-1-phenyl-2,3,4,5-tetrahydro-1H-benzo[e][1,4]diazepine;
(6-(4-methyl-1-phenyl-2,3,4,5-tetrahydro-1H-benzo[e][1,4]diazepin-7-yl)pyridazin-3-yl)methanol;
6-(4-methyl-1-phenyl-2,3,4,5-tetrahydro-1H-benzo[e][1,4]diazepin-7-yl)pyridazin-3-amine;
4-methyl-1-phenyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-4-methyl-1-phenyl-2,3,4,5-tetrahydro-1H-benzo[e][1,4]diazepine;
7-(6-(difluoromethoxy)pyridazin-3-yl)-4-methyl-1-phenyl-2,3,4,5-tetrahydro-1H-benzo[e][1,4]diazepine;
4-methyl-1-phenyl-7-(pyrimidin-2-yl)-2,3,4,5-tetrahydro-1H-benzo[e][1,4]diazepine;
4-methyl-1-phenyl-7-(pyrimidin-5-yl)-2,3,4,5-tetrahydro-1H-benzo[e][1,4]diazepine;
4-methyl-1-phenyl-7-(pyrazin-2-yl)-2,3,4,5-tetrahydro-1H-benzo[e][1,4]diazepine;
6-(4-methyl-1-phenyl-2,3,4,5-tetrahydro-1H-benzo[e][1,4]diazepin-7-yl)pyridazin-3(2H)-one;
2-(4-methyl-1-phenyl-2,3,4,5-tetrahydro-1H-benzo[e][1,4]diazepin-7-yl)pyridazin-3(2H)-one;
1-(4-methyl-1-phenyl-2,3,4,5-tetrahydro-1H-benzo[e][1,4]diazepin-7-yl)pyridin-2(1H)-one;
6-(4-methyl-1-phenyl-2,3,4,5-tetrahydro-1H-benzo[e][1,4]diazepin-7-yl)pyridin-2(1H)-one;
4-methyl-1-(4-(methylsulfonyl)phenyl)-7-(pyridazin-3-yl)-2,3,4,5-tetrahydro-1H-benzo[e][1,4]diazepine;
3-(4-methyl-7-(pyridazin-3-yl)-2,3,4,5-tetrahydro-1H-benzo[e][1,4]diazepin-1-yl)benzonitrile;
4-methyl-7-(pyridazin-3-yl)-1-(3-(trifluoromethyl)phenyl)-2,3,4,5-tetrahydro-1H-benzo[e][1,4]diazepine;
1-(4-fluorophenyl)-4-methyl-7-(pyridin-2-yl)-2,3,4,5-tetrahydro-1H-benzo[e][1,4]diazepine;
1-(4-fluorophenyl)-4-methyl-7-(pyridin-3-yl)-2,3,4,5-tetrahydro-1H-benzo[e][1,4]diazepine;
1-(4-fluorophenyl)-4-methyl-7-(pyridin-4-yl)-2,3,4,5-tetrahydro-1H-benzo[e][1,4]diazepine;
6-(1-(4-fluorophenyl)-4-methyl-2,3,4,5-tetrahydro-1H-benzo[e][1,4]diazepin-7-yl)pyridin-2-amine;
1-(4-fluorophenyl)-4-methyl-7-(pyridazin-3-yl)-2,3,4,5-tetrahydro-1H-benzo[e][1,4]diazepine;
1-(4-fluorophenyl)-4-methyl-7-(6-methylpyridazin-3-yl)-2,3,4,5-tetrahydro-1H-benzo[e][1,4]diazepine;
(6-(1-(4-fluorophenyl)-4-methyl-2,3,4,5-tetrahydro-1H-benzo[e][1,4]diazepin-7-yl)pyridazin-3-yl)methanol;
6-(1-(4-fluorophenyl)-4-methyl-2,3,4,5-tetrahydro-1H-benzo[e][1,4]diazepin-7-yl)pyridazin-3-amine;
1-(4-fluorophenyl)-4-methyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-1-(4-fluorophenyl)-4-methyl-2,3,4,5-tetrahydro-1H-benzo[e][1,4]diazepine;
7-(6-(difluoromethoxy)pyridazin-3-yl)-1-(4-fluorophenyl)-4-methyl-2,3,4,5-tetrahydro-1H-benzo[e][1,4]diazepine;
1-(4-fluorophenyl)-4-methyl-7-(pyrazin-2-yl)-2,3,4,5-tetrahydro-1H-benzo[e][1,4]diazepine;

1-(4-fluorophenyl)-4-methyl-7-(pyrimidin-2-yl)-2,3,4,5-tetrahydro-1H-benzo[e][1,4]diazepine;
1-(4-fluorophenyl)-4-methyl-7-(pyrimidin-5-yl)-2,3,4,5-tetrahydro-1H-benzo[e][1,4]diazepine;
6-(1-(4-fluorophenyl)-4-methyl-2,3,4,5-tetrahydro-1H-benzo[e][1,4]diazepin-7-yl)pyridin-2(1H)-one;
1-(1-(4-fluorophenyl)-4-methyl-2,3,4,5-tetrahydro-1H-benzo[e][1,4]diazepin-8-yl)pyridin-2(1H)-one;
2-(1-(4-fluorophenyl)-4-methyl-2,3,4,5-tetrahydro-1H-benzo[e][1,4]diazepin-8-yl)pyridazin-3(2H)-one;
6-(1-(4-fluorophenyl)-4-methyl-2,3,4,5-tetrahydro-1H-benzo[e][1,4]diazepin-8-yl)pyridazin-3(2H)-one;
1-(3-fluorophenyl)-4-methyl-7-(pyridin-2-yl)-2,3,4,5-tetrahydro-1H-benzo[e][1,4]diazepine;
1-(3-fluorophenyl)-4-methyl-7-(pyridin-3-yl)-2,3,4,5-tetrahydro-1H-benzo[e][1,4]diazepine;
1-(3-fluorophenyl)-4-methyl-7-(pyridin-4-yl)-2,3,4,5-tetrahydro-1H-benzo[e][1,4]diazepine;
6-(1-(3-fluorophenyl)-4-methyl-2,3,4,5-tetrahydro-1H-benzo[e][1,4]diazepin-7-yl)pyridin-2-amine;
1-(3-fluorophenyl)-4-methyl-7-(pyridazin-3-yl)-2,3,4,5-tetrahydro-1H-benzo[e][1,4]diazepine;
1-(3-fluorophenyl)-4-methyl-7-(6-methylpyridazin-3-yl)-2,3,4,5-tetrahydro-1H-benzo[e][1,4]diazepine;
(6-(1-(3-fluorophenyl)-4-methyl-2,3,4,5-tetrahydro-1H-benzo[e][1,4]diazepin-7-yl)pyridazin-3-yl)methanol;
6-(1-(3-fluorophenyl)-4-methyl-2,3,4,5-tetrahydro-1H-benzo[e][1,4]diazepin-7-yl)pyridazin-3-amine;
1-(3-fluorophenyl)-4-methyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-1-(3-fluorophenyl)-4-methyl-2,3,4,5-tetrahydro-1H-benzo[e][1,4]diazepine;
7-(6-(difluoromethoxy)pyridazin-3-yl)-1-(3-fluorophenyl)-4-methyl-2,3,4,5-tetrahydro-1H-benzo[e][1,4]diazepine;
1-(3-fluorophenyl)-4-methyl-7-(pyrazin-2-yl)-2,3,4,5-tetrahydro-1H-benzo[e][1,4]diazepine;
1-(3-fluorophenyl)-4-methyl-7-(pyrimidin-2-yl)-2,3,4,5-tetrahydro-1H-benzo[e][1,4]diazepine;
1-(3-fluorophenyl)-4-methyl-7-(pyrimidin-5-yl)-2,3,4,5-tetrahydro-1H-benzo[e][1,4]diazepine;
6-(1-(3-fluorophenyl)-4-methyl-2,3,4,5-tetrahydro-1H-benzo[e][1,4]diazepin-7-yl)pyridin-2(1H)-one;
1-(1-(3-fluorophenyl)-4-methyl-2,3,4,5-tetrahydro-1H-benzo[e][1,4]diazepin-8-yl)pyridin-2(1H)-one;
2-(1-(3-fluorophenyl)-4-methyl-2,3,4,5-tetrahydro-1H-benzo[e][1,4]diazepin-8-yl)pyridazin-3(2H)-one;
6-(1-(3-fluorophenyl)-4-methyl-2,3,4,5-tetrahydro-1H-benzo[e][1,4]diazepin-8-yl)pyridazin-3(2H)-one;
1-(2-fluorophenyl)-4-methyl-7-(pyridin-2-yl)-2,3,4,5-tetrahydro-1H-benzo[e][1,4]diazepine;
1-(2-fluorophenyl)-4-methyl-7-(pyridin-3-yl)-2,3,4,5-tetrahydro-1H-benzo[e][1,4]diazepine;
1-(2-fluorophenyl)-4-methyl-7-(pyridin-4-yl)-2,3,4,5-tetrahydro-1H-benzo[e][1,4]diazepine;
6-(1-(2-fluorophenyl)-4-methyl-2,3,4,5-tetrahydro-1H-benzo[e][1,4]diazepin-7-yl)pyridin-2-amine;
1-(2-fluorophenyl)-4-methyl-7-(pyridazin-3-yl)-2,3,4,5-tetrahydro-1H-benzo[e][1,4]diazepine;
1-(2-fluorophenyl)-4-methyl-7-(6-methylpyridazin-3-yl)-2,3,4,5-tetrahydro-1H-benzo[e][1,4]diazepine;
(6-(1-(2-fluorophenyl)-4-methyl-2,3,4,5-tetrahydro-1H-benzo[e][1,4]diazepin-7-yl)pyridazin-3-yl)methanol;
6-(1-(2-fluorophenyl)-4-methyl-2,3,4,5-tetrahydro-1H-benzo[e][1,4]diazepin-7-yl)pyridazin-3-amine;
1-(2-fluorophenyl)-4-methyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-1-(2-fluorophenyl)-4-methyl-2,3,4,5-tetrahydro-1H-benzo[e][1,4]diazepine;
7-(6-(difluoromethoxy)pyridazin-3-yl)-1-(2-fluorophenyl)-4-methyl-2,3,4,5-tetrahydro-1H-benzo[e][1,4]diazepine;
1-(2-fluorophenyl)-4-methyl-7-(pyrazin-2-yl)-2,3,4,5-tetrahydro-1H-benzo[e][1,4]diazepine;
1-(2-fluorophenyl)-4-methyl-7-(pyrimidin-2-yl)-2,3,4,5-tetrahydro-1H-benzo[e][1,4]diazepine;
1-(2-fluorophenyl)-4-methyl-7-(pyrimidin-5-yl)-2,3,4,5-tetrahydro-1H-benzo[e][1,4]diazepine;
6-(1-(2-fluorophenyl)-4-methyl-2,3,4,5-tetrahydro-1H-benzo[e][1,4]diazepin-7-yl)pyridin-2(1H)-one;
1-(1-(2-fluorophenyl)-4-methyl-2,3,4,5-tetrahydro-1H-benzo[e][1,4]diazepin-8-yl)pyridin-2(1H)-one;
2-(1-(2-fluorophenyl)-4-methyl-2,3,4,5-tetrahydro-1H-benzo[e][1,4]diazepin-8-yl)pyridazin-3(2H)-one;
6-(1-(2-fluorophenyl)-4-methyl-2,3,4,5-tetrahydro-1H-benzo[e][1,4]diazepin-8-yl)pyridazin-3(2H)-one;
1-(4-chlorophenyl)-4-methyl-7-(pyridin-2-yl)-2,3,4,5-tetrahydro-1H-benzo[e][1,4]diazepine;
1-(4-chlorophenyl)-4-methyl-7-(pyridin-3-yl)-2,3,4,5-tetrahydro-1H-benzo[e][1,4]diazepine;
1-(4-chlorophenyl)-4-methyl-7-(pyridin-4-yl)-2,3,4,5-tetrahydro-1H-benzo[e][1,4]diazepine;
6-(1-(4-chlorophenyl)-4-methyl-2,3,4,5-tetrahydro-1H-benzo[e][1,4]diazepin-7-yl)pyridin-2-amine;
1-(4-chlorophenyl)-4-methyl-7-(pyridazin-3-yl)-2,3,4,5-tetrahydro-1H-benzo[e][1,4]diazepine;
1-(4-chlorophenyl)-4-methyl-7-(6-methylpyridazin-3-yl)-2,3,4,5-tetrahydro-1H-benzo[e][1,4]diazepine;
(6-(1-(4-chlorophenyl)-4-methyl-2,3,4,5-tetrahydro-1H-benzo[e][1,4]diazepin-7-yl)pyridazin-3-yl)methanol;
6-(1-(4-chlorophenyl)-4-methyl-2,3,4,5-tetrahydro-1H-benzo[e][1,4]diazepin-7-yl)pyridazin-3-amine;
1-(4-chlorophenyl)-4-methyl-7-(6-(trifluoromethyl)pyridazin-3-yl)-2,3,4,5-tetrahydro-1H-benzo[e][1,4]diazepine;
1-(4-chlorophenyl)-7-(6-(difluoromethyl)pyridazin-3-yl)-4-methyl-2,3,4,5-tetrahydro-1H-benzo[e][1,4]diazepine;
1-(4-chlorophenyl)-7-(6-(difluoromethoxy)pyridazin-3-yl)-4-methyl-2,3,4,5-tetrahydro-1H-benzo[e][1,4]diazepine;
1-(4-chlorophenyl)-4-methyl-7-(pyrazin-2-yl)-2,3,4,5-tetrahydro-1H-benzo[e][1,4]diazepine;
1-(4-chlorophenyl)-4-methyl-7-(pyrimidin-2-yl)-2,3,4,5-tetrahydro-1H-benzo[e][1,4]diazepine;
1-(4-chlorophenyl)-4-methyl-7-(pyrimidin-5-yl)-2,3,4,5-tetrahydro-1H-benzo[e][1,4]diazepine;
6-(1-(4-chlorophenyl)-4-methyl-2,3,4,5-tetrahydro-1H-benzo[e][1,4]diazepin-7-yl)pyridin-2(1H)-one;
1-(1-(4-chlorophenyl)-4-methyl-2,3,4,5-tetrahydro-1H-benzo[e][1,4]diazepin-8-yl)pyridin-2(1H)-one;
2-(1-(4-chlorophenyl)-4-methyl-2,3,4,5-tetrahydro-1H-benzo[e][1,4]diazepin-8-yl)pyridazin-3(2H)-one;
6-(1-(4-chlorophenyl)-4-methyl-2,3,4,5-tetrahydro-1H-benzo[e][1,4]diazepin-8-yl)pyridazin-3(2H)-one;
1-(3-chlorophenyl)-4-methyl-7-(pyridin-2-yl)-2,3,4,5-tetrahydro-1H-benzo[e][1,4]diazepine;
1-(3-chlorophenyl)-4-methyl-7-(pyridin-3-yl)-2,3,4,5-tetrahydro-1H-benzo[e][1,4]diazepine;
1-(3-chlorophenyl)-4-methyl-7-(pyridin-4-yl)-2,3,4,5-tetrahydro-1H-benzo[e][1,4]diazepine;
6-(1-(3-chlorophenyl)-4-methyl-2,3,4,5-tetrahydro-1H-benzo[e][1,4]diazepin-7-yl)pyridin-2-amine;

1-(3-chlorophenyl)-4-methyl-7-(pyridazin-3-yl)-2,3,4,5-tetrahydro-1H-benzo[e][1,4]diazepine;
1-(3-chlorophenyl)-4-methyl-7-(6-methylpyridazin-3-yl)-2,3,4,5-tetrahydro-1H-benzo[e][1,4]diazepine;
(6-(1-(3-chlorophenyl)-4-methyl-2,3,4,5-tetrahydro-1H-benzo[e][1,4]diazepin-7-yl)pyridazin-3-yl)methanol;
6-(1-(3-chlorophenyl)-4-methyl-2,3,4,5-tetrahydro-1H-benzo[e][1,4]diazepin-7-yl)pyridazin-3-amine;
1-(3-chlorophenyl)-4-methyl-7-(6-(trifluoromethyl)pyridazin-3-yl)-2,3,4,5-tetrahydro-1H-benzo[e][1,4]diazepine;
1-(3-chlorophenyl)-7-(6-(difluoromethyl)pyridazin-3-yl)-4-methyl-2,3,4,5-tetrahydro-1H-benzo[e][1,4]diazepine;
1-(3-chlorophenyl)-7-(6-(difluoromethoxy)pyridazin-3-yl)-4-methyl-2,3,4,5-tetrahydro-1H-benzo[e][1,4]diazepine;
1-(3-chlorophenyl)-4-methyl-7-(pyrazin-2-yl)-2,3,4,5-tetrahydro-1H-benzo[e][1,4]diazepine;
1-(3-chlorophenyl)-4-methyl-7-(pyrimidin-2-yl)-2,3,4,5-tetrahydro-1H-benzo[e][1,4]diazepine;
1-(3-chlorophenyl)-4-methyl-7-(pyrimidin-5-yl)-2,3,4,5-tetrahydro-1H-benzo[e][1,4]diazepine;
6-(1-(3-chlorophenyl)-4-methyl-2,3,4,5-tetrahydro-1H-benzo[e][1,4]diazepin-7-yl)pyridin-2(1H)-one;
1-(1-(3-chlorophenyl)-4-methyl-2,3,4,5-tetrahydro-1H-benzo[e][1,4]diazepin-8-yl)pyridin-2(1H)-one;
2-(1-(3-chlorophenyl)-4-methyl-2,3,4,5-tetrahydro-1H-benzo[e][1,4]diazepin-8-yl)pyridazin-3(2H)-one;
6-(1-(3-chlorophenyl)-4-methyl-2,3,4,5-tetrahydro-1H-benzo[e][1,4]diazepin-8-yl)pyridazin-3(2H)-one;
1-(2-chlorophenyl)-4-methyl-7-(pyridin-2-yl)-2,3,4,5-tetrahydro-1H-benzo[e][1,4]diazepine;
1-(2-chlorophenyl)-4-methyl-7-(pyridin-3-yl)-2,3,4,5-tetrahydro-1H-benzo[e][1,4]diazepine;
1-(2-chlorophenyl)-4-methyl-7-(pyridin-4-yl)-2,3,4,5-tetrahydro-1H-benzo[e][1,4]diazepine;
6-(1-(2-chlorophenyl)-4-methyl-2,3,4,5-tetrahydro-1H-benzo[e][1,4]diazepin-7-yl)pyridin-2-amine;
1-(2-chlorophenyl)-4-methyl-7-(pyridazin-3-yl)-2,3,4,5-tetrahydro-1H-benzo[e][1,4]diazepine;
1-(2-chlorophenyl)-4-methyl-7-(6-methylpyridazin-3-yl)-2,3,4,5-tetrahydro-1H-benzo[e][1,4]diazepine;
(6-(1-(2-chlorophenyl)-4-methyl-2,3,4,5-tetrahydro-1H-benzo[e][1,4]diazepin-7-yl)pyridazin-3-yl)methanol;
6-(1-(2-chlorophenyl)-4-methyl-2,3,4,5-tetrahydro-1H-benzo[e][1,4]diazepin-7-yl)pyridazin-3-amine;
1-(2-chlorophenyl)-4-methyl-7-(6-(trifluoromethyl)pyridazin-3-yl)-2,3,4,5-tetrahydro-1H-benzo[e][1,4]diazepine;
1-(2-chlorophenyl)-7-(6-(difluoromethyl)pyridazin-3-yl)-4-methyl-2,3,4,5-tetrahydro-1H-benzo[e][1,4]diazepine;
1-(2-chlorophenyl)-7-(6-(difluoromethoxy)pyridazin-3-yl)-4-methyl-2,3,4,5-tetrahydro-1H-benzo[e][1,4]diazepine;
1-(2-chlorophenyl)-4-methyl-7-(pyrazin-2-yl)-2,3,4,5-tetrahydro-1H-benzo[e][1,4]diazepine;
1-(2-chlorophenyl)-4-methyl-7-(pyrimidin-2-yl)-2,3,4,5-tetrahydro-1H-benzo[e][1,4]diazepine;
1-(2-chlorophenyl)-4-methyl-7-(pyrimidin-5-yl)-2,3,4,5-tetrahydro-1H-benzo[e][1,4]diazepine;
6-(1-(2-chlorophenyl)-4-methyl-2,3,4,5-tetrahydro-1H-benzo[e][1,4]diazepin-7-yl)pyridin-2(1H)-one;
1-(1-(2-chlorophenyl)-4-methyl-2,3,4,5-tetrahydro-1H-benzo[e][1,4]diazepin-8-yl)pyridin-2(1H)-one;
2-(1-(2-chlorophenyl)-4-methyl-2,3,4,5-tetrahydro-1H-benzo[e][1,4]diazepin-8-yl)pyridazin-3(2H)-one;
6-(1-(2-chlorophenyl)-4-methyl-2,3,4,5-tetrahydro-1H-benzo[e][1,4]diazepin-8-yl)pyridazin-3(2H)-one;
1-(3,5-difluorophenyl)-4-methyl-7-(pyridin-2-yl)-2,3,4,5-tetrahydro-1H-benzo[e][1,4]diazepine;
1-(3,5-difluorophenyl)-4-methyl-7-(pyridin-3-yl)-2,3,4,5-tetrahydro-1H-benzo[e][1,4]diazepine;
1-(3,5-difluorophenyl)-4-methyl-7-(pyridin-4-yl)-2,3,4,5-tetrahydro-1H-benzo[e][1,4]diazepine;
6-(1-(3,5-difluorophenyl)-4-methyl-2,3,4,5-tetrahydro-1H-benzo[e][1,4]diazepin-7-yl)pyridin-2-amine;
1-(3,5-difluorophenyl)-4-methyl-7-(pyridazin-3-yl)-2,3,4,5-tetrahydro-1H-benzo[e][1,4]diazepine;
1-(3,5-difluorophenyl)-4-methyl-7-(6-methylpyridazin-3-yl)-2,3,4,5-tetrahydro-1H-benzo[e][1,4]diazepine;
(6-(1-(3,5-difluorophenyl)-4-methyl-2,3,4,5-tetrahydro-1H-benzo[e][1,4]diazepin-7-yl)pyridazin-3-yl)methanol;
6-(1-(3,5-difluorophenyl)-4-methyl-2,3,4,5-tetrahydro-1H-benzo[e][1,4]diazepin-7-yl)pyridazin-3-amine;
1-(3,5-difluorophenyl)-4-methyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-1-(3,5-difluorophenyl)-4-methyl-2,3,4,5-tetrahydro-1H-benzo[e][1,4]diazepine;
7-(6-(difluoromethyl)pyridazin-3-yl)-1-(3,5-difluorophenyl)-4-methyl-2,3,4,5-tetrahydro-1H-benzo[e][1,4]diazepine;
1-(3,5-difluorophenyl)-4-methyl-7-(pyrimidin-2-yl)-2,3,4,5-tetrahydro-1H-benzo[e][1,4]diazepine;
1-(3,5-difluorophenyl)-4-methyl-7-(pyrimidin-5-yl)-2,3,4,5-tetrahydro-1H-benzo[e][1,4]diazepine;
1-(3,5-difluorophenyl)-4-methyl-7-(pyrazin-2-yl)-2,3,4,5-tetrahydro-1H-benzo[e][1,4]diazepine;
1-(1-(3,5-difluorophenyl)-4-methyl-2,3,4,5-tetrahydro-1H-benzo[e][1,4]diazepin-7-yl)pyridin-2(1H)-one;
6-(1-(3,5-difluorophenyl)-4-methyl-2,3,4,5-tetrahydro-1H-benzo[e][1,4]diazepin-8-yl)pyridin-2(1H)-one;
6-(1-(3,5-difluorophenyl)-4-methyl-2,3,4,5-tetrahydro-1H-benzo[e][1,4]diazepin-7-yl)pyridazin-3(2H)-one;
2-(1-(3,5-difluorophenyl)-4-methyl-2,3,4,5-tetrahydro-1H-benzo[e][1,4]diazepin-7-yl)pyridazin-3(2H)-one;
1-(3,4-difluorophenyl)-4-methyl-7-(pyridin-2-yl)-2,3,4,5-tetrahydro-1H-benzo[e][1,4]diazepine;
1-(3,4-difluorophenyl)-4-methyl-7-(pyridin-3-yl)-2,3,4,5-tetrahydro-1H-benzo[e][1,4]diazepine;
1-(3,4-difluorophenyl)-4-methyl-7-(pyridin-4-yl)-2,3,4,5-tetrahydro-1H-benzo[e][1,4]diazepine;
6-(1-(3,4-difluorophenyl)-4-methyl-2,3,4,5-tetrahydro-1H-benzo[e][1,4]diazepin-7-yl)pyridin-2-amine;
1-(3,4-difluorophenyl)-4-methyl-7-(pyridazin-3-yl)-2,3,4,5-tetrahydro-1H-benzo[e][1,4]diazepine;
1-(3,4-difluorophenyl)-4-methyl-7-(6-methylpyridazin-3-yl)-2,3,4,5-tetrahydro-1H-benzo[e][1,4]diazepine;
(6-(1-(3,4-difluorophenyl)-4-methyl-2,3,4,5-tetrahydro-1H-benzo[e][1,4]diazepin-7-yl)pyridazin-3-yl)methanol;
6-(1-(3,4-difluorophenyl)-4-methyl-2,3,4,5-tetrahydro-1H-benzo[e][1,4]diazepin-7-yl)pyridazin-3-amine;
1-(3,4-difluorophenyl)-4-methyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-1-(3,4-difluorophenyl)-4-methyl-2,3,4,5-tetrahydro-1H-benzo[e][1,4]diazepine;
7-(6-(difluoromethyl)pyridazin-3-yl)-1-(3,4-difluorophenyl)-4-methyl-2,3,4,5-tetrahydro-1H-benzo[e][1,4]diazepine;
1-(3,4-difluorophenyl)-4-methyl-7-(pyrimidin-2-yl)-2,3,4,5-tetrahydro-1H-benzo[e][1,4]diazepine;

1-(3,4-difluorophenyl)-4-methyl-7-(pyrimidin-5-yl)-2,3,4,5-tetrahydro-1H-benzo[e][1,4]diazepine;
1-(3,4-difluorophenyl)-4-methyl-7-(pyrazin-2-yl)-2,3,4,5-tetrahydro-1H-benzo[e][1,4]diazepine;
1-(1-(3,4-difluorophenyl)-4-methyl-2,3,4,5-tetrahydro-1H-benzo[e][1,4]diazepin-7-yl)pyridin-2(1H)-one;
6-(1-(3,4-difluorophenyl)-4-methyl-2,3,4,5-tetrahydro-1H-benzo[e][1,4]diazepin-8-yl)pyridin-2(1H)-one;
6-(1-(3,4-difluorophenyl)-4-methyl-2,3,4,5-tetrahydro-1H-benzo[e][1,4]diazepin-7-yl)pyridazin-3(2H)-one;
2-(1-(3,4-difluorophenyl)-4-methyl-2,3,4,5-tetrahydro-1H-benzo[e][1,4]diazepin-7-yl)pyridazin-3(2H)-one;
1-(3,4-dichlorophenyl)-4-methyl-7-(pyridin-2-yl)-2,3,4,5-tetrahydro-1H-benzo[e][1,4]diazepine;
1-(3,4-dichlorophenyl)-4-methyl-7-(pyridin-3-yl)-2,3,4,5-tetrahydro-1H-benzo[e][1,4]diazepine;
1-(3,4-dichlorophenyl)-4-methyl-7-(pyridin-4-yl)-2,3,4,5-tetrahydro-1H-benzo[e][1,4]diazepine;
6-(1-(3,4-dichlorophenyl)-4-methyl-2,3,4,5-tetrahydro-1H-benzo[e][1,4]diazepin-7-yl)pyridin-2-amine;
1-(3,4-dichlorophenyl)-4-methyl-7-(pyridazin-3-yl)-2,3,4,5-tetrahydro-1H-benzo[e][1,4]diazepine;
1-(3,4-dichlorophenyl)-4-methyl-7-(6-methylpyridazin-3-yl)-2,3,4,5-tetrahydro-1H-benzo[e][1,4]diazepine;
(6-(1-(3,4-dichlorophenyl)-4-methyl-2,3,4,5-tetrahydro-1H-benzo[e][1,4]diazepin-7-yl)pyridazin-3-yl)methanol;
6-(1-(3,4-dichlorophenyl)-4-methyl-2,3,4,5-tetrahydro-1H-benzo[e][1,4]diazepin-7-yl)pyridazin-3-amine;
1-(3,5-dichlorophenyl)-4-methyl-7-(6-(trifluoromethyl)pyridazin-3-yl)-2,3,4,5-tetrahydro-1H-benzo[e][1,4]diazepine;
1-(3,4-dichlorophenyl)-7-(6-(difluoromethyl)pyridazin-3-yl)-4-methyl-2,3,4,5-tetrahydro-1H-benzo[e][1,4]diazepine;
1-(3,4-dichlorophenyl)-7-(6-(difluoromethoxy)pyridazin-3-yl)-4-methyl-2,3,4,5-tetrahydro-1H-benzo[e][1,4]diazepine;
1-(3,4-dichlorophenyl)-4-methyl-7-(pyrimidin-2-yl)-2,3,4,5-tetrahydro-1H-benzo[e][1,4]diazepine;
1-(3,4-dichlorophenyl)-4-methyl-7-(pyrimidin-5-yl)-2,3,4,5-tetrahydro-1H-benzo[e][1,4]diazepine;
1-(3,4-dichlorophenyl)-4-methyl-7-(pyrazin-2-yl)-2,3,4,5-tetrahydro-1H-benzo[e][1,4]diazepine;
1-(1-(3,4-dichlorophenyl)-4-methyl-2,3,4,5-tetrahydro-1H-benzo[e][1,4]diazepin-7-yl)pyridin-2(1H)-one;
6-(1-(3,4-dichlorophenyl)-4-methyl-2,3,4,5-tetrahydro-1H-benzo[e][1,4]diazepin-8-yl)pyridin-2(1H)-one;
6-(1-(3,4-dichlorophenyl)-4-methyl-2,3,4,5-tetrahydro-1H-benzo[e][1,4]diazepin-7-yl)pyridazin-3(2H)-one;
2-(1-(3,4-dichlorophenyl)-4-methyl-2,3,4,5-tetrahydro-1H-benzo[e][1,4]diazepin-7-yl)pyridazin-3(2H)-one;
7-(4-(ethylsulfonyl)piperazin-1-yl)-4-methyl-1-(naphthalen-2-yl)-2,3,4,5-tetrahydro-1H-benzo[e][1,4]diazepine;
4-methyl-1-(naphthalen-2-yl)-7-(pyridin-2-yl)-2,3,4,5-tetrahydro-1H-benzo[e][1,4]diazepine;
4-methyl-1-(naphthalen-2-yl)-7-(pyridin-3-yl)-2,3,4,5-tetrahydro-1H-benzo[e][1,4]diazepine;
4-methyl-1-(naphthalen-2-yl)-7-(pyridin-4-yl)-2,3,4,5-tetrahydro-1H-benzo[e][1,4]diazepine;
6-(4-methyl-1-(naphthalen-2-yl)-2,3,4,5-tetrahydro-1H-benzo[e][1,4]diazepin-7-yl)pyridin-2-amine;
4-methyl-1-(naphthalen-1-yl)-7-(pyridazin-3-yl)-2,3,4,5-tetrahydro-1H-benzo[e][1,4]diazepine;
4-methyl-1-(naphthalen-2-yl)-7-(pyridazin-3-yl)-2,3,4,5-tetrahydro-1H-benzo[e][1,4]diazepine;
4-methyl-7-(6-methylpyridazin-3-yl)-1-(naphthalen-2-yl)-2,3,4,5-tetrahydro-1H-benzo[e][1,4]diazepine;
(6-(4-methyl-1-(naphthalen-2-yl)-2,3,4,5-tetrahydro-1H-benzo[e][1,4]diazepin-7-yl)pyridazin-3-yl)methanol;
6-(4-methyl-1-(naphthalen-2-yl)-2,3,4,5-tetrahydro-1H-benzo[e][1,4]diazepin-7-yl)pyridazin-3-amine;
4-methyl-1-(naphthalen-2-yl)-7-(6-(trifluoromethyl)pyridazin-3-yl)-2,3,4,5-tetrahydro-1H-benzo[e][1,4]diazepine;
7-(6-(difluoromethyl)pyridazin-3-yl)-4-methyl-1-(naphthalen-2-yl)-2,3,4,5-tetrahydro-1H-benzo[e][1,4]diazepine;
7-(6-(difluoromethoxy)pyridazin-3-yl)-4-methyl-1-(naphthalen-2-yl)-2,3,4,5-tetrahydro-1H-benzo[e][1,4]diazepine;
4-methyl-1-(naphthalen-2-yl)-7-(pyrimidin-2-yl)-2,3,4,5-tetrahydro-1H-benzo[e][1,4]diazepine;
4-methyl-1-(naphthalen-2-yl)-7-(pyrimidin-5-yl)-2,3,4,5-tetrahydro-1H-benzo[e][1,4]diazepine;
4-methyl-1-(naphthalen-2-yl)-N-(pyrimidin-2-yl)-2,3,4,5-tetrahydro-1H-benzo[e][1,4]diazepin-7-amine;
4-methyl-1-(naphthalen-2-yl)-7-(pyrazin-2-yl)-2,3,4,5-tetrahydro-1H-benzo[e][1,4]diazepine;
6-(4-methyl-1-(naphthalen-2-yl)-2,3,4,5-tetrahydro-1H-benzo[e][1,4]diazepin-7-yl)pyridin-2(1H)-one;
1-(4-methyl-1-(naphthalen-2-yl)-2,3,4,5-tetrahydro-1H-benzo[e][1,4]diazepin-7-yl)pyridin-2(1H)-one;
2-(4-methyl-1-(naphthalen-2-yl)-2,3,4,5-tetrahydro-1H-benzo[e][1,4]diazepin-7-yl)pyridazin-3(2H)-one;
6-(4-methyl-1-(naphthalen-2-yl)-2,3,4,5-tetrahydro-1H-benzo[e][1,4]diazepin-7-yl)pyridazin-3(2H)-one;
1-(1-fluoronaphthalen-2-yl)-4-methyl-7-(pyridin-3-yl)-2,3,4,5-tetrahydro-1H-benzo[e][1,4]diazepine;
1-(1-fluoronaphthalen-2-yl)-4-methyl-7-(6-methylpyridazin-3-yl)-2,3,4,5-tetrahydro-1H-benzo[e][1,4]diazepine;
(6-(1-(1-fluoronaphthalen-2-yl)-4-methyl-2,3,4,5-tetrahydro-1H-benzo[e][1,4]diazepin-7-yl)pyridazin-3-yl)methanol;
1-(1-fluoronaphthalen-2-yl)-4-methyl-7-(pyrimidin-2-yl)-2,3,4,5-tetrahydro-1H-benzo[e][1,4]diazepine;
1-(1-fluoronaphthalen-2-yl)-4-methyl-7-(pyrimidin-5-yl)-2,3,4,5-tetrahydro-1H-benzo[e][1,4]diazepine;
1-(1-fluoronaphthalen-2-yl)-4-methyl-7-(pyrazin-2-yl)-2,3,4,5-tetrahydro-1H-benzo[e][1,4]diazepine;
1-(1-(1-fluoronaphthalen-2-yl)-4-methyl-2,3,4,5-tetrahydro-1H-benzo[e][1,4]diazepin-7-yl)pyridin-2(1H)-one;
6-(1-(1-fluoronaphthalen-2-yl)-4-methyl-2,3,4,5-tetrahydro-1H-benzo[e][1,4]diazepin-7-yl)pyridin-2(1H)-one;
6-(1-(1-fluoronaphthalen-2-yl)-4-methyl-2,3,4,5-tetrahydro-1H-benzo[e][1,4]diazepin-7-yl)pyridazin-3(2H)-one;
2-(1-(1-fluoronaphthalen-2-yl)-4-methyl-2,3,4,5-tetrahydro-1H-benzo[e][1,4]diazepin-7-yl)pyridazin-3(2H)-one;
1-(4-fluoronaphthalen-2-yl)-4-methyl-7-(pyridazin-3-yl)-2,3,4,5-tetrahydro-1H-benzo[e][1,4]diazepine;
1-(4-fluoronaphthalen-2-yl)-4-methyl-7-(6-methylpyridazin-3-yl)-2,3,4,5-tetrahydro-1H-benzo[e][1,4]diazepine;
(6-(4-(1-fluoronaphthalen-2-yl)-4-methyl-2,3,4,5-tetrahydro-1H-benzo[e][1,4]diazepin-7-yl)pyridazin-3-yl)methanol;
1-(4-fluoronaphthalen-2-yl)-4-methyl-7-(pyrimidin-2-yl)-2,3,4,5-tetrahydro-1H-benzo[e][1,4]diazepine;
1-(4-fluoronaphthalen-2-yl)-4-methyl-7-(pyrimidin-5-yl)-2,3,4,5-tetrahydro-1H-benzo[e][1,4]diazepine;
1-(4-fluoronaphthalen-2-yl)-4-methyl-7-(pyrazin-2-yl)-2,3,4,5-tetrahydro-1H-benzo[e][1,4]diazepine;
1-(1-(4-fluoronaphthalen-2-yl)-4-methyl-2,3,4,5-tetrahydro-1H-benzo[e][1,4]diazepin-7-yl)pyridin-2(1H)-one;
6-(1-(4-fluoronaphthalen-2-yl)-4-methyl-2,3,4,5-tetrahydro-1H-benzo[e][1,4]diazepin-7-yl)pyridin-2(1H)-one;
6-(1-(4-fluoronaphthalen-2-yl)-4-methyl-2,3,4,5-tetrahydro-1H-benzo[e][1,4]diazepin-7-yl)pyridazin-3(2H)-one;
2-(1-(4-fluoronaphthalen-2-yl)-4-methyl-2,3,4,5-tetrahydro-1H-benzo[e][1,4]diazepin-7-yl)pyridazin-3(2H)-one;

1-(5-fluoronaphthalen-2-yl)-4-methyl-7-(pyridazin-3-yl)-2,3,4,5-tetrahydro-1H-benzo[e][1,4]diazepine;
1-(5-fluoronaphthalen-2-yl)-4-methyl-7-(6-methylpyridazin-3-yl)-2,3,4,5-tetrahydro-1H-benzo[e][1,4]diazepine;
(6-(1-(5-fluoronaphthalen-2-yl)-4-methyl-2,3,4,5-tetrahydro-1H-benzo[e][1,4]diazepin-7-yl)pyridazin-3-yl)methanol;
1-(5-fluoronaphthalen-2-yl)-4-methyl-7-(pyrimidin-2-yl)-2,3,4,5-tetrahydro-1H-benzo[e][1,4]diazepine;
1-(5-fluoronaphthalen-2-yl)-4-methyl-7-(pyrimidin-5-yl)-2,3,4,5-tetrahydro-1H-benzo[e][1,4]diazepine;
1-(5-fluoronaphthalen-2-yl)-4-methyl-7-(pyrazin-2-yl)-2,3,4,5-tetrahydro-1H-benzo[e][1,4]diazepine;
1-(1-(5-fluoronaphthalen-2-yl)-4-methyl-2,3,4,5-tetrahydro-1H-benzo[e][1,4]diazepin-7-yl)pyridin-2(1H)-one;
6-(1-(5-fluoronaphthalen-2-yl)-4-methyl-2,3,4,5-tetrahydro-1H-benzo[e][1,4]diazepin-7-yl)pyridin-2(1H)-one;
6-(1-(5-fluoronaphthalen-2-yl)-4-methyl-2,3,4,5-tetrahydro-1H-benzo[e][1,4]diazepin-7-yl)pyridazin-3(2H)-one;
2-(1-(5-fluoronaphthalen-2-yl)-4-methyl-2,3,4,5-tetrahydro-1H-benzo[e][1,4]diazepin-7-yl)pyridazin-3(2H)-one;
1-(benzo[d][1,3]dioxol-5-yl)-4-methyl-7-(pyridazin-3-yl)-2,3,4,5-tetrahydro-1H-benzo[e][1,4]diazepine;
1-(benzo[b]thiophen-2-yl)-4-methyl-7-(pyridazin-3-yl)-2,3,4,5-tetrahydro-1H-benzo[e][1,4]diazepine;
1-(benzofuran-2-yl)-4-methyl-7-(pyridazin-3-yl)-2,3,4,5-tetrahydro-1H-benzo[e][1,4]diazepine;
7-([1,2,4]triazolo[1,5-a]pyridin-6-yl)-4-methyl-1-phenyl-2,3,4,5-tetrahydro-1H-benzo[e][1,4]diazepine;
7-([1,2,4]triazolo[4,3-a]pyridin-6-yl)-4-methyl-1-phenyl-2,3,4,5-tetrahydro-1H-benzo[e][1,4]diazepine;
2-(4-methyl-1-phenyl-2,3,4,5-tetrahydro-1H-benzo[e][1,4]diazepin-7-yl)-[1,2,4]triazolo[4,3-a]pyridin-3(2H)-one;
4-methyl-1-phenyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(4-fluorophenyl)-4-methyl-2,3,4,5-tetrahydro-1H-benzo[e][1,4]diazepine;
7-([1,2,4]triazolo[4,3-a]pyridin-6-yl)-1-(4-fluorophenyl)-4-methyl-2,3,4,5-tetrahydro-1H-benzo[e][1,4]diazepine;
2-(1-(4-fluorophenyl)-4-methyl-2,3,4,5-tetrahydro-1H-benzo[e][1,4]diazepin-7-yl)-[1,2,4]triazolo[4,3-a]pyridin-3(2H)-one;
1-(4-fluorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(3-fluorophenyl)-4-methyl-2,3,4,5-tetrahydro-1H-benzo[e][1,4]diazepine;
7-([1,2,4]triazolo[4,3-a]pyridin-6-yl)-1-(3-fluorophenyl)-4-methyl-2,3,4,5-tetrahydro-1H-benzo[e][1,4]diazepine;
2-(1-(3-fluorophenyl)-4-methyl-2,3,4,5-tetrahydro-1H-benzo[e][1,4]diazepin-7-yl)-[1,2,4]triazolo[4,3-a]pyridin-3(2H)-one;
1-(3-fluorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(2-fluorophenyl)-4-methyl-2,3,4,5-tetrahydro-1H-benzo[e][1,4]diazepine;
7-([1,2,4]triazolo[4,3-a]pyridin-6-yl)-1-(2-fluorophenyl)-4-methyl-2,3,4,5-tetrahydro-1H-benzo[e][1,4]diazepine;
2-(1-(2-fluorophenyl)-4-methyl-2,3,4,5-tetrahydro-1H-benzo[e][1,4]diazepin-7-yl)-[1,2,4]triazolo[4,3-a]pyridin-3(2H)-one;
1-(2-fluorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(4-chlorophenyl)-4-methyl-2,3,4,5-tetrahydro-1H-benzo[e][1,4]diazepine;
7-([1,2,4]triazolo[4,3-a]pyridin-6-yl)-1-(4-chlorophenyl)-4-methyl-2,3,4,5-tetrahydro-1H-benzo[e][1,4]diazepine;
2-(1-(4-chlorophenyl)-4-methyl-2,3,4,5-tetrahydro-1H-benzo[e][1,4]diazepin-7-yl)-[1,2,4]triazolo[4,3-a]pyridin-3(2H)-one;
1-(4-chlorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(3,5-difluorophenyl)-4-methyl-2,3,4,5-tetrahydro-1H-benzo[e][1,4]diazepine;
7-([1,2,4]triazolo[4,3-a]pyridin-6-yl)-1-(3,5-difluorophenyl)-4-methyl-2,3,4,5-tetrahydro-1H-benzo[e][1,4]diazepine;
2-(1-(3,5-difluorophenyl)-4-methyl-2,3,4,5-tetrahydro-1H-benzo[e][1,4]diazepin-7-yl)-[1,2,4]triazolo[4,3-a]pyridin-3(2H)-one;
1-(3,5-difluorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(3,4-difluorophenyl)-4-methyl-2,3,4,5-tetrahydro-1H-benzo[e][1,4]diazepine;
7-([1,2,4]triazolo[4,3-a]pyridin-6-yl)-1-(3,4-difluorophenyl)-4-methyl-2,3,4,5-tetrahydro-1H-benzo[e][1,4]diazepine;
2-(1-(3,4-difluorophenyl)-4-methyl-2,3,4,5-tetrahydro-1H-benzo[e][1,4]diazepin-7-yl)-[1,2,4]triazolo[4,3-a]pyridin-3(2H)-one;
1-(3,4-difluorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-1-(3,4-dichlorophenyl)-4-methyl-2,3,4,5-tetrahydro-1H-benzo[e][1,4]diazepine;
7-([1,2,4]triazolo[4,3-a]pyridin-6-yl)-1-(3,4-dichlorophenyl)-4-methyl-2,3,4,5-tetrahydro-1H-benzo[e][1,4]diazepine;
2-(1-(3,4-dichlorophenyl)-4-methyl-2,3,4,5-tetrahydro-1H-benzo[e][1,4]diazepin-7-yl)-[1,2,4]triazolo[4,3-a]pyridin-3(2H)-one;
1-(3,4-dichlorophenyl)-4-methyl-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
7-([1,2,4]triazolo[1,5-a]pyridin-6-yl)-4-methyl-1-(naphthalen-2-yl)-2,3,4,5-tetrahydro-1H-benzo[e][1,4]diazepine;
7-([1,2,4]triazolo[4,3-a]pyridin-6-yl)-4-methyl-1-(naphthalen-2-yl)-2,3,4,5-tetrahydro-1H-benzo[e][1,4]diazepine;
2-(4-methyl-1-(naphthalen-2-yl)-2,3,4,5-tetrahydro-1H-benzo[e][1,4]diazepin-7-yl)-[1,2,4]triazolo[4,3-a]pyridin-3(2H)-one;
4-methyl-1-(naphthalen-2-yl)-7-(3-(trifluoromethyl)-5,6-dihydro-[1,2,4]triazolo[4,3-a]pyrazin-7(8H)-yl)-2,3,4,5-tetrahydro-1H-benzo[e][1,4]diazepine;
6-fluoro-4-methyl-1-phenyl-7-(pyridazin-3-yl)-2,3,4,5-tetrahydro-1H-benzo[e][1,4]diazepine;
6-(6-fluoro-4-methyl-1-phenyl-2,3,4,5-tetrahydro-1H-benzo[e][1,4]diazepin-7-yl)pyridazin-3-amine;
6-fluoro-4-methyl-1-phenyl-7-(6-(trifluoromethyl)pyridazin-3-yl)-2,3,4,5-tetrahydro-1H-benzo[e][1,4]diazepine;
7-(6-(difluoromethyl)pyridazin-3-yl)-6-fluoro-4-methyl-1-phenyl-2,3,4,5-tetrahydro-1H-benzo[e][1,4]diazepine;
7-(6-(difluoromethoxy)pyridazin-3-yl)-6-fluoro-4-methyl-1-phenyl-2,3,4,5-tetrahydro-1H-benzo[e][1,4]diazepine;
6-fluoro-1-(4-fluorophenyl)-4-methyl-7-(pyridazin-3-yl)-2,3,4,5-tetrahydro-1H-benzo[e][1,4]diazepine;
6-(6-fluoro-1-(4-fluorophenyl)-4-methyl-2,3,4,5-tetrahydro-1H-benzo[e][1,4]diazepin-7-yl)pyridazin-3-amine;

6-fluoro-1-(4-fluorophenyl)-4-methyl-7-(6-(trifluoromethyl)pyridazin-3-yl)-2,3,4,5-tetrahydro-1H-benzo[e][1,4]diazepine;

7-(6-(difluoromethyl)pyridazin-3-yl)-6-fluoro-1-(4-fluorophenyl)-4-methyl-2,3,4,5-tetrahydro-1H-benzo[e][1,4]diazepine;

7-(6-(difluoromethoxy)pyridazin-3-yl)-6-fluoro-1-(4-fluorophenyl)-4-methyl-2,3,4,5-tetrahydro-1H-benzo[e][1,4]diazepine;

1-(4-chlorophenyl)-6-fluoro-4-methyl-7-(pyridazin-3-yl)-2,3,4,5-tetrahydro-1H-benzo[e][1,4]diazepine;

6-(1-(4-chlorophenyl)-6-fluoro-4-methyl-2,3,4,5-tetrahydro-1H-benzo[e][1,4]diazepin-7-yl)pyridazin-3-amine;

1-(4-chlorophenyl)-6-fluoro-4-methyl-7-(6-(trifluoromethyl)pyridazin-3-yl)-2,3,4,5-tetrahydro-1H-benzo[e][1,4]diazepine;

1-(4-chlorophenyl)-7-(6-(difluoromethyl)pyridazin-3-yl)-6-fluoro-4-methyl-2,3,4,5-tetrahydro-1H-benzo[e][1,4]diazepine;

1-(4-chlorophenyl)-7-(6-(difluoromethoxy)pyridazin-3-yl)-6-fluoro-4-methyl-2,3,4,5-tetrahydro-1H-benzo[e][1,4]diazepine;

1-(3,5-difluorophenyl)-6-fluoro-4-methyl-7-(pyridazin-3-yl)-2,3,4,5-tetrahydro-1H-benzo[e][1,4]diazepine;

6-(1-(3,5-difluorophenyl)-6-fluoro-4-methyl-2,3,4,5-tetrahydro-1H-benzo[e][1,4]diazepin-7-yl)pyridazin-3-amine;

1-(3,5-difluorophenyl)-6-fluoro-4-methyl-7-(6-(trifluoromethyl)pyridazin-3-yl)-2,3,4,5-tetrahydro-1H-benzo[e][1,4]diazepine;

7-(6-(difluoromethyl)pyridazin-3-yl)-1-(3,5-difluorophenyl)-6-fluoro-4-methyl-2,3,4,5-tetrahydro-1H-benzo[e][1,4]diazepine;

7-(6-(difluoromethoxy)pyridazin-3-yl)-1-(3,5-difluorophenyl)-6-fluoro-4-methyl-2,3,4,5-tetrahydro-1H-benzo[e][1,4]diazepine;

1-(3,4-difluorophenyl)-6-fluoro-4-methyl-7-(pyridazin-3-yl)-2,3,4,5-tetrahydro-1H-benzo[e][1,4]diazepine;

6-(1-(3,4-difluorophenyl)-6-fluoro-4-methyl-2,3,4,5-tetrahydro-1H-benzo[e][1,4]diazepin-7-yl)pyridazin-3-amine;

1-(3,4-difluorophenyl)-6-fluoro-4-methyl-7-(6-(trifluoromethyl)pyridazin-3-yl)-2,3,4,5-tetrahydro-1H-benzo[e][1,4]diazepine;

7-(6-(difluoromethyl)pyridazin-3-yl)-1-(3,4-difluorophenyl)-6-fluoro-4-methyl-2,3,4,5-tetrahydro-1H-benzo[e][1,4]diazepine;

7-(6-(difluoromethoxy)pyridazin-3-yl)-1-(3,4-difluorophenyl)-6-fluoro-4-methyl-2,3,4,5-tetrahydro-1H-benzo[e][1,4]diazepine;

1-(3,4-dichlorophenyl)-6-fluoro-4-methyl-7-(pyridazin-3-yl)-2,3,4,5-tetrahydro-1H-benzo[e][1,4]diazepine;

6-(1-(3,4-dichlorophenyl)-6-fluoro-4-methyl-2,3,4,5-tetrahydro-1H-benzo[e][1,4]diazepin-7-yl)pyridazin-3-amine;

1-(3,4-dichlorophenyl)-7-(6-(difluoromethyl)pyridazin-3-yl)-6-fluoro-4-methyl-2,3,4,5-tetrahydro-1H-benzo[e][1,4]diazepine;

6-fluoro-4-methyl-1-(naphthalen-2-yl)-7-(pyridazin-3-yl)-2,3,4,5-tetrahydro-1H-benzo[e][1,4]diazepine;

6-(6-fluoro-4-methyl-1-(naphthalen-2-yl)-2,3,4,5-tetrahydro-1H-benzo[e][1,4]diazepin-7-yl)pyridazin-3-amine; and 7-(6-(difluoromethyl)pyridazin-3-yl)-6-fluoro-4-methyl-1-(naphthalen-2-yl)-2,3,4,5-tetrahydro-1H-benzo[e][1,4]diazepine.

Within these embodiments, the selection of a particular preferred substituent at any one of $R^1$-$R^8$ does not affect the selection of a substituent at any of the others of $R^1$-$R^7$. That is, preferred compounds provided herein have any of the preferred substituents at any of the positions. For example, as described hereinabove, $R^1$ is preferably $C_1$-$C_6$ alkyl; the selection of $R^1$ as any one of $C_1$, $C_2$, $C_3$, $C_4$, $C_5$, or $C_6$ alkyl, does not limit the choice of $R^2$ in particular to any one of H, $C_1$-$C_6$ alkyl, or $C_1$-$C_6$ haloalkyl. Rather, for $R^1$ as any of $C_1$, $C_2$, $C_3$, $C_4$, $C_5$, or $C_6$ alkyl, $R^2$ is any of H, $C_1$, $C_2$, $C_3$, $C_4$, $C_5$, or $C_6$ alkyl or $C_1$, $C_2$, $C_3$, $C_4$, $C_5$, or $C_6$ haloalkyl. Similarly, the selection of $R^2$ as any of H, $C_1$, $C_2$, $C_3$, $C_4$, $C_5$, or $C_6$ alkyl or $C_1$, $C_2$, $C_3$, $C_4$, $C_5$, or $C_6$ haloalkyl does not limit the selection of $R^3$ in particular to any one of H, halogen, —$OR^{11}$, —$S(O)_nR^{12}$, —CN, —$C(O)R^{12}$, $C_1$-$C_6$ alkyl, $C_3$-$C_6$ cycloalkyl, $C_4$-$C_7$ cycloalkylalkyl, or substituted $C_4$-$C_7$ cycloalkylalkyl.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

Another embodiment of the present invention is a mixture of compounds of formulae I(A-D), where the compound of formulae I(A-D) is radiolabeled, i.e., where one or more of the atoms described are replaced by a radioactive isotope of that atom (e.g., C replaced by $^{14}$C and H replaced by $^3$H). Such compounds have a variety of potential uses, e.g., as standards and reagents in determining the ability of a potential pharmaceutical to bind to neurotransmitter proteins.

Another embodiment of the present invention is a pharmaceutical composition containing a therapeutically effective amount of the compound of formulae I(A-D), and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of formulae I(A-D), or a pharmaceutically acceptable salt thereof. The method of the present invention is capable of treating subjects afflicted with various neurological and psychiatric disorders including, without limitation: lower back pain, attention deficit hyperactivity disorder (ADHD), cognition impairment, anxiety disorders especially generalized anxiety disorder (GAD), panic disorder, bipolar disorder, also known as manic depression or manic-depressive disorder, obsessive compulsive disorder (OCD), post-traumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, supranuclear palsy, eating disorders, especially obesity, anorexia nervosa, bulimia nervosa, and binge eating disorder, analgesia, substance abuse disorders (including chemical dependencies) such as nicotine addiction, cocaine addiction, alcohol and amphetamine addiction, Lesch-Nyhan syndrome, neurodegenerative diseases such as Parkinson's disease, late luteal phase syndrome or narcolepsy, psychiatric symptoms such as anger, rejection sensitivity, movement disorders such as extrapyramidal syndrome, Tic disorders and restless leg syndrome (RLS), tardive dyskinesia, supranuclear palsy, sleep related eating disorder (SRED), night eating syndrome (NES), stress urinary incontinence (SUI), migraine, neuropathic pain, especially diabetic neuropathy, fibromyalgia syndrome (FS), chronic fatigue syndrome (CFS), sexual dysfunction, especially premature ejaculation and male impotence, and thermoregulatory disorders (e.g., hot flashes associated with menopause).

The compounds provided herein are particularly useful in the treatment of these and other disorders due, at least in part, to their ability to selectively bind to the transporter proteins for certain neurochemicals with a greater affinity than to the transporter proteins for other neurochemicals.

In another embodiment of the present invention, the above method further involves administering a therapeutically effective amount of a serotonin 1A receptor antagonist or a pharmaceutically acceptable salt thereof. Suitable serotonin 1A receptor antagonists include WAY 100135 and spiperone. WAY 100135 (N-(t-butyl)-3-[a-(2-methoxyphenyl)piperazin-1-yl]-2 phenylpropanamide) is disclosed as having an affinity for the serotonin 1A receptor in U.S. Pat. No. 4,988,814 to Abou-Gharbia et al., which is hereby incorporated by reference in its entirety. Also, Cliffe et al., *J Med Chem* 36:1509-10 (1993), which is hereby incorporated by reference in its entirety, showed that the compound is a serotonin 1A antagonist. Spiperone (8-[4-(4-fluorophenyl)-4-oxobutyl]-1-phenyl-1,3,8-triazaspiro[4,5]decan-4-one) is a well-known compound and is disclosed in U.S. Pat. Nos. 3,155,669 and 3,155,670, which are hereby incorporated by reference in their entirety. The activity of spiperone as a serotonin 1A antagonist is described in Middlemiss et al., *Neurosc and Biobehav Rev.* 16:75-82 (1992), which is hereby incorporated by reference in its entirety.

In another embodiment of the present invention, the above method further involves administering a therapeutically effective amount of a selective neurokinin-1 receptor antagonist or pharmaceutically acceptable salt thereof. Neurokinin-1 receptor antagonists that can be used in combination with the compound of formulae I(A-D), in the present invention are fully described, for example, in U.S. Pat. Nos. 5,373,003, 5,387,595, 5,459,270, 5,494,926, 5,162,339, 5,232,929, 5,242,930, 5,496,833, and 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293 168, 2 293 169, and 2 302 689; European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0 733 632 and 0 776 893, which are hereby incorporated by reference in their entirety. The preparations of such compounds are fully described in the aforementioned patents and publications.

In another embodiment of the present invention, the above method further involves administering a therapeutically effective amount of a norepinephrine precursor or a pharmaceutically acceptable salt thereof. Suitable norepinephrine precursors include L-tyrosine and L-phenylalanine.

Another aspect of the present invention is a method of inhibiting synaptic norepinephrine uptake in a patient in need thereof. The method involves administering a therapeutically effective inhibitory amount of a compound of formulae I(A-D).

Another aspect of the present invention is a method of inhibiting synaptic serotonin uptake in a patient in need thereof. The method involves administering a therapeutically effective inhibitory amount of a compound of formulae I(A-D).

Another aspect of the present invention is a method of inhibiting synaptic dopamine uptake in a patient in need thereof. The method involves administering a therapeutically effective inhibitory amount of a compound of formulae I(A-D).

Another aspect of the present invention is a kit comprising a compound of formulae I(A-D), and at least one compound selected from the group consisting of: a serotonin 1A receptor antagonist compound, a selective neurokinin-1 receptor antagonist compound, and a norepinephrine precursor compound.

Another aspect of the present invention relates to a method of treating a disorder referred to in the above-mentioned embodiments in a patient in need thereof. The method involves inhibiting synaptic serotonin and norepinephrine uptake by administering a therapeutically effective inhibitory amount of the compound of formulae I(A-D), which functions as both a dual acting serotonin and norepinephrine uptake inhibitor.

Another aspect of the present invention relates to a method of treating a disorder referred to in the above-mentioned embodiments in a patient in need thereof. The method involves inhibiting synaptic serotonin and dopamine uptake by administering a therapeutically effective inhibitory amount of the compound of formulae I(A-D), which functions as both a dual acting serotonin and dopamine uptake inhibitor.

Another aspect of the present invention relates to a method of treating a disorder referred to in the above-mentioned embodiments in a patient in need thereof. The method involves inhibiting synaptic dopamine and norepinephrine uptake by administering a therapeutically effective inhibitory amount of the compound of formulae I(A-D), which functions as both a dual acting dopamine and norepinephrine uptake inhibitor.

Another aspect of the present invention relates to a method of treating a disorder referred to in the above-mentioned embodiments in a patient in need thereof. The method involves inhibiting synaptic norepinephrine, dopamine and serotonin uptake by administering a therapeutically effective inhibitory amount of the compound of formulae I(A-D), which functions as a triple acting norepinephrine, dopamine, and serotonin uptake inhibitor.

Another aspect of the present invention relates to a method for inhibiting serotonin uptake in mammals. The method involves administering to a mammal requiring increased neurotransmission of serotonin a pharmaceutically effective amount of the compound of formulae I(A-D).

Another aspect of the present invention relates to a method for inhibiting dopamine uptake in humans. The method involves administering to a human requiring increased neurotransmission of dopamine a pharmaceutically effective amount of the compound of formulae I(A-D).

Another aspect of the present invention relates to a method for inhibiting norepinephrine uptake in humans. The method involves administering to a human requiring increased neurotransmission of norepinephrine a pharmaceutically effective amount of the compound of formulae I(A-D).

Another aspect of the present invention relates to a method of suppressing the desire of humans to smoke. The method involves administering to a human in need of such suppression an effective dose, to relieve the desire to smoke, of the compound of formulae I(A-D).

Another aspect of the present invention relates to a method of suppressing the desire of humans to consume alcohol. The method involves administering to a human in need of such suppression an effective dose, to relieve the desire to consume alcohol, of the compound of formulae I(A-D).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by Larock, R. C., *Comprehensive Organic Transformations*, VCH publishers, (1989), which is hereby incorporated by reference in its entirety.

A compound of formulae I(A-D), including a group containing one or more nitrogen ring atoms, may be converted to the corresponding compound where one or more nitrogen ring atom of the group is oxidized to an N-oxide, preferably by reacting with a peracid, for example, peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxyl, amino, imino, thio, or carboxy groups, where these are desired in the final product, to avoid their unwanted participation in the reactions. Conventional protecting groups may be used in accordance with standard practice; for examples, see Green, *Protective Groups in Organic Chemistry*, John Wiley and Sons (1991) and McOmie, *Protective Groups in Organic Chemistry*, Plenum Press (1973), which are hereby incorporated by reference in their entirety.

In the reaction schemes described hereinafter, the synthesis of tetrahydrobenzo-1,4-diazepines of formulae I(A-D) functionalized at $R^4$ with aryl, heteroaryl, or heterocyclic groups is described. The synthesis of tetrahydrobenzo-1,4-diazepines of formulae I(A-D) functionalized at $R^3$, $R^5$ or $R^6$ with aryl, heteroaryl, or heterocyclic groups may be achieved via similar routes, apparent to one skilled in the art of organic synthesis.

The novel tetrahydro-1,4-benzodiazepine reuptake inhibitors of formula (I; $R^4$=aryl, heteroaryl, or heterocyclic) of the present invention may be prepared by several known methods, as reviewed by Walser A. and Fryer, R. I., *Bicyclic Diazepines, Diazepines with an Additional Ring*, Volume 50, John Wiley and Sons (1991), which is hereby incorporated by reference in its entirety. One method, described in the above-mentioned reference, is outlined below (Scheme 1). The treatment of appropriately substituted isatoic anhydrides of formula (II), several of which may be obtained from commercial sources, with amino esters of formula (III), such as, but not limited to, sarcosine methyl ester, yields the corresponding benzo-1,4-diazepine-2,5-diones of formula (IV). The reaction is carried out in a solvent such as, but not limited to pyridine, at elevated temperature up to the reflux point of the solvent employed. Reduction of benzo-1,4-diazepine-2,5-diones of formula (IV) to the tetrahydrobenzo-1,4-diazepines of formula (V) proceeds with reducing agents including, for example, lithium aluminum hydride. The reductions are carried out for a period of time between 4 to 8 hours at elevated temperature up to the reflux point of the solvent employed. One skilled in the art will understand the optimal combination of reducing agents and reaction conditions required, or may seek guidance from Larock, R. C., *Comprehensive Organic Transformations*, VCH Publishers (1989), which is hereby incorporated by reference in its entirety.

Scheme 1

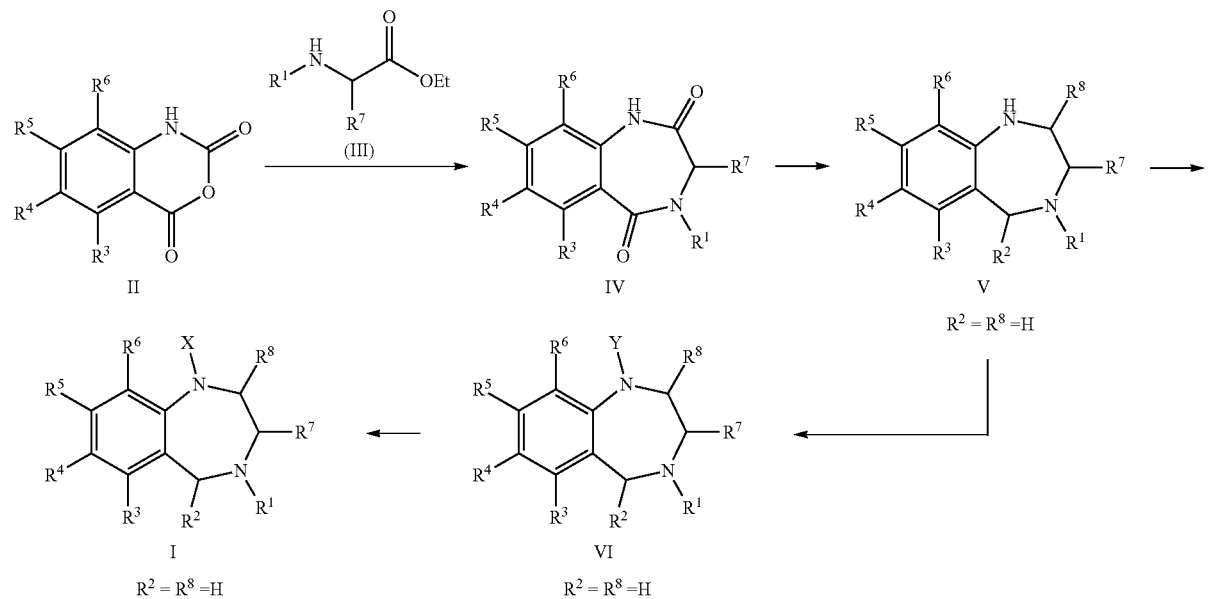

The compounds of formula (I; $R^4$=aryl, heteroaryl) of the present invention may be prepared from the corresponding tetrahydrobenzo-1,4-diazepines of formula (V; $R^4$=Br) by sequential N-arylation to install the substituents at the N-1 position, followed by either a second N-arylation, or a cross-coupling reaction, to install the substituent at the C-7 position.

Thus, tetrahydrobenzo-1,4-diazepines of formula (V; $R^4$=Br) are first reacted with an appropriate haloarene or aryl or heteroaryl boronic acid, in the presence of a metal catalyst, with or without a base, in an inert solvent. Metal catalysts include, but are not limited to, salts or complexes of Cu or Pd (e.g., CuI, $Cu(OAc)_2$, $Pd(OAc)_2$, $PdCl_2(dppf)$, $Pd_2(dba)_3$). Bases may include, but are not limited to, triethylamine, and alkali metal alkoxides (preferably, potassium tert-butoxide). A supporting ligand, such as, but not limited to, X-Phos or BINAP, is often used. Inert solvents may include, but are not limited to, aromatic hydrocarbons (preferably, benzene or toluene), aliphatic alcohols (preferably, tert-butanol), and halogenated solvents (preferably, dichloromethane). Preferred reaction temperatures range from room temperature up to the boiling point of the solvent employed. The reactions may be run in conventional glassware or in a sealed reaction vessel.

The 1-aryl/heteroaryl-7-bromo-tetrahydrobenzo-1,4-diazepines obtained thus may be reacted with an appropriate amine, amide or lactam, in the presence of a metal catalyst, with or without a base in an inert solvent to give the benzo-1,4-diazepine compounds of formula (I; $R^4$=aryl, heteroaryl) of the present invention. Metal catalysts include, but are not limited to, salts or complexes of Cu, Pd, or Ni (e.g., CuI, $Cu(OAc)_2$, $PdCl_2(dppf)$, $NiCl(OAc)_2$, $Ni(COD)_2$). Bases may include, but are not limited to, alkali metal carbonates, alkali metal phosphates (preferably potassium phosphate), alkali metal alkoxides (preferably, sodium tert-butoxide), and alkali metal bis(trialkylsilyl)amides (preferably, lithium bis(trimethylsilyl)amide). A supporting ligand, such as, but not limited to L-proline or dimethylethylenediamine is often used. Inert solvents may include, but are not limited to, cyclic ethers (preferably, tetrahydrofuran or 1,4-dioxane), N,N-dialkylformamides (preferably, dimethylformamide), dialkylsulfoxides (preferably, dimethylsulfoxide), or aromatic hydrocarbons (preferably, benzene or toluene). Preferred reaction temperatures range from room temperature up to the boiling point of the solvent employed. The reactions may be run in conventional glassware or in a sealed reaction vessel.

The 1-aryl/heteroaryl-7-bromo-tetrahydrobenzo-1,4-diazepines obtained previously may also be reacted with appropriate aryl or heteroaryl boronic acids or aryl or heteroaryl boronic acid esters of formula $R^4$—Z, where Z is equivalent to $B(OH)_2$ or $B(OR^a)(OR^b)$ (where $R^a$ and $R^b$ are lower alkyl, i.e., $C_1$-$C_6$, or taken together, $R^a$ and $R^b$ are lower alkylene, i.e., $C_2$-$C_{12}$) and $R^4$ is the corresponding aryl or heteroaryl group, in the presence of a metal catalyst with or without a base in an inert solvent to give the benzo-1,4-diazepine compounds of formula (I; $R^4$=aryl, heteroaryl) of the present invention. Metal catalysts include, but are not limited to, salts or phosphine complexes of Cu, Pd, or Ni (e.g., $Cu(OAc)_2$, $PdCl_2 (PPh_3)_2$, $NiCl_2 (PPh_3)_2$, $Pd(PPh_3)_4$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao et al., *Tetrahedron*, 50:979-988 (1994), which is hereby incorporated by reference in its entirety.

It will also be appreciated by one skilled in the art that the 1-aryl/heteroaryl-7-bromo-tetrahydrobenzo-1,4-diazepines obtained previously may be converted to the boronic acid or boronate ester and subsequently treated with the desired optionally substituted aryl or heteroaryl halide in discrete steps or in tandem as described by Baudoin et al., *J. Org. Chem.* 67:1199-1207 (2002), which is hereby incorporated by reference in its entirety.

Alternatively, the 1-aryl/heteroaryl-7-bromo-tetrahydrobenzo-1,4-diazepines described previously may be coupled with aryl or heteroaryl stannanes to yield the benzo-1,4-diazepine compounds of formula (I; $R^4$=aryl, heteroaryl) of the present invention. One skilled in the art will be familiar with the catalysts and reaction conditions that need to be employed to effect the desired transformation.

In addition, compounds of formula (V; $R^4$=Br) may be protected at the N-1 position using an appropriate protecting group, such as, but not limited to, acetyl and benzoyl, to give compounds of formula (VI; Y=acetyl or benzoyl). The acyl protecting group may be introduced on reaction of compounds of formula (V; R=Br) with an acyl chloride, such as, but not limited to, acetyl chloride or benzoyl chloride, in the presence of a base, such as, but not limited to triethylamine, or pyridine, in an appropriate inert solvent. Inert solvents include, for example, dichloromethane and dichloroethane. The choice of protecting groups will be evident to one skilled in the art; for additional guidance, one may also consult Green, *Protective Groups in Organic Chemistry*, John Wiley and Sons (1991) and McOmie, *Protective Groups in Organic Chemistry*, Plenum Press (1973), which are hereby incorporated by reference in their entirety.

The compounds of formula (VI; Y=acetyl or benzoyl; $R^4$=Br) may then be converted to the benzo-1,4-diazepine compounds of formula (I; $R^4$=aryl, heteroaryl) of the present invention by sequential cross coupling or N-arylation to install the substituents at the C-7 position, following by removal of the protecting group, and a second N-arylation step to install the substituent at the N-1 position. Accordingly, compounds of formula (VI; Y=acetyl or benzoyl; $R^4$=Br) may be reacted with aryl or heteroaryl boronic acids, aryl or heteroaryl boronic acid esters, aryl or heteroaryl stannanes, amines, amides or lactams as described above. Removal of the acyl protection group may be effected by treatment with a strong acid, such as hydrochloric acid, at elevated temperatures. Finally, a second N-arylation using an appropriate aryl or heteroaryl halide, under the reaction conditions described above gives the tetrahydrobenzo-1,4-diazepines of formulae I(A-D) of the present invention.

Compounds of formulae I(A-D) may be obtained in enantiomerically pure (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formulae I(A-D) hereinabove. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine, or serotonin transporters and their uptake mechanism are implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formulae I(A-D), and the additional active ingredient (alone or in combination with diluent or carrier) selected from a serotonin 1A receptor antagonist, a selective neurokinin-1 receptor antagonist, and a norepinephrine precursor.

In practice, the compounds of the present invention may generally be administered parenterally, intravenously, subcutaneously, intramuscularly, colonically, nasally, intraperitoneally, rectally, or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one the compound of formulae I(A-D).

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine, and serotonin uptake and are, therefore, believed to be useful in treating a disorder which is created by or is dependent upon decreased availability of serotonin, norepinephrine or dopamine. Although the compounds of formulae I(A-D) inhibit synaptic norepinephrine, dopamine, and serotonin uptake, in any individual compound, these inhibitory effects may be manifested at the same or vastly different concentrations or doses. As a result, some compounds of formulae I(A-D) are useful in treating such a disorder at doses at which synaptic norepinephrine uptake may be substantially inhibited but at which synaptic serotonin uptake or dopamine uptake is not substantially inhibited, or vice versa. Also, some compounds of formulae I(A-D) are useful in treating such a disorder at doses at which synaptic dopamine uptake may be substantially inhibited but at which synaptic norepinephrine or serotonin uptake is not substantially inhibited, or vice versa. And, conversely, some compounds of formulae I(A-D) are useful in treating such a disorder at doses at which synaptic serotonin uptake may be substantially inhibited but at which synaptic norepinephrine or dopamine uptake is not substantially inhibited, or vice versa. Other compounds of formulae I(A-D) are useful in treating such a disorder at doses at which synaptic norepinephrine, dopamine, and serotonin uptake are substantially inhibited.

The present invention provides compounds where the inhibitory effects on serotonin and norepinephrine uptake occurs at similar or even the same concentrations of these compounds, while the effects on inhibition of dopamine uptake occurs at vastly different concentrations or doses. As a result, some compounds of formulae I(A-D) are useful in treating such a disorder at doses at which synaptic serotonin and norepinephrine uptake may be substantially inhibited but at which synaptic dopamine uptake is not substantially inhibited, or vice versa.

The present invention provides compounds where the inhibitory effects on serotonin and dopamine uptake occurs at similar or even the same concentrations of these compounds while the effects on inhibition of norepinephrine uptake occurs at vastly different concentrations or doses. As a result, some compounds of formulae I(A-D) are useful in treating such a disorder at doses at which synaptic serotonin and dopamine uptake may be substantially inhibited but at which synaptic norepinephrine uptake is not substantially inhibited, or vice versa.

The present invention provides compounds where the inhibitory effects on norepinephrine and dopamine uptake occurs at similar or even the same concentrations of these compounds while the effects on inhibition of dopamine uptake occurs at vastly different concentrations or doses. As a result, some compounds of formulae I(A-D) are useful in treating such a disorder at doses at which synaptic norepinephrine and dopamine uptake may be substantially inhibited but at which synaptic serotonin uptake is not substantially inhibited, or vice versa.

The present invention provides compounds where the inhibitory effects on norepinephrine, dopamine and serotonin uptake occur at similar or even the same concentration. As a result, some compounds of formulae I(A-D) are useful in treating such a disorder at doses at which synaptic norepinephrine, dopamine, and serotonin uptake may all be substantially inhibited.

The concentrations or doses at which a test compound inhibits synaptic norepinephrine, dopamine, and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther* 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds having higher binding affinities for one or two of the neurotransmitter transporters, e.g., selectivity towards the norepinephrine transporter protein ("NET") over the transporters for other neurochemicals, e.g., the dopamine transporter protein ("DAT") and the serotonin transporter protein ("SERT").

Other compounds of the present invention may demonstrate selectivity towards the SERT over the transporters for other neuro chemicals, e.g., the DAT and the NET.

Still other compounds of the present invention may demonstrate selectivity towards the DAT over the transporters for other neurochemicals, e.g., the SERT and the NET.

Other compounds of the present invention may demonstrate selectivity towards the SERT and the NET over the transporter for other neurochemical, e.g., the DAT.

Still other compounds of the present invention may demonstrate selectivity towards the SERT and the DAT over the transporter for other neurochemical, e.g., the NET.

Still other compounds of the present invention may demonstrate selectivity towards the NET and the DAT over the transporter for other neurochemical, e.g., the SERT.

Finally other compounds possess nearly identical affinity towards the NET, the DAT, and the SERT.

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radio labelled ligands for the proteins. The binding of the radio ligands to the proteins is reversible in the presence of other protein ligands, e.g., the compounds of the present invention; said reversibility, as described below, provides a means of measuring the compounds' binding affinities for the proteins (Ki or $IC_{50}$). A higher Ki or IC$_{50}$ value for a compound is indicative that the compound has less binding affinity for a protein than is so for a compound with a lower Ki or IC$_{50}$; conversely, lower Ki or IC$_{50}$ values are indicative of greater binding affinities.

Accordingly, the difference in compound selectivity for proteins is indicated by a lower Ki or IC$_{50}$ for the protein for which the compound is more selective, and a higher Ki or IC$_{50}$ for the protein for which the compound is less selective. Thus, the higher the ratio in Ki or IC$_{50}$ values of a compound for protein A over protein B, the greater is the compounds' selectivity for the latter over the former (the former having a higher Ki or IC$_{50}$ and the latter a lower Ki or IC$_{50}$ for that compound). Compounds provided herein possess a wide range of selectivity profiles for the norepinephrine, dopamine, and serotonin transporters as reflected by the ratios of the experimentally determined Ki or IC$_{50}$ values.

Selected compounds ("mono action transporter reuptake inhibitors") of the present invention have potent binding affinity for each of the biogenic amine transporters NET, DAT or SERT. For example, selected compounds of the present invention possess potent (NET Ki or IC$_{50}$<100 nM) and selective binding affinity for NET, where the Ki or IC$_{50}$ ratio of DAT/NET and SERT/NET is greater than 10:1. Other selected compounds of the present invention possess potent (SERT Ki or IC$_{50}$<100 nM) and selective binding affinity for SERT, where the Ki or IC$_{50}$ ratio of NET/SERT and DAT/SERT is greater than 10:1. Other selected compounds of the present invention possess potent (DAT Ki or IC$_{50}$<100 nM) and selective binding affinity for DAT, where the Ki or IC$_{50}$ ratio of NET/DAT and SERT/DAT is greater than 10:1.

Selected compounds ("dual action transporter reuptake inhibitors") of the present invention have potent binding affinity for two of the biogenic amine transporters, NET, DAT or SERT. For example, selected compounds of the present invention possess potent (NET & SERT Ki or IC$_{50}$ values<100 nM) and selective binding affinity for NET and SERT, where the Ki ratio of DAT/NET and DAT/SERT is greater than 10:1 while the Ki or IC$_{50}$ ratio of SERT/NET or NET/SERT is less than 10:1. Other selected compounds of the present invention possess potent (NET & DAT Ki or IC$_{50}$ values<100 nM) and selective binding affinity for NET and DAT, where the Ki ratio of SERT/NET and SERT/DAT is greater than 10:1 while the Ki or IC$_{50}$ ratio of DAT/NET or NET/DAT is less than 10:1. Other selected compounds of this invention possess potent (DAT & SERT Ki or IC$_{50}$ values<100 nM) and selective binding affinity for DAT and SERT, where the Ki or IC$_{50}$ ratio of NET/DAT and SERT/DAT is greater than 10:1 while the Ki or IC$_{50}$ ratio of SERT/NET or NET/SERT is less than 10:1.

Selected compounds ("triple action transporter reuptake inhibitors") of the present invention have potent binding affinity simultaneously for all three of the biogenic amine transporters, NET, DAT or SERT. For example, selected compounds of this invention possess potent (NET, DAT & SERT Ki or IC$_{50}$ values<100 nM) where the Ki or IC$_{50}$ ratios of NET/DAT, NET/SERT, DAT/NET, DAT/SERT, SERT/NET and SERT/DAT are all less than 10:1.

Selected compounds of the present invention have potent binding affinity (Ki or IC$_{50}$ values<100 nM) for one, two, or three of the biogenic amine transporters, NET, DAT and SERT where the Ki or IC$_{50}$ ratios for any of NET/SERT, NET/DAT, DAT/NET, DAT/SERT, SERT/NET, and SERT/DAT fall outside of the bounds defined for the "Mono-, Dual or Triple action transporter reuptake inhibitors" defined above.

Selected compounds of the present invention have less potent binding affinity (Ki or IC$_{50}$ values between 100 nM and 1000 nM) for one, two, or three of the biogenic amine transporters, NET, DAT and SERT, where the Ki or IC$_{50}$ ratios for any of NET/SERT, NET/DAT, DAT/NET, DAT/SERT, SERT/NET, and SERT/DAT fall within the bounds defined for the "mono, dual, or triple action transporter reuptake inhibitors" defined above.

Finally, selected compounds of the present invention have less potent binding affinity (Ki or IC$_{50}$ values between 100 nM and 1000 nM) for one, two, or three of the biogenic amine transporters, NET, DAT, and SERT, where the Ki or IC$_{50}$ ratios for any of NET/SERT, NET/DAT, DAT/NET, DAT/SERT, SERT/NET, and SERT/DAT fall outside of the bounds defined for the "mono, dual, or triple action transporter reuptake inhibitors" defined above.

EXAMPLES

The following examples are provided to illustrate embodiments of the present invention but are by no means intended to limit its scope.

Example 1

Preparation of 1-(1-fluoronaphthalen-2-yl)-4-methyl-7-(pyridazin-3-yl)-2,3,4,5-tetrahydro-1H-benzo[e][1,4]diazepine, L-tartrate salt Step A: A mixture of isatoic anhydride (16.30 g, 100 mmol), sarcosine ethyl ester (15.40 g, 100 mmol) and pyridine (40 mL) was heated under reflux for 7 hours. After cooling, ethanol was added to the mixture until a precipitate was formed. Filtration gave the lactam as an off-white solid (11.04 g, 58%): ESI MS m/z 191 [M+H]$^+$.

Step B: To a suspension of lithium aluminum hydride (9.92 g, 261 mmol) in THF (250 mL) at 0° C. was added the lactam (11.04 g, 58.1 mmol) from Step A above. The mixture was then refluxed for 7 hours after the addition was completed. The cooled reaction mixture was quenched with water (200 mL) carefully and the resulting mixture was stirred at room temperature for 1 hour. The mixture was then extracted with methylene chloride (3×100 mL). The combined organic layer was dried over sodium sulfate, filtered and concentrated in vacuo to give the benzodiazepine (8.90 g, 95%) as a light yellow oil: ESI MS m/z 163 [M+H]$^+$.

Step C: To a solution of the benzodiazepine (8.90 g, 54.9 mmol) from Step B above in DMF (100 mL) at 0° C. was added N-bromosuccinimide (10.3 g, 57.7 mmol). The mixture was stirred at 0° C. for 3 hours. The solvent was then evaporated in vacuo and the residue was dissolved in ethyl acetate (500 mL). The mixture was washed with 1 N NaOH, dried over sodium sulfate, filtered and concentrated in vacuo. The residue was purified by column chromatography (90:10 methylene chloride/methanol) to give the desired bromobenzodiazepine (9.90 g, 75%) as a yellow solid: $^1$H NMR (CDCl$_3$, 500 MHz) δ 7.23 (s, 1H), 7.17 (d, J=8.3 Hz, 1H), 6.61 (d, J=8.3 Hz, 1H), 3.86 (br, 1H), 3.63 (s, 2H), 3.13-3.11 (m, 2H), 2.87-2.85 (m, 2H), 2.38 (s, 3H); ESI MS m/z 241 [M+H]$^+$.

Step D: To a solution of the bromobenzodiazepine (4.80 g, 20 mmol) from Step C above and pyridine (3.8 mL) in methylene chloride (50 mL) at 0° C. was added benzoyl chloride (6.18 g, 44.0 mmol) dropwise. The mixture was stirred at 0° C. for 1 hour, at which time a white precipitate was formed. Saturated NaHCO$_3$ (50 mL) was added to quench the reaction, and the mixture was brought to pH 9-10 by adding 2 N NaOH. The two phases were separated, and the organic phase was dried over sodium sulfate, filtered and concentrated in vacuo. The residue was purified by column chromatography (ethyl acetate, then 90:10 ethyl acetate/methanol) to give the benzoylbenzodiazepine (6.18 g, 90%) as a yellow solid: $^1$H NMR (CDCl$_3$, 300 MHz) δ 7.56 (s, 1H), 7.33-7.17 (m, 6H), 6.55 (d, J=7.8 Hz, 1H), 5.11 (br, 1H), 4.22 (br, 1H), 4.03 (br, 1H), 3.27 (br, 3H), 2.65 (s, 3H); ESI MS m/z 345 [M+H]$^+$.

Step E: A round bottomed flask was charged with the benzoylbenzodiazepine (6.18 g, 17.9 mmol) from Step D above, bis(pinacolato)diboron (5.00 g, 19.7 mmol) and potassium acetate (5.27 g, 53.7 mmol), dichloro[1,1'-bis(diphenylphosphino)ferrocene]palladium(II) dichloromethane adduct (1.31 g, 1.79 mmol) and DMF (80 mL). The mixture was degassed with nitrogen (3×) and then stirred at 60° C. overnight. The mixture was then cooled to room temperature, and cesium carbonate (17.5 g, 53.7 mmol), 3,6-dichloropyridazine (4.00 g, 26.9 mmol) and water (41 mL) were added to it. The mixture was degassed with nitrogen (3×) and then stirred at 60° C. for 3 hours. After cooling, the mixture was partitioned between methylene chloride and water. The aqueous phase was extracted with methylene chloride (3×100 mL). The combined organic extract was dried over sodium sulfate, filtered and concentrated in vacuo. The residue was purified by column chromatography (100:0 to 85:15 ethyl acetate/methanol) to yield the desired chloropyridazinobenzodiazepine (5.64 g, 83%) as a grey solid: $^1$H NMR (CDCl$_3$, 500 MHz) δ 8.07 (s, 1H), 7.75 (d, J=9.0 Hz, 1H), 7.59 (s, 1H), 7.54 (d, J=9.0 Hz, 1H), 7.28-7.18 (m, 5H), 6.77 (s, 1H), 5.01 (br, 1H), 4.12 (br, 1H), 3.91 (br, 1H), 3.00 (m, 3H), 2.47 (s, 3H); ESI MS m/z 379 [M+H]$^+$.

Step F: A mixture of the chloropyridazinobenzodiazepine (1.93 g, 5.09 mmol) from Step E above, ammonium formate (1.61 g, 25.5 mmol), 10% palladium on carbon (0.32 g) and methanol (100 mL) was heated under overnight. After cooling, the mixture was filtered through a celite pad and concentrated in vacuo. The crude product was partitioned between water (50 mL) and methylene chloride (50 mL). The aqueous phase was basified to pH 9 by adding 2 N NaOH. The two phases were separated and the aqueous phase was extracted with methylene chloride (50 mL). The combined organic extract was dried over sodium sulfate, filtered and concentrated in vacuo. The residue was purified by column chromatography (100:0 to 90:10 methylene chloride/methanol) to yield the desired pyridazinobenzodiazepine (1.60 g, 91%) as a off-white solid: $^1$H NMR (CDCl$_3$, 500 MHz) δ 9.14 (s, 1H), 8.12 (s, 1H), 7.78 (d, J=8.4 Hz, 1H), 7.61 (br, 1H), 7.52 (d, J=8.6 Hz, 1H), 7.28-7.18 (m, 5H), 6.78 (br, 1H), 5.02 (br, 1H), 4.15 (br, 1H), 3.92 (br, 1H), 3.14-3.07 (m, 3H), 2.47 (s, 3H); ESI MS m/z 345 [M+H]$^+$.

Step G: A mixture of the pyridazinobenzodiazepine (1.58 g, 4.59 mmol) from Step F above and 6 N HCl (10 mL) was refluxed for 4 hours. The solvents were removed in vacuo, and the residue was basified to pH 9 by adding 2 N NaOH. The mixture was extracted with methylene chloride (3×50 mL). The combined extract was dried over sodium sulfate, filtered and concentrated in vacuo. The residue was purified by column chromatography (80:19:1 methylene chloride/methanol/ammonium hydroxide) to yield the desired benzodiazepine (1.12 g, quantitative) as a yellow solid: $^1$H NMR (500 MHz, CDCl$_3$) δ 9.07 (s, 1H), 7.91 (s, 1H), 7.84 (d, J=8.2 Hz, 1H), 7.78 (d, J=8.4 Hz, 1H), 7.47-7.44 (m, 1H), 6.86 (d, J=8.2 Hz, 1H), 4.10 (br, 1H), 3.83 (s, 2H), 3.24-3.23 (m, 2H), 2.92-2.90 (m, 2H), 2.44 (s, 3H); ESI MS m/z 241 [M+H]$^+$.

Step H: A sealed tube was charged with the pyridazinobenzodiazepine (55 mg, 0.23 mmol) from Step G above, 2-bromo-1-fluoronaphthalene (77 mg, 0.34 mmol), palladium acetate (1.2 mg, 5 μmmol), X-phos (4.8 mg, 0.01 mmol), potassium tert-butoxide, and a mixture of tert-butyl alcohol and toluene (1/5, 1.2 mL). The reaction was conducted under microwave irradiation (200 W) at 120° C. for 20 minutes. The mixture was filtered through a celite pad and washed with methylene chloride. The filtrate was concentrated in vacuo and the residue was purified by column chromatography (methylene chloride, then 10:1 methylene chloride/methanol) to yield the desired benzodiazepine (39 mg, 43%) as a colorless oil: $^1$H NMR (500 MHz, CDCl$_3$) δ 9.09 (s, 1H), 8.06 (m, 2H), 7.80-7.65 (m, 3H), 7.61 (d, J=8.8 Hz, 1H), 7.55-7.52 (m, 1H), 7.48-7.45 (m, 2H), 7.30 (t, J=8.2 Hz, 1H), 6.77 (d, J=8.4 Hz, 1H), 4.01 (s, 2H), 3.90-3.88 (m, 2H), 2.96-2.94 (m, 2H), 2.50 (s, 3H); ESI MS m/z 385 [M+H]$^+$.

Step I: To a solution of the benzodiazepine (39 mg, 0.1 mmol) from Step H above in methanol (1 mL) was added L-tartaric acid (15 mg, 0.1 mmol). After the mixture was stirred at room temperature for 10 minutes, water (10 mL) was added to it. The resultant solution was lyophilized overnight to give 1-(1-fluoronaphthalen-2-yl)-4-methyl-7-(pyridazin-3-yl)-2,3,4,5-tetrahydro-1H-benzo[e][1,4]diazepine, L-tartrate salt (49 mg, 89%, AUC HPLC 98.2%) as a yellow powder: $^1$H NMR (CD$_3$OD, 500 MHz) δ 9.10 (s, 1H), 8.23 (s, 1H), 8.14 (d, J=8.6 Hz, 1H), 8.01 (d, J=8.5 Hz, 1H), 7.91 (d, J=8.5 Hz, 2H), 7.79-7.72 (m, 2H), 7.62-7.50 (m, 3H), 6.79 (d, J=8.6 Hz, 1H), 4.64 (s, 2H), 4.42 (s, 2H), 4.15 (s, 2H), 3.55 (s, 2H), 3.01 (s, 3H); ESI MS m/z 385 [M+H]$^+$.

Example 2

Preparation of 4-methyl-1-(4-(methylsulfonyl)phenyl)-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-4-(methylsulfonyl)benzene. The desired free base was obtained in 37% yield as a colorless oil. A procedure similar to the one in Step I of Example 1 was used to obtain the L-tartrate salt in 75% yield as an off-white powder: $^1$H NMR (CD$_3$OD, 500 MHz) δ 9.19 (s, 1H), 8.37 (s, 1H), 8.28-8.23 (m, 2H), 7.86-7.83 (m, 1H), 7.78 (d, J=8.9 Hz, 2H), 7.55 (d, J=8.3 Hz, 1H), 7.03 (s, 2H), 4.44 (s, 2H), 4.32 (br, 2H), 4.15 (br, 2H), 3.44 (br, 2H), 3.06 (s, 3H), 2.87 (br, 3H); ESI MS m/z 395 [M+H]$^+$.

Example 3

Preparation of 1-(3,5-difluorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1,3-difluoro-5-iodobenzene. The desired free base was obtained in 67% yield as a colorless oil. A procedure similar to the one in Step I of Example 1 was used to obtain the L-tartrate salt in 75% yield as an off-white powder: $^1$H NMR (CD$_3$OD, 500 MHz) δ 9.18 (s, 1H), 8.34 (s, 1H), 8.27-8.20 (m, 2H), 7.83 (s, 1H, br), 7.50 (br, 1H), 6.46-6.36 (m, 3H), 4.42-4.40 (m, 2H), 4.31 (s, 2H), 4.02 (br, 2H), 3.39 (br, 2H), 2.86 (s, 3H); ESI MS m/z 353 [M+H]$^+$.

Example 4

Preparation of 1-(2,4-difluorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-2,4-difluorobenzene. The desired free base was obtained in 6% yield as a colorless oil. A procedure similar to the one in Step I of Example 1 was used to obtain the L-tartrate salt in 83% yield as an off-white powder: $^1$H NMR (CD$_3$OD, 500 MHz) δ 9.11 (s, 1H), 8.20 (s, 1H), 8.14 (d, J=8.7 Hz, 1H), 7.95 (d, J=8.5 Hz, 1H), 7.78-7.75 (m, 1H), 7.47 (br, 1H), 7.10-7.07 (m, 2H), 6.76 (d, J=8.3 Hz, 1H), 4.53 (s, 2H), 4.43 (s, 2H), 3.96 (s, 2H), 3.45 (s, 2H), 2.95 (s, 3H); ESI MS m/z 353 [M+H]$^+$.

Example 5

Preparation of 4-methyl-7-(pyridazin-3-yl)-1-(3-(trifluoromethyl)phenyl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-3-(trifluoromethyl)benzene. The desired free base was obtained in 64% yield as a colorless oil. A procedure similar to the one in Step I of Example 1 was used to obtain the L-tartrate salt. The desired salt was obtained in 90% yield as an off-white powder: $^1$H NMR (CD$_3$OD, 500 MHz) δ 9.17 (d, J=4.9 Hz, 1H), 8.34 (s, 1H), 8.26-8.23 (m, 1H), 8.17 (d, J=8.3 Hz, 1H), 7.82 (dd, J=5.0, 8.7 Hz, 1H), 7.45 (t, J=5.1 Hz, 1H), 7.40 (d, J=8.4 Hz, 1H), 7.21-7.16 (m, 3H), 4.43 (s, 2H), 4.37 (br, 2H), 4.09 (br, 2H), 3.42 (br, 2H), 2.89 (s, 3H); ESI MS m/z 385 [M+H]$^+$.

Example 6

Preparation of 1-(5-fluoronaphthalen-2-yl)-4-methyl-7-(pyridazin-3-yl)-2,3,4,5-tetrahydro-1H-benzo[e][1,4]diazepine, L-tartrate salt A sealed tube was charged with 4-methyl-7-(pyridazin-3-yl)-2,3,4,5-tetrahydro-1H-benzo[e][1,4]diazepine (55 mg, 0.23 mmol), 5-fluoronaphthalen-2-yl trifluoromethanesulfonate (100 mg, 0.34 mmol), palladium acetate (1.2 mg, 5 μmmol), X-phos (4.8 mg, 0.01 mmol), cesium carbonate (111 mg, 0.34 mmol), celite (89 mg) and a mixture of tert-butyl alcohol and toluene (1/5, 1.2 mL). The reaction was conducted under microwave irradiation (250 W) at 140° C. for 20 minutes. The mixture was filtered through a celite pad and washed with methylene chloride. The filtrate was concentrated in vacuo and the residue was purified by column chromatography (methylene chloride, then 10:1 methylene chloride/methanol) to yield the desired benzodiazepine (61 mg, 70%) as a colorless oil. The desired salt was obtained in 88% yield as an off-white powder by a procedure similar to the one in Step I of Example 1: $^1$H NMR (CD$_3$OD, 500 MHz) δ 9.17 (d, J=4.8 Hz, 1H), 8.34 (s, 1H), 8.24 (d, J=7.5 Hz, 1H), 8.15 (d, J=8.3 Hz, 1H), 7.95 (d, J=9.0 Hz, 1H), 7.82 (d, J=3.8 Hz, 1H), 7.52 (d, J=8.3 Hz, 1H), 7.39-7.24 (m, 3H), 7.25 (br, 1H), 6.92 (br, 1H), 4.43 (s, 4H), 4.17 (br, 2H), 3.45 (br, 2H), 2.92 (s, 3H); ESI MS m/z 385 [M+H]$^+$.

Example 7

Preparation of 1-(4-fluoronaphthalen-2-yl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 3-bromo-1-fluoronaphthalene. The desired free base was obtained in 74% yield as a yellow solid. A procedure similar to the one in Step I of Example 1 was used to obtain the L-tartrate salt in 83% yield as an off-white powder: $^1$H NMR (CD$_3$OD, 500 MHz) δ 9.18 (d, J=4.9 Hz, 1H), 8.34 (s, 1H), 8.24 (d, J=7.6 Hz, 1H), 8.16 (d, J=8.3 Hz, 1H), 7.92 (d, J=8.3 Hz, 1H), 7.83 (dd, J=7.8, 4.9 Hz, 1H), 7.73 (d, J=8.4 Hz, 1H), 7.48 (t, J=7.2 Hz, 1H), 7.41 (d, J=8.3 Hz, 1H), 7.37 (t, J=7.3 Hz, 1H), 7.19 (s, 1H), 6.92 (d, J=13.1 Hz, 1H), 4.44 (s, 2H), 4.41 (s, 2H), 4.15 (s, 2H), 3.45 (s, 2H), 2.92 (s, 3H); ESI MS m/z 385 [M+H]$^+$.

Example 8

Preparation of 3-(4-methyl-7-(pyridazin-3-yl)-2,3,4,5-tetrahydro-1H-benzo[e][1,4]diazepin-1-yl)benzonitrile, L-tartrate salt A procedure similar to the one in Step H of Example 1 was used to couple 4-methyl-7-(pyridazin-3-yl)-2,3,4,5-tetrahydro-1H-benzo[e][1,4]diazepine with 3-bromobenzonitrile. The desired free base was obtained in 59% yield as a yellow solid. A procedure similar to the one in Step I of Example 1 was used to obtain the L-tartrate salt in 97% yield as an off-white powder: $^1$H NMR (CD$_3$OD, 500 MHz) δ 9.18 (d, J=4.8 Hz, 1H), 8.33 (s, 1H), 8.24 (d, J=8.7 Hz, 1H), 8.17 (d, J=8.3 Hz, 1H), 7.84-7.81 (m, 1H), 7.43-7.38 (m, 2H), 7.23-7.18 (m, 3H), 4.43 (s, 2H), 4.28 (br, 2H), 4.06 (br, 2H), 3.34 (s, 2H), 2.83 (s, 3H); ESI MS m/z 342 [M+H]$^+$.

Example 9

Preparation of 1-(benzo[d][1,3]dioxol-5-yl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 5-bromobenzo[d][1,3]dioxole. The desired free base was obtained in 10% yield as a colorless oil. A procedure similar to the one in Step I of Example 1 was used to obtain the L-tartrate salt in 88% yield as an off-white powder: $^1$H NMR (CD$_3$OD, 500 MHz) δ 9.12 (d, J=4.8 Hz, 1H), 8.22 (s, 1H), 8.16 (d, J=7.5 Hz, 1H), 7.95 (d, J=8.2 Hz, 1H), 7.79-7.76 (m, 1H), 7.00 (d, J=8.5 Hz, 1H), 6.82 (d, J=8.3 Hz, 1H), 6.69 (s, 1H), 6.61 (d, J=8.3 Hz, 1H), 5.95 (s, 2H), 4.49 (br, 2H), 4.43 (s, 2H), 3.97 (br, 2H), 3.45 (br, 2H), 2.96 (s, 3H); ESI MS m/z 361 [M+H]$^+$.

Example 10

Preparation of 4-methyl-1-(naphthalen-1-yl)-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromonaphthalene. The desired free base was obtained in 10% yield as a colorless oil. A procedure similar to the one in Step I of Example 1 was used to obtain the L-tartrate salt in 88% yield as an off-white powder: $^1$H NMR (CD$_3$OD, 500 MHz) δ 9.07 (s, 1H), 8.24 (s, 1H), 8.07 (s, 1H), 7.91 (s, 1H), 7.83 (s, 1H), 7.76-7.61 (m, 3H), 7.60-7.59 (m, 2H), 7.46 (s, 1H), 7.42 (s, 1H), 6.40 (s, 1H), 4.80 (br, 2H), 4.42 (s, 2H), 4.20 (br, 2H), 3.63 (s, 2H), 3.04 (s, 3H); ESI MS m/z 367 [M+H]$^+$.

Example 11

Preparation of 4-methyl-1-phenyl-2,3,4,5-tetrahydro-1H-benzo[e][1,4]diazepine, L-tartrate salt A procedure similar to the one in Step H of Example 1 was used to couple 4-methyl-2,3,4,5-tetrahydro-1H-benzo[e][1,4]diazepine with bromobenzene. The desired free base was obtained in 36% yield as a yellow solid. A procedure similar to the one in Step I of Example 1 was used to obtain the L-tartrate salt in 95% yield as an off-white powder: $^1$H NMR (CD$_3$OD, 500 MHz) δ 7.53 (d, J=7.5 Hz, 1H), 7.43 (s, 1H), 7.30-7.18 (m, 4H), 6.85-6.82 (m, 3H), 4.39 (s, 2H), 4.23 (s, 2H), 3.97 (br, 2H), 3.36 (s, 2H), 2.83 (s, 3H); ESI MS m/z 239 [M+H]$^+$.

Example 12

Preparation of 1-(3,4-difluorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 4-bromo-1,2-difluorobenzene. The desired free base was obtained in 47% yield as a colorless oil. A procedure similar to the one in Step I of Example 1 was used to obtain the L-tartrate salt in 88% yield as an off-white powder: $^1$H NMR (CD$_3$OD, 500 MHz) δ 9.16 (s, 1H), 8.29 (s, 1H), 8.22 (s, 1H), 8.11 (s, 1H), 7.81 (t, J=4.7 Hz, 1H), 7.31 (d, J=8.3 Hz, 1H), 7.16 (s, 1H), 6.91 (s, 1H), 6.74 (d, J=9.1 Hz, 1H), 4.44 (s, 2H), 4.35 (s, 2H), 3.98 (s, 2H), 3.35 (s, 2H), 2.87 (s, 3H); ESI MS m/z 353 [M+H]$^+$.

Example 13

Preparation of 1-(3-fluorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-3-fluorobenzene. The desired free base was obtained in 57% yield as a colorless oil. A procedure similar to the one in Step I of Example 1 was used to obtain the L-tartrate salt in 76% yield as an off-white powder: $^1$H NMR (CD$_3$OD, 500 MHz) δ 9.16 (s, 1H), 8.32 (s, 1H), 8.22 (s, 1H), 8.15 (s, 1H), 7.82 (s, 1H), 7.40 (s, 1H), 7.25 (s, 1H), 6.73-6.61 (m, 3H), 4.41 (s, 2H), 4.37 (s, 2H), 4.03 (s, 2H), 3.42 (s, 2H), 2.89 (s, 3H); ESI MS m/z 335 [M+H]$^+$.

Example 14

Preparation of 4-methyl-1-(naphthalen-2-yl)-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 2-bromonaphthalene. The desired free base was obtained in 52% yield as a yellow solid. A procedure similar to the one in Step I of Example 1 was used to obtain the L-tartrate salt in 72% yield as an off-white powder: $^1$H NMR (CD$_3$OD, 500 MHz) δ 9.16 (s, 1H), 8.32 (s, 1H), 8.22 (s, 1H), 8.10 (t, J=6.4 Hz, 1H), 7.80-7.72 (m, 4H), 7.74 (s, 2H), 7.32-7.28 (m, 2H), 7.11 (s, 1H), 4.49 (s, 2H), 4.43 (s, 2H), 4.18 (s, 2H), 3.50 (s, 2H), 2.96 (s, 3H); ESI MS m/z 367 [M+H]$^+$.

Example 15

Preparation of 1-(3,4-dichlorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 4-bromo-1,2-dichlorobenzene. The desired free base was obtained in 26% yield as a yellow oil. A procedure similar to the one in Step I of Example 1 was used to obtain the L-tartrate salt in 82% yield as an off-white powder: $^1$H NMR (CD$_3$OD, 500 MHz) δ 9.16 (s, 1H), 8.31 (s, 1H), 8.25-8.18 (m, 1H), 8.16 (t, J=6.3 Hz, 1H), 7.82 (s, 1H), 7.41 (d, J=8.3 Hz, 1H), 7.35 (d, J=8.9 Hz, 1H), 7.07 (s, 1H), 6.85 (s, 1H), 4.41 (s, 2H), 4.35 (s, 2H), 4.02 (s, 2H), 3.39 (s, 2H), 2.88 (s, 3H); ESI MS m/z 386 [M+H]$^+$.

Example 16

Preparation of 1-(2-fluorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-2-fluorobenzene. The desired free base was obtained in 28% yield as a yellow oil. A procedure similar to the one in Step I of Example 1 was used to obtain the L-tartrate salt in 65% yield as an off-white powder: $^1$H NMR (CD$_3$OD, 500 MHz) δ 9.11 (s, 1H), 8.20 (s, 1H), 8.14 (d, J=8.9 Hz, 1H), 7.94 (d, J=8.5 Hz, 1H), 7.78-7.75 (m, 1H), 7.42 (s, 1H), 7.27-7.15 (m, 3H), 6.78 (d, J=8.5 Hz, 1H), 4.55 (s, 2H), 4.41 (s, 2H), 4.00 (s, 2H), 3.45 (s, 2H), 2.96 (s, 3H); ESI MS m/z 335 [M+H]$^+$.

Example 17

Preparation of 1-(3-chlorophenyl)-4-methyl-7-(pyridazin-3-yl)-2,3,4,5-tetrahydro-1H-benzo[e][1,4]diazepine, L-tartrate salt A procedure similar to the one in Step H of Example 1 was used to couple 4-methyl-7-(pyridazin-3-yl)-2,3,4,5-tetrahydro-1H-benzo[e][1,4]diazepine with 1-bromo-3-chlorobenzene. The desired free base was obtained in 70% yield as a yellow oil. A procedure similar to the one in Step I of Example 1 was used to obtain the L-tartrate salt in 99% yield as a yellow solid: $^1$H NMR (CD$_3$OD, 500 MHz) δ 9.17-9.15 (m, 1H), 8.31-8.30 (m, 1H), 8.24-8.22 (m, 1H), 7.82-7.81 (m, 1H), 7.38 (d, J=8.0 Hz, 1H), 7.21 (t, J=8.0 Hz, 1H), 6.94-6.93 (m, 1H), 6.89-6.86 (m, 2H), 4.42 (s, 2H), 4.32 (s, 2H), 4.02 (bs, 2H), 3.38-3.36 (m, 2H), 2.86 (s, 3H); ESI MS m/z 351 [M+H]$^+$.

Example 18

Preparation of 4-methyl-1-phenyl-7-(pyridazin-3-yl)-2,3,4,5-tetrahydro-1H-benzo[e][1,4]diazepine, L-tartrate salt A mixture of 4-methyl-7-(pyridazin-3-yl)-2,3,4,5-tetrahydro-1H-benzo[e][1,4]diazepine (48 mg, 0.2 mmol), bromobenzene (47 mg, 0.3 mmol), bis(dibenzylidineacetone)

palladium(0) (0.9 mg, 1.0 μmmol), racemic-2,2'-bis (diphenylphosphino)-1,1'-binaphthyl (1.9 mg, 3.0 μmmol), potassium tert-butoxide (34 mg, 0.3 mmol) and toluene (1 mL) was heated at 80° C. under nitrogen in a sealed tube for 24 hours. After cooling, the mixture was partitioned between methylene chloride (10 mL) and water (10 mL). The aqueous phase was extracted with methylene chloride (10 mL). The combined organic extract was dried over sodium sulfate, filtered and concentrated in vacuo. The residue was purified by column chromatography (methylene chloride, then 90:10 methylene chloride/methanol) to give the desired free base (12 mg, 19%) as a light yellow solid. A procedure similar to the one in Step I of Example 1 was used to obtain the L-tartrate salt in 92% yield as an off-white powder: $^1$H NMR (CD$_3$OD, 500 MHz) δ 9.15 (s, 1H), 8.28 (s, 1H), 8.20 (d, J=8.6 Hz, 1H), 8.06 (d, J=8.4 Hz, 1H), 7.82 (s, 1H), 7.31-7.22 (m, 3H), 7.02-6.96 (m, 3H), 4.43 (s, 2H), 4.38 (s, 2H), 4.03 (s, 2H), 3.39 (s, 2H), 2.89 (s, 3H); ESI MS m/z 317 [M+H]$^+$.

Example 19

Preparation of 1-(1-(4-chlorophenyl)-4-methyl-2,3,4, 5-tetrahydro-1H-benzo[e][1,4]diazepin-7-yl)pyridin-2(1H)-one, L-tartrate salt Step A: A mixture of 7-bromo-4-methyl-2,3,4,5-tetrahydro-1H-benzo[e][1,4]diazepine (2.25 g, 9.33 mmol), 1-chloro-4-iodobenzene (3.10 g, 12.1 mmol), 2-(dicyclohexylphosphino)-2',4',6'-tri-i-isopropyl-1,1'-biphenyl (444 mg, 0.933 mmol), and cesium carbonate (6.1 g, 18.7 mmol) in toluene (60 mL) was purged with argon for 10 minutes before palladium(II) acetate (210 mg, 0.993 mmol) was added. After purging with argon for 5 minutes, the reaction mixture was heated at reflux overnight. The mixture was cooled, partitioned with water (100 mL) and ethyl acetate (3×50 mL). The combined organic extracts were dried over sodium sulfate, filtered and concentrated in vacuo. The residue was purified by flash chromatography eluting with 10:1 methylene chloride/methanol followed by rechromatography eluting with 3:1 methylene chloride/ethyl acetate to yield 7-bromo-1-(4-chlorophenyl)-4-methyl-2,3,4,5-tetrahydro-1H-benzo[e][1, 4]diazepine (694 mg, 21%) as a brown foam: $^1$H NMR (CDCl$_3$, 500 MHz) δ 7.45 (s, 1H), 7.37 (d, J=8.4 Hz, 1H), 7.12 (d, J=6.8 Hz, 2H), 7.01 (d, J=8.4 Hz, 1H), 6.62 (d, J=6.9 Hz, 2H), 3.71-3.67 (m, 2H), 3.60 (s, 2H), 2.88-2.85 (m, 2H), 2.36 (s, 3H); ESI MS m/z 351, 353 [M+H]$^+$.

Step B: A mixture of the bromobenzodiazepine (95 mg, 0.270 mmol) from Step A above, 2-hydroxypyridine (35 mg, 0.378 mmol), potassium phosphate (114 mg, 0.540 mmol), and N,N-dimethylethylenediamine (10 mg, 0.054 mmol) in 1,4-dioxane (2.0 mL) was purged with argon for 10 min before copper(I) iodide (10 mg, 0.0413 mmol) was added. After purging with argon for 10 minutes, the sealed tube reaction was heated at 110° C. overnight. The reaction mixture was cooled, partitioned with water (50 mL) and ethyl acetate (3×50 mL). The combined organic extracts were washed with brine (50 mL), dried over sodium sulfate, filtered, and concentrated in vacuo. The residue was purified once by flash chromatography and once by preparative thin-layer chromatography eluting with methylene chloride/ methanol (9:1) to give the desired benzodiazepine (10 mg, 10%) as a white solid. To a solution of the benzodiazepine (10 mg, 0.027 mmol) in methanol (1 mL) and water (3 mL) was added L-tartaric acid (4.1 mg, 0.027 mmol) and the resultant solution was lyophilized overnight to give 1-(1-(4-chlorophenyl)-4-methyl-2,3,4,5-tetrahydro-1H-benzo[e][1,4]diazepin-7-yl)pyridin-2(1H)-one, L-tartrate salt (12.4 mg, 98%, AUC HPLC>99%) as a white solid: $^1$H NMR (CD$_3$OD, 500 MHz) δ 7.66-7.63 (m, 2H), 7.56 (s, 1H), 7.41 (d, J=8.7 Hz, 1H), 7.29 (d, J=8.5 Hz, 1H), 7.22 (d, J=8.9 Hz, 2H), 6.91 (d, J=9.5 Hz, 1H), 6.53-6.50 (m, 1H), 4.43 (s, 1.2H), 4.17 (bs, 2H), 3.97 (bs, 2H), 3.44-3.42 (m, 1H), 3.17-3.15 (m, 1H), 2.79 (s, 3H); ESI MS m/z 398 [M+CH$_3$OH+H]$^+$.

Example 20

Preparation of 1-(4-chlorophenyl)-4-methyl-7-(pyridazin-3-yl)-2,3,4,5-tetrahydro-1H-benzo[e][1,4] diazepine, L-tartrate salt A procedure similar to the one in Example 18 was used to couple 4-methyl-7-(pyridazin-3-yl)-2,3,4,5-tetrahydro-1H-benzo[e][1,4]diazepine with 1-bromo-4-chlorobenzene. The desired free base was obtained in 50% yield as a colorless oil. A procedure similar to the one in Step I of Example 1 was used to obtain the L-tartrate salt in 87% yield as an off-white powder: $^1$H NMR (CD$_3$OD, 500 Hz) δ 9.16 (s, 1H), 8.30 (s, 1H), 8.22 (d, J=8.7 Hz, 1H), 8.11 (s, 1H), 7.81 (t, J=4.7 Hz, 1H), 7.31-7.25 (m, 3H), 6.98 (d, J=7.1, 2H), 4.43-4.40 (m, 4H), 4.02 (s, 2H), 3.44 (s, 2H), 2.91 (s, 3H); ESI MS m/z 351 [M+H]$^+$.

Example 21

Preparation of 1-(4-fluorophenyl)-4-methyl-7-(pyridazin-3-yl)-2,3,4,5-tetrahydro-1H-benzo[e][1,4] diazepine, L-tartrate salt A mixture of 4-methyl-7-(pyridazin-3-yl)-2,3,4,5-tetrahydro-1H-benzo[e][1,4]diazepine (48 mg, 0.2 mmol), 4-fluorophenylboronic acid (84 mg, 0.6 mmol), copper (II) acetate (54 mg, 0.3 mmol), triethylamine (61 mg, 0.6 mmol) and methylene chloride was stirred at room temperature for 1 day. The mixture was partitioned between methylene chloride (10 mL) and water (10 mL). The aqueous phase was extracted with methylene chloride (10 mL). The combined organic extract was dried over sodium sulfate, filtered and concentrated in vacuo. The residue was purified by column chromatography (100:0 to 90:10 methylene chloride/methanol) to give the desired free base (15 mg, 22%) as a yellow solid. A procedure similar to the one in Step I of Example 1 was used to obtain the L-tartrate salt in 88% yield as an off-white powder: $^1$H NMR (CD$_3$OD, 500 MHz) δ 9.15 (s, 1H), 8.25 (s, 1H), 8.19 (d, J=8.3 Hz, 1H), 8.04 (d, J=8.3 Hz, 1H), 7.80 (s, 1H), 7.11-7.05 (m, 5H), 4.43 (s, 4H), 4.00 (s, 2H), 3.44 (s, 2H), 2.92 (s, 3H); ESI MS m/z 335 [M+H]$^+$.

Example 22

Preparation of 4-methyl-7-(6-methylpyridazin-3-yl)-1-phenyl-2,3,4,5-tetrahydro-1H-benzo[e][1,4]diazepine, L-tartrate salt Step A: A mixture of 7-bromo-4-methyl-2,3,4,5-tetrahydro-1H-benzo[e][1,4]diazepine (1.20 g, 5 mmol), phenylboronic acid (1.83 g, 15 mmol), copper (II) acetate (1.36 g, 7.5 mmol) and triethylamine (1.52 g, 15 mmol) in methylene chloride (25 mL) was stirred at room temperature for 2 days. The mixture was partitioned between methylene chloride (50 mL) and water (50 mL). The aqueous phase was extracted with methylene chloride (50 mL). The combined organic extracts were dried over sodium sulfate, filtered and concentrated in vacuo. The residue was purified by column chromatography (methylene chloride, then 90:10 methylene chloride/methanol) to give the desired free base (0.92 g, 38%) as a yellow solid: $^1$H NMR (CDCl$_3$, 500 MHz) δ 7.45 (s, 1H), 7.37 (d, J=8.4 Hz, 1H), 7.19 (t, J=8.6 Hz, 2H), 7.04 (d, J=8.3 Hz, 1H), 6.79-6.72 (m, 3H), 3.72 (s, 2H), 3.49 (s, 2H), 2.88 (s, 2H), 2.36 (s, 3H); ESI MS m/z 318 [M+H]$^+$. A portion of the material was converted into the corresponding L-tartrate salt in 85% yield as an off-white powder using a procedure similar to the one in Step I of Example 1: $^1$H NMR (CD$_3$OD, 500 Hz) δ 7.70 (s, 1H), 7.52 (d, J=8.3 Hz, 1H), 7.26-7.22 (m, 2H), 7.05-7.02 (m, 1H), 6.87 (t, J=7.8 Hz, 3H), 4.44-4.40 (m, 2H), 4.17 (s, 2H), 3.93 (s, 2H), 2.77 (s, 3H); ESI MS m/z 318 [M+H]$^+$.

Step B: A round bottomed flask was charged with 7-bromo-4-methyl-1-phenyl-2,3,4,5-tetrahydro-1H-benzo[e][1,4]diazepine (0.22 g, 0.7 mmol) from step A above, bis(pinacolato) diboron (0.20 g, 0.77 mmol), potassium acetate (0.21 g, 2.1 mmol), dichloro[1,1'-bis(diphenylphosphino)ferrocene]palladium(II) dichloromethane adduct (57 mg, 0.07 mmol) and DMF (3.5 mL). The mixture was degassed with nitrogen (3×) and then stirred at 60° C. overnight. The mixture was cooled to room temperature, and cesium carbonate (0.68 g, 2.1 mmol), 3-chloro-6-methylpyridazine (0.14 g, 1.1 mmol) and water (1.8 mL) were added to it. The mixture was degassed with nitrogen (3×) and then stirred at 60° C. for 3 hours. After cooling, the mixture was partitioned between methylene chloride and water. The aqueous phase was extracted with methylene chloride (3×20 mL). The combined organic extract was dried over sodium sulfate, filtered and concentrated in vacuo. The residue was purified by column chromatography (methylene chloride, then 10:1 methylene chloride/methanol) to yield the desired 4-methyl-7-(6-methylpyridazin-3-yl)-1-phenyl-2,3,4,5-tetrahydro-1H-benzo[e][1,4]diazepine (0.16 g, 67%) as a grey solid.

Step C: A procedure similar to the one in Step I of Example 1 was used to obtain the L-tartrate salt in 82% yield as a yellow-green powder: $^1$H NMR (CD$_3$OD, 500 MHz) δ 8.25 (s, 1H), 8.10-8.02 (m, 2H), 7.69 (d, J=8.7 Hz, 1H), 7.31-7.22 (m, 3H), 7.02-6.95 (m, 3H), 4.42 (s, 4H), 4.04 (s, 2H), 3.44 (s, 2H), 2.94 (s, 3H), 2.73 (s, 3H); ESI MS m/z 331 [M+H]$^+$.

Example 23

Preparation of 1-(4-fluorophenyl)-4-methyl-7-(6-(trifluoromethyl)pyridazin-3-yl)-2,3,4,5-tetrahydro-1H-benzo[e][1,4]diazepine, L-tartrate salt Step A: A mixture of 7-bromo-4-methyl-2,3,4,5-tetrahydro-1H-benzo[e][1,4]diazepine (1.20 g, 5 mmol), 4-fluorophenylboronic acid (2.10 g, 15 mmol), copper (II) acetate (1.36 g, 7.5 mmol), triethylamine (1.52 g, 15 mmol) in methylene chloride (25 mL) was stirred at room temperature for 2 days. The mixture was partitioned between methylene chloride (50 mL) and water (50 mL). The aqueous phase was extracted with methylene chloride (50 mL). The combined organic extracts were dried over Na$_2$SO$_4$, filtered, and concentrated in vacuo. The residue was purified by column chromatography (100:0 to 90:10 methylene chloride/methanol) to give the desired free base (0.53 g, 32%) as a yellow solid: $^1$H NMR (CDCl$_3$, 500 MHz) δ 7.42 (s, 1H), 7.32 (d, J=9.0 Hz, 1H), 6.92-6.89 (m, 3H), 6.71-6.68 (m, 2H), 3.68-3.64 (m, 4H), 3.86 (t, J=4.8 Hz, 2H), 2.36 (s, 3H); ESI MS m/z 335 [M+H]$^+$.

Step B: A round bottomed flask was charged with 7-bromo-1-(4-fluorophenyl)-4-methyl-2,3,4,5-tetrahydro-1H-benzo[e][1,4]diazepine (75 mg, 0.22 mmol) from step A above, bis(pinacolato)diboron (62 mg, 0.25 mmol) and potassium acetate (66 mg, 0.67 mmol), and dichloro[1,1'-bis(diphenylphosphino)ferrocene]palladium(II) dichloromethane adduct (16 mg, 0.02 mmol) in DMF (1 mL). The mixture was refilled with nitrogen three times and then stirred at 65° C. overnight. The mixture was cooled to room temperature. Cesium carbonate (219 mg, 0.67 mmol), 3-chloro-6-trifluoromethylpyridazine (49 mg, 0.67 mmol), and water (0.5 mL) were added. The mixture was refilled with nitrogen three times and then stirred at 60° C. for 3 hours. After cooling, the mixture was partitioned between methylene chloride and water. The aqueous phase was extracted with methylene chloride (3×20 mL). The combined extracts were dried over sodium sulfate, filtered, and concentrated in vacuo. The residue was purified by column chromatography (100:0 to 10:1 methylene chloride/methanol) to yield the desired 1-(4-fluorophenyl)-4-methyl-7-(6-(trifluoromethyl)pyridazin-3-yl)-2,3,4,5-tetrahydro-1H-benzo[e][1,4]diazepine (71 mg, 79%) as a grey solid Step C: A procedure similar to the one in Step I of Example 1 was used to obtain the L-tartrate salt in 85% yield as a yellow-green powder: $^1$H NMR (CD$_3$OD, 500 MHz) δ 8.39-8.34 (m, 2H), 8.15-8.11 (m, 2H), 7.13-7.06 (m, 5H), 4.45-4.41 (m, 4H), 4.01 (s, br, 2H), 3.44 (s, br, 2H), 2.91 (s, 3H); ESI MS m/z 403 [M+H]$^+$.

Example 24

Preparation of 1-(4-methyl-1-(naphthalen-2-yl)-2,3,4,5-tetrahydro-1H-benzo[e][1,4]diazepin-7-yl)pyridin-2(1H)one, L-tartrate salt Step A: A mixture of 7-bromo-4-methyl-2,3,4,5-tetrahydro-1H-benzo[e][1,4]diazepine (2.3 g, 9.53 mmol), 2-bromonaphthalene (3.95 g, 19.1 mmol), 2-(dicyclohexylphosphino)-2',4',6'-tri-i-isopropyl-1,1'-biphenyl (450 mg, 0.953 mmol) and cesium carbonate (6.2 g, 19.1 mmol) in toluene (100 mL) was purged with argon for 10 minutes before palladium(II) acetate (214 mg, 0.953 mmol) was added to it. After purging with argon for 5 minutes, the reaction mixture was heated under reflux overnight. The mixture was cooled and partitioned between water (100 mL) and ethyl acetate (3×50 mL). The combined organic extract was dried over sodium sulfate, filtered and concentrated in vacuo. The residue was purified by flash chromatography (9:1 methylene chloride/methanol), followed by rechromatography, (3:1 methylene chloride/ethyl acetate) to yield the desired compound (850 mg, 25%) as a brown foam: $^1$H NMR (CDCl$_3$, 500 MHz) δ 7.70-7.59 (m, 3H), 7.48 (s, 1H), 7.39-7.35 (m, 2H), 7.27-7.24 (m, 1H), 7.70-6.98 (m, 3H), 3.84 (t, J=4.3 Hz, 2H), 3.66 (s, 2H), 2.93 (t, J=4.4 Hz, 2H), 2.39 (s, 3H); ESI MS m/z 367, 369 [M+H]$^+$.

Step B: A mixture of the bromobenzodiazepine (76 mg, 0.207 mmol) from Step A above, 2-hydroxypyridine (24 mg, 0.248 mmol), potassium phosphate (87 mg, 0.414 mmol) and N,N-dimethylethylenediamine (7.0 mg, 0.0827 mmol) in 1,4-dioxane (2.0 mL) was purged with argon for 10 minutes before copper(I) iodide (8.0 mg, 0.0413 mmol) was added to it. After purging with argon for 10 minutes, the sealed tube reaction was heated at 110° C. overnight. The reaction mixture was cooled and partitioned between water (50 mL) and ethyl acetate (3×50 mL). The combined organic extract was washed with brine (50 mL), dried over sodium sulfate, filtered and concentrated in vacuo. The residue was purified twice by flash chromatography (9:1 methylene chloride/methanol) to give the desired benzodiazepine (9.0 mg, 12%) as a white solid. To a solution of the benzodiazepine (9.0 mg, 0.024 mmol) in methanol (1 mL) and water (3 mL) was added L-tartaric acid (3.6 mg, 0.024 mmol), and the resultant solution was lyophilized overnight to give 1-(4-methyl-1-(naphthalene-2-yl)-2,3,4,5-tetrahydro-1H-benzo[e][1,4]diazepin-7-yl)pyridine-2(1H)one, L-tartrate salt (12.4 mg, 98%, AUC HPLC>99%) as a white solid: $^1$H NMR (CD$_3$OD, 500 MHz) δ 7.61-7.50 (m, 6H), 7.45-7.38 (m, 3H), 7.33-7.29 (m, 2H), 7.16 (d, J=2.5 Hz, 1H), 6.66 (d, J=9.1 Hz, 1H), 6.54-6.51 (m, 1H), 4.44 (s, 1.5H), 4.35 (s, 2H), 4.14 (bs, 2H), 3.44 (s, 2H), 2.91 (s, 3H); ESI MS m/z 414 [M+CH$_3$OH+H]$^+$.

Example 25

Preparation of 7-(4-(ethylsulfonyl)piperazin-1-yl)-4-methyl-1-(naphthalen-2-yl)-2,3,4,5-tetrahydro-1H-benzo[e][1,4]diazepine, L-tartrate salt A mixture of 7-bromo-4-methyl-1-(naphthalen-2-yl)-2,3,4,5-tetrahydro-1H-benzo[e][1,4]diazepine (100 mg, 0.272 mmol), 1-ethylsulfonylpiperazine (63 mg, 0.354 mmol), 2-(dicyclohexylphosphino)-2',4',6'-tri-i-isopropyl-1,1'-biphenyl (13 mg, 0.0272 mmol) and cesium carbonate (177 mg, 0.544 mmol) in toluene (2 mL) was purged with argon for 10 minutes before palladium(II) acetate (6.2 mg, 0.0272 mmol) was added. After purging with argon for 5 min, the reaction mixture was heated at reflux overnight. The mixture was cooled, partitioned with water (50 mL) and ethyl acetate (3×50 mL). The combined organic extracts were dried over sodium sulfate, filtered and concentrated in vacuo. The residue was purified by preparatory thin-layer chromatography eluting with 9:1 methylene chloride/methanol to give a viscous oil (47 mg, 37%). To a solution of the benzodiazepine (47 mg, 0.101 mmol) in methanol (1 mL) and water (3 mL) was added L-tartaric acid (15.2 mg, 0.101 mmol) and the resultant solution was lyophilized overnight to yield 7-(4-(ethylsulfonyl)piperazin-1-yl)-4-methyl-1-(naphthalen-2-yl)-2,3,4,5-tetrahydro-1H-benzo[e][1,4]diazepine, L-tartrate salt (60 mg, 94%, AUC HPLC>99%) as a light brown solid: $^1$H NMR (CDCl$_3$, 500 MHz) δ 7.68-7.65 (m, 2H), 7.60 (d, J=8.3 Hz, 1H), 7.35 (t, J=6.5 Hz, 1H), 7.24-7.18 (m, 3H), 7.13-7.09 (m, 2H), 7.01 (d, J=9.0 Hz, 1H), 4.40 (s, 1H), 3.96 (bs, 2H), 3.46-3.42 (m, 6H), 3.34-3.31 (m, 4H), 3.11 (q, J=7.4 Hz, 2H), 2.84 (s, 3H), 1.36 (t, J=7.2 Hz, 2H); ESI MS m/z 465 [M+H]$^+$.

Example 26

Preparation of 4-methyl-1-(naphthalen-2-yl)-7-(pyridin-3-yl)-2,3,4,5-tetrahydro-1H-benzo[e][1,4]diazepine, L-tartrate salt A mixture of 7-bromo-4-methyl-1-(naphthalen-2-yl)-2,3,4,5-tetrahydro-1H-benzo[e][1,4]diazepine (100 mg, 0.272 mmol), 3-pyridine-boronic acid (50 mg, 0.408 mmol), potassium phosphate (116 mg, 0.544 mmol) and 2-di-tert-butylphosphino-2',4',6'-tri-i-propyl-1,1'-biphenyl (4.6 mg, 0.0108 mmol) in n-butanol (1.5 mL) was purged with argon for 10 minutes before tris(dibenzylideneacetone)dipalladium (0) (2.5 mg, 0.0027 mmol) was added to it. After purging with argon for 10 minutes, the sealed tube reaction was heated at 110° C. overnight. The reaction mixture was cooled and filtered through a short pad of Celite. The filtrate was concentrated in vacuo and the residue was purified twice by flash chromatography (9:1 methylene chloride/methanol) to give the desired benzodiazepine (8.0 mg, 8%) as a white solid. To a solution of the benzodiazepine (8.0 mg, 0.022 mmol) in methanol (1 mL) and water (3 mL) was added L-tartaric acid (3.4 mg, 0.022 mmol) and the resultant solution was lyophilized overnight to give 4-methyl-1-(naphthalene-2-yl)-7-(pyridin-3-yl)-2,3,4,5-tetrahydro-1H-benzo[e][1,4]diazepine, L-tartrate salt (11.2 mg, 99%, AUC HPLC 96.0%) as a dark yellow solid: $^1$H NMR (CD$_3$OD, 500 MHz) δ 8.91 (s, 1H), 8.57 (d, J=4.2 Hz, 1H), 8.19 (d, J=7.9 Hz, 1H), 7.94 (s, 1H), 7.80-7.72 (m, 4H), 7.60-7.57 (m, 1H), 7.46-7.32 (m, 4H), 7.17 (d, J=8.9 Hz, 1H), 4.47 (s, 1.4H), 4.45 (s, 2H), 4.18 (bs, 2H), 3.50 (s, 2H), 2.97 (s, 3H); ESI MS m/z 366 [M+H]$^+$.

Example 27

Preparation of 4-methyl-1-(naphthalen-2-yl)-N-(pyrimidin-2-yl)-2,3,4,5-tetrahydro-1H-benzo[e][1,4]diazepin-7-amine, L-tartrate salt A mixture of 7-bromo-4-methyl-1-(naphthalen-2-yl)-2,3,4,5-tetrahydro-1H-benzo[e][1,4]diazepine (100 mg, 0.272 mmol), 2-aminopyrimidine (34 mg, 0.354 mmol), cesium carbonate (222 mg, 0.681 mmol) and 2-di-tert-butylphosphino-2',4',6'-tri-i-propyl-1,1'-biphenyl (12 mg, 0.0272 mmol) in DMF (2.0 mL) was purged with argon for 10 minutes before tris(dibenzylideneacetone)dipalladium(0) (7.5 mg, 0.0081 mmol) was added to it. After purging with argon for 10 minutes, the sealed tube reaction was heated at 110° C. overnight. The reaction mixture was cooled and partitioned between water (50 mL) and ethyl acetate (3×50 mL). The combined organic extract was washed with brine (50 mL), dried over sodium sulfate, filtered and concentrated in vacuo. The residue was purified twice by flash chromatography (9:1 methylene chloride/methanol) to give the desired benzodiazepine (17 mg, 17%) as a white solid. To a solution of the benzodiazepine (16.7 mg, 0.044 mmol) in methanol (1 mL) and water (3 mL) was added L-tartaric acid (6.5 mg, 0.044 mmol) and the resultant solution was lyophilized overnight to give 4-methyl-1-(naphthalene-2-yl)-N-(pyrimidin-2-yl)-2,3,4,5-tetrahydro-1H-benzo[e][1,4]diazepin-7-amine, L-tartrate salt (23.0 mg, 99%, AUC HPLC 97.4%) as a dark yellow solid: $^1$H NMR (CD$_3$OD, 500 MHz) δ 8.45 (d, J=4.9 Hz, 2H), 8.01 (d, J=2.0 Hz, 1H), 7.74-7.72 (d, J=8.6 Hz, 1H), 7.69 (d, J=8.9 Hz, 2H), 7.63 (d, J=8.3 Hz, 1H), 7.36 (t, J=7.2 Hz, 1H), 7.26-7.22 (m, 2H), 7.17 (s, 1H), 7.07 (d, J=12.5 Hz, 1H), 6.83 (d, J=4.8 Hz, 1H), 4.42 (s, 1.3H), 4.26 (s, 2H), 3.99 (bs, 2H), 3.44 (s, 2H), 2.91 (s, 3H); ESI MS m/z 382 [M+H]$^+$.

Example 28

Preparation of 4-methyl-1-(naphthalen-2-yl)-7-(pyrazin-2-yl)-2,3,4,5-tetrahydro-1H-benzo[e][1,4]diazepine, L-tartrate salt A mixture of 7-bromo-4-methyl-1-(naphthalen-2-yl)-2,3,4,5-tetrahydro-1H-benzo[e][1,4]diazepine (76 mg, 0.207 mmol) and 2-tributylstannnylpyrazine (92 mg, 0.248 mmol) in toluene (2.0 mL) was purged with argon for 10 minutes before tetrakis(triphenylphosphine)palladium(0) (12 mg, 0.010 mmol) was added to it. After purging with argon for 10 minutes, the sealed tube reaction was heated at 110° C. overnight. The reaction mixture was cooled and partitioned between water (50 mL) and ethyl acetate (3×50 mL). The combined organic extract was washed with brine (50 mL), dried over sodium sulfate, filtered and concentrated in vacuo. The residue was purified twice by flash chromatography (9:1 methylene chloride/methanol) to give the desired benzodiazepine (9.0 mg, 10%) as a white solid. To a solution of the benzodiazepine (9.0 mg, 0.024 mmol) in methanol (1 mL) and water (3 mL) was added L-tartaric acid (3.6 mg, 0.024 mmol) and the resultant solution was lyophilized overnight to give 4-methyl-1-(naphthalene-2-yl)-7-(pyrazin-2-yl)-2,3,4, 5-tetrahydro-1H-benzo[e][1,4]diazepine, L-tartrate salt (12.4 mg, 97%, AUC HPLC 97.3%) as a dark yellow solid: $^1$H NMR (CD$_3$OD, 500 MHz) δ 9.16 (s, 1H), 8.69 (s, 1H), 8.54 (d, J=2.5 Hz, 1H), 8.33 (d, J=2.5 Hz, 1H), 8.14 (d, J=8.6 Hz, 1H), 7.76-7.72 (m, 3H), 7.44-7.41 (m, 2H), 7.35-7.22 (m, 2H), 7.17 (d, J=8.9 Hz, 1H), 4.51 (s, 2H), 4.47 (s, 2.4H), 4.19 (bs, 2H), 3.53 (s, 2H), 2.99 (s, 3H); ESI MS m/z 367 [M+H]$^+$.

Example 29

Preparation of 4-methyl-7-(4-(methanesulfonyl)phenyl)-1-(naphthalen-2-yl)-2,3,4,5-tetrahydro-1H-benzo[e][1,4]diazepine, L-tartrate salt A mixture of 7-bromo-4-methyl-1-(naphthalen-2-yl)-2,3,4,5-tetrahydro-1H-benzo[e][1,4]diazepine (110 mg, 0.299 mmol), 4-(methanesulfonyl)phenylboronic acid (90 mg, 0.449 mmol), potassium bromide (107 mg, 0.898 mmol) and potassium hydroxide (50 mg, 0.898 mmol) in toluene (2.0 mL) was purged with argon for 10 minutes before tetrakis(triphenylphosphine)palladium(0) (17 mg, 0.015 mmol) was added to it. After purging with argon for 10 minutes, the sealed tube reaction was heated at 110° C. overnight. The reaction mixture was cooled and partitioned between water (50 mL) and ethyl acetate (3×50 mL). The combined organic extract was washed with brine (50 mL), dried over sodium sulfate, filtered and concentrated in vacuo. The residue was purified twice by flash chromatography eluting with methylene chloride/methanol (9:1) to give the desired benzodiazepine (23.0 mg, 17%) as a viscous oil. To a solution of the benzodiazepine (23.0 mg, 0.05 mmol) in methanol (1 mL) and water (3 mL) was added L-tartaric acid (8.0 mg, 0.05 mmol) and the resultant solution was lyophilized overnight to give 4-methyl-7-(4-(methanesulfonyl)phenyl)-1-(naphthalene-2-yl)-2,3,4,5-tetrahydro-1H-benzo[e][1,4]diazepine, L-tartrate salt (30.0 mg, 97%, AUC HPLC 97.2%) as a light yellow solid: $^1$H NMR (CD$_3$OD, 500 MHz) δ 8.05 (d, J=8.4 Hz, 2H), 7.95-7.92 (m, 3H), 7.79-7.69 (m, 4H), 7.43-7.40 (m, 1H), 7.36 (s, 1H), 7.32-7.28 (m, 2H), 7.15 (d, J=2.5 Hz, 1H), 4.43 (s, 1.5H), 4.39 (s, 2H), 3.44 (bs, 2H), 3.16 (bs, 2H), 3.16 (s, 3H), 2.91 (s, 3H); ESI MS m/z 443 [M+H]$^+$.

Example 30

Preparation of 4-methyl-1-(naphthalen-2-yl)-7-(1H-pyrazol-1-yl)-2,3,4,5-tetrahydro-1H-benzo[e][1,4]diazepine, L-tartrate salt A mixture of 7-bromo-4-methyl-1-(naphthalen-2-yl)-2,3,4,5-tetrahydro-1H-benzo[e][1,4]diazepine (100 mg, 0.272 mmol), pyrazole (37 mg, 0.544 mmol), L-proline (13 mg, 0.109 mmol) and potassium carbonate (113 mg, 0.816 mmol) in DMSO (1.5 mL) was purged with argon for 10 minutes before copper(I) iodide (10 mg, 0.015 mmol) was added to it. After purging with argon for 10 minutes, the sealed tube reaction was heated at 110° C. overnight. The reaction mixture was cooled and partitioned between water (50 mL) and ethyl acetate (3×50 mL). The combined organic extract was washed with brine (50 mL), dried over sodium sulfate, filtered and concentrated in vacuo. The residue was purified twice by flash chromatography (9:1 methylene chloride/methanol) to give the desired benzodiazepine (22.8 mg, 24%) as a viscous oil. To a solution of the benzodiazepine (22.8 mg, 0.06 mmol) in methanol (1 mL) and water (3 mL) was added L-tartaric acid (8.0 mg, 0.06 mmol) and the resultant solution was lyophilized overnight to give 4-methyl-1-(naphthalene-2-yl)-7-(1H-pyrazol-1-ly)-2,3,4,5-tetrahydro-1H-benzo[e][1,4]diazepine, L-tartrate salt (32.0 mg, 97%, AUC HPLC %) as a light yellow solid: $^1$H NMR (CD$_3$OD, 500 MHz) δ 8.26 (s, 1H), 8.00 (s, 1H), 7.82 (d, J=8.6 Hz, 1H), 7.76-7.72 (m, 3H), 7.69 (d, J=8.3 Hz, 1H), 7.41-7.38 (m, 1H), 7.32-7.27 (m, 3H), 7.11 (d, J=8.9 Hz, 1H), 6.56 (s, 1H), 4.46 (s, 2H), 4.40 (s, 2H), 4.14 (bs, 2H), 3.49 (bs, 2H), 2.93 (s, 3H); ESI MS m/z 355 [M+H]$^+$.

Example 31

Preparation of 4-methyl-7-(6-methylpyridazin-3-yl)-1-(naphthalen-2-yl)-2,3,4,5-tetrahydro-1H-benzo[e][1,4]diazepine, L-tartrate salt-Boronate Ester Coupling of Heteroaryl Halides Step A: To a solution of 7-bromo-4-methyl-1-(naphthalen-2-yl)-2,3,4,5-tetrahydro-1H-benzo[e][1,4]diazepine (100 mg, 0.272 mmol), bis(pinacolato)diboron (76 mg, 0.299 mmol) and potassium acetate (80 mg, 0.817 mmol) in DMSO (2 mL) was purged with argon for 10 minutes before dichloro[1,1'-bis(diphenylphosphino)ferrocene]palladium(II) dichloromethane adduct (23 mg, 0.0272 mmol) was added to it. After 10 minutes of purging with argon, the reaction mixture was stirred for 2 hours at 80° C. under argon. The mixture was partitioned between water (50 mL) and ethyl acetate (3×50 mL) and the combined organic extract was washed with brine (50 mL), dried over sodium sulfate, filtered and concentrated in vacuo to give a purple oil used directly in the next reaction without purification.

Step B: To a solution of the boronate ester from Step A above in DMF (2.0 mL) and water (0.5 mL) were added cesium carbonate (266 mg, 0.817 mmol), 3-methyl-6-chloropyridazine (39 mg, 0.299 mmol) and dichloro[1,1'-bis(diphenylphosphino)ferrocene]palladium(II) dichloromethane adduct (23 mg, 0.0272 mmol) and water (0.5 mL). The reaction was then heated for 2 hours and then partitioned between water (50 mL) and ethyl acetate (3×50 mL). The combined organic extract was washed with brine (50 mL), dried over sodium sulfate, filtered and concentrated in vacuo. The residue was purified twice by flash chromatography (9:1 methylene chloride/methanol) to give the desired benzodiazepine (19 mg, 25%) as a yellow solid. To a solution of the benzodiazepine (19 mg, 0.1 mmol) in methanol (1 mL) and water (3 mL) was added L-tartaric acid (7.6 mg, 0.1 mmol) and the resultant solution was lyophilized overnight to give 4-methyl-7-(6-methylpyridazin-3-yl)-1-(naphthalene-2-yl)-2,3,4,5-tetrahydro-1H-benzo[e][1,4]diazepine, L-tartrate salt (26.5 mg, 99%, AUC HPLC 96.6%) as a yellow solid: $^1$H NMR (CD$_3$OD, 500 MHz) δ 8.29 (s, 1H), 8.11-8.06 (m, 2H), 7.76-7.68 (m, 4H), 7.43-7.40 (m, 2H), 7.33-7.28 (m, 2H), 7.17 (d, J=8.9 Hz, 1H), 4.43 (s, 1.5H), 4.39 (s, 2H), 4.13 (bs, 2H), 3.43 (s, 2H), 2.91 (s, 3H), 2.74 (s, 3H); ESI MS m/z 381 [M+H]$^+$.

Example 32

Preparation of 7-([1,2,4]triazolo[1,5-a]pyridin-6-yl)-4-methyl-1-(naphthalen-2-yl)-2,3,4,5-tetrahydro-1H-benzo[e][1,4]diazepine, L-tartrate salt Following a procedure similar to the one in Example 31, 4-methyl-1-(naphthalen-2-yl)-7-(4,4,5,5-tetramethyl-1,3,2-dioxaborolan-2-yl)-2,3,4,5-tetrahydro-1H-benzo[e][1,4]diazepine (92 mg, 0.222 mmol), 6-bromo-[1,2,4]triazolo[1,5-a]pyridine (53 mg, 0.266 mmol), cesium carbonate (216 mg, 0.666 mmol) and dichloro[1,1'-bis(diphenylphosphino)ferrocene]palladium(II) dichloromethane adduct (18 mg, 0.0222 mmol) in DMF (2.0 mL) and water (0.5 mL) gave the desired product (22.8 mg, 25%) as a colorless oil. To a solution of the benzodiazepine (22.8 mg, 0.06 mmol) in methanol (1 mL) and water (3 mL) was added L-tartaric acid (8.7 mg, 0.06 mmol) and the resultant solution was lyophilized overnight to give 7-([1,2,4]triazolo[1,5-a]pyridine-6-yl)-4-methyl-1-(naphthalene-2-yl)-2,3,4,5-tetrahydro-1H-benzo[e] diazepine, L-tartrate salt (30.0 mg, 94%, AUC HPLC 96.2%) as an off-white solid: $^1$H NMR (CD$_3$OD, 500 MHz) δ 9.14 (s, 1H), 8.45 (s, 1H), 8.08 (d, J=7.6 Hz, 1H), 7.94 (s, 1H), 7.89 (s, 9.2 Hz, 1H), 7.79 (d, J=8.3 Hz, 1H), 7.73 (d, J=9.0 Hz, 2H), 7.69 (d, J=8.5 Hz, 1H), 7.41-7.38 (m, 1H), 7.35-7.29 (m, 3H), 7.14 (d, J=8.9 Hz, 1H), 4.42 (s, 1.2H), 4.34 (s, 2H), 4.13 (bs, 2H), 3.41 (bs, 2H), 2.88 (s, 3H); ESI MS m/z 406 [M+H]$^+$.

Example 33

Preparation of 7-([1,2,4]triazolo[4,3-a]pyridin-6-yl)-4-methyl-1-(naphthalen-2-yl)-2,3,4,5-tetrahydro-1H-benzo[e][1,4]diazepine, L-tartrate salt Following a procedure similar to the one in Example 31, 4-methyl-1-(naphthalen-2-yl)-7-(4,4,5,5-tetramethyl-1,3,2-dioxaborolan-2-yl)-2,3,4,5-tetrahydro-1H-benzo[e][1,4]diazepine (92 mg, 0.222 mmol), 6-bromo-[1,2,4]triazolo[4,3-a]pyridine (53 mg, 0.266 mmol), cesium carbonate (216 mg, 0.666 mmol) and dichloro[1,1'-bis(diphenylphosphino)ferrocene]palladium(II) dichloromethane adduct (18 mg, 0.0222 mmol) in DMF (2.0 mL) and water (0.5 mL) gave the desired product (28.6 mg, 32%) as a colorless oil. To a solution of the benzodiazepine (28.6 mg, 0.07 mmol) in methanol (1 mL) and water (3 mL) was added L-tartaric acid (10.9 mg, 0.07 mmol) and the resultant solution was lyophilized overnight to give 7-([1,2,4]triazolo[4,3-a]pyridine-6-yl)-4-methyl-1-(naphthalene-2-yl)-2,3,4,5-tetrahydro-1H-benzo[e] diazepine, L-tartrate salt (38.0 mg, 96%, AUC HPLC>99%) as a light yellow solid: $^1$H NMR (CD$_3$OD, 500 MHz) δ 9.23 (s, 1H), 8.83 (s, 1H), 7.91 (s, 1H), 7.87 (s, 2H), 7.78-7.69 (m, 4H), 7.42-7.39 (s, 1H), 7.36 (d, J=2.2 Hz, 1H), 7.32-7.29 (m, 2H), 7.15 (d, J=2.6 Hz, 1H), 4.45 (s, 1.6H), 4.39 (s, 2H), 4.15 (bs, 2H), 3.45 (bs, 2H), 2.92 (s, 3H); ESI MS m/z 406 [M+H]$^+$.

Example 34

Preparation of 4-methyl-1-(naphthalen-2-yl)-7-(pyrimidin-5-yl)-2,3,4,5-tetrahydro-1H-benzo[e][1,4] diazepine, L-tartrate salt Following a procedure similar to the one in Example 31, 4-methyl-1-(naphthalen-2-yl)-7-(4,4,5,5-tetramethyl-1,3,2-dioxaborolan-2-yl)-2,3,4,5-tetrahydro-1H-benzo[e][1,4]diazepine (92 mg, 0.22 mmol), 5-bromopyrimidine (42 mg, 0.266 mmol), cesium carbonate (216 mg, 0.66 mmol) and dichloro[1,1'-bis(diphenylphosphino)ferrocene]palladium(II) dichloromethane adduct (18 mg, 0.022 mmol) in DMF (2.0 mL) and water (0.5 mL) gave the desired product (29.5 mg, 36%) as a colorless oil. To a solution of the benzodiazepine (29.5 mg, 0.08 mmol) in methanol (1 mL) and water (3 mL) was added L-tartaric acid (12.5 mg, 0.08 mmol) and the resultant solution was lyophilized overnight to give 4-methyl-1-(naphthalene-2-yl)-7-(pyrimidin-5-yl)-2,3,4,5-tetrahydro-1H-benzo[e]diazepine, L-tartrate salt (38.0 mg, 96%, AUC HPLC>99%) as a light yellow solid: $^1$H NMR (CD$_3$OD, 500 MHz) δ 9.16 (s, 1H), 9.13 (s, 2H), 7.94 (s, 1H), 7.80-7.70 (m, 4H), 7.43-7.38 (m, 2H), 7.33-7.30 (m, 2H), 7.16 (d, J=8.9 Hz, 1H), 4.44 (s, 1.3H), 4.38 (s, 2H), 4.14 (bs, 2H), 3.44 (bs, 2H), 2.91 (s, 3H); ESI MS m/z 367 [M+H]$^+$.

Example 35

Preparation of 4-methyl-1-(naphthalen-2-yl)-7-(pyrimidin-2-yl)-2,3,4,5-tetrahydro-1H-benzo[e][1,4] diazepine, L-tartrate salt Following a procedure similar to the one in Example 31, 4-methyl-1-(naphthalen-2-yl)-7-(4,4,5,5-tetramethyl-1,3,2-dioxaborolan-2-yl)-2,3,4,5-tetrahydro-1H-benzo[e][1,4]diazepine (92 mg, 0.22 mmol), 2-bromopyrimidine (42 mg, 0.266 mmol), cesium carbonate (216 mg, 0.66 mmol) and dichloro[1,1'-bis(diphenylphosphino)ferrocene]palladium(II) dichloromethane adduct (18 mg, 0.022 mmol) in DMF (2.0 mL) and water (0.5 mL) gave the desired product (26.0 mg, 32%) as a colorless oil. To a solution of the benzodiazepine (26.0 mg, 0.07 mmol) in methanol (1 mL) and water (3 mL) was added L-tartaric acid (11.0 mg, 0.07 mmol) and the resultant solution was lyophilized overnight to give 4-methyl-1-(naphthalene-2-yl)-7-(pyrimidin-2-yl)-2,3,4,5-tetrahydro-1H-benzo[e]diazepine, L-tartrate salt (36.9 mg, 99%, AUC HPLC>99%) as a light yellow solid: $^1$H NMR (CD$_3$OD, 500 MHz) δ 8.85 (d, J=4.5 Hz, 2H), 8.60 (d, J=1.5 Hz, 1H), 8.43 (dd, J=8.5, 2.0 Hz, 1H), 7.75 (d, J=8.5 Hz, 2H), 7.72 (d, J=8.0 Hz, 1H), 7.43-7.42 (m, 2H), 7.36 (t, J=5.0 Hz, 1H), 7.34-7.31 (m, 2H), 7.24 (d, J=8.5 Hz, 1H), 7.17 (dd, J=9.0 Hz, 1H), 4.46 (s, 2H), 4.43 (s, 2H), 4.16 (bs, 2H), 3.48 (m, 2H), 2.95 (s, 3H).

Example 36

Preparation of 1-(4-chlorophenyl)-4-methyl-7-(pyrazin-2-yl)-2,3,4,5-tetrahydro-1H-benzo[e][1,4] diazepine, L-tartrate salt Step A: A solution of 7-bromo-1-(4-chlorophenyl)-4-methyl-2,3,4,5-tetrahydro-1H-benzo[e][1,4]diazepine (694 mg, 1.97 mmol), bis(pinacolato)diboron (551 mg, 2.17 mmol) and potassium acetate (580 mg, 5.92 mmol) in DMSO (10 mL) was purged with argon for 10 minutes before dichloro [1,1'-bis(diphenylphosphino)ferrocene]palladium(II) dichloromethane adduct (160 mg, 0.197 mmol) was added. After 10 minutes of purging with argon, the reaction mixture was stirred for 2 hours at 80° C. under argon. The mixture was partitioned with water (50 mL) and ethyl acetate (3×50 mL) and the combined organic extracts were washed with brine (50 mL), dried over sodium sulfate, filtered and concentrated in vacuo to give a purple oil used directly in the next reaction without purification.

Step B: To a solution of the boronate ester (100 mg, 0.251 mmol) from Step A above were added cesium carbonate (245 mg, 0.752 mmol), 2-chloropyrazine (34 mg, 0.301 mmol), and dichloro[1,1'-bis(diphenylphosphino)ferrocene]palladium(II) dichloromethane adduct (20 mg, 0.0251 mmol) in DMF (2.0 mL) and water (0.5 mL). The reaction was then heated for 2 hours, partitioned with water (50 mL) and ethyl acetate (3×50 mL). The combined organic extracts were washed with brine (50 mL), dried over sodium sulfate, filtered, and concentrated in vacuo. The residue was purified twice by preparatory thin-layer chromatography eluting with methylene chloride/methanol (10:1) to give the desired benzodiazepine (14.0 mg, 16%) as a yellow solid. To a solution of the benzodiazepine (14.0 mg, 0.040 mmol) in methanol (1 mL) and water (3 mL) was added L-tartaric acid (7.0 mg, 0.040 mmol) and the resultant solution was lyophilized overnight to give 1-(4-chlorophenyl)-4-methyl-7-(pyrazin-2-yl)-

2,3,4,5-tetrahydro-1H-benzo[e][1,4]diazepine, L-tartrate salt (19.3 mg, 95%, AUC HPLC 98%) as a yellow solid: $^1$H NMR (CD$_3$OD, 500 MHz) δ 9.14 (s, 1H), 8.68 (d, J=1.3 Hz, 1H), 8.53 (d, J=2.5 Hz, 1H), 8.27 (s, 1H), 8.13 (d, J=8.5 Hz, 1H), 7.27 (d, J=8.4 Hz, 1H), 7.25 (d, J=8.9 Hz, 2H), 6.94 (d, J=9.0 Hz, 2H), 4.44 (s, 1.4H), 4.32 (s, 2H), 3.99 (bs, 2H), 3.34 (bs, 2H), 2.87 (s, 3H); ESI MS m/z 351 [M+H]$^+$.

Example 37

Preparation of 1-(4-chlorophenyl)-4-methyl-7-(4-(methylsulfonyl)phenyl)-2,3,4,5-tetrahydro-1H-benzo[e][1,4]diazepine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 4-(methanesulfonyl)bromobenzene (76 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (11.2 mg, 11%) as a colorless oil. To a solution of the benzodiazepine (11.2 mg, 0.026 mmol) in methanol (1 mL) and water (3 mL) was added L-tartaric acid (4.1 mg, 0.026 mmol) and the resultant solution was lyophilized overnight to give 1-(4-chlorophenyl)-4-methyl-7-(4-(methylsulfonyl)phenyl)-2,3,4,5-tetrahydro-1H-benzo[e][1,4]diazepine, L-tartrate salt (15.0 mg, 98%, AUC HPLC>99%) as a yellow solid: $^1$H NMR (CD$_3$OD, 500 MHz) δ 8.04 (d, J=8.3 Hz, 2H), 7.92 (d, J=8.4 Hz, 2H), 7.88 (s, 1H), 7.76 (d, J=8.3 Hz, 1H), 7.28 (d, J=8.3 Hz, 1H), 7.22 (d, J=9.0 Hz, 2H), 6.89 (d, J=8.9 Hz, 2H), 4.43 (s, 1H), 4.21 (s, 2H), 3.96 (bs, 2H), 3.44 (bs, 2H), 3.17 (s, 3H), 2.84 (s, 3H); ESI MS m/z 427 [M+H]$^+$.

Example 38

Preparation of 1-(4-chlorophenyl)-4-methyl-7-(pyrimidin-5-yl)-2,3,4,5-tetrahydro-1H-benzo[e][1,4]diazepine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 5-bromopyrimidine (47 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (21.0 mg, 24%) as a colorless oil. To a solution of the benzodiazepine (21.0 mg, 0.06 mmol) in methanol (1 mL) and water (3 mL) was added L-tartaric acid (9.0 mg, 0.06 mmol) and the resultant solution was lyophilized overnight to give 4-methyl-1-(naphthalene-2-yl)-7-(pyrimidin-5-yl)-2,3,4,5-tetrahydro-1H-benzo[e]diazepine, L-tartrate salt (26.9 mg, 99%, AUC HPLC>99%) as a light brown solid: $^1$H NMR (CD$_3$OD, 500 MHz) δ 9.16 (s, 1H), 9.12 (s, 2H), 7.90 (s, 1H), 7.78 (d, J=6.2 Hz, 1H), 7.30 (d, J=8.4 Hz, 1H), 7.24 (d, J=8.9 Hz, 2H), 6.92 (d, J=8.9 Hz, 2H), 4.45 (s, 1.7H), 4.29 (s, 2H), 3.99 (bs, 2H), 3.40-4.36 (m, 2H), 2.85 (s, 3H); ESI MS m/z 351 [M+H]$^+$.

Example 39

Preparation of 1-(4-chlorophenyl)-4-methyl-7-(pyrimidin-2-yl)-2,3,4,5-tetrahydro-1H-benzo[e][1,4]diazepine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 2-bromopyrimidine (47 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (12.1 mg, 14%) as a colorless oil. To a solution of the benzodiazepine (12.1 mg, 0.034 mmol) in methanol (1 mL) and water (3 mL) was added L-tartaric acid (5.2 mg, 0.034 mmol) and the resultant solution was lyophilized overnight to give 1-(4-chlorophenyl)-4-methyl-7-(pyrimidin-2-yl)-2,3,4,5-tetrahydro-1H-benzo[e]diazepine, L-tartrate salt (17.0 mg, 98%, AUC HPLC>99%) as a yellow solid: $^1$H NMR (CD$_3$OD, 500 MHz) δ 8.85 (s, 2H), 8.56 (s, 1H), 8.43 (d, J=8.4 Hz, 1H), 7.36 (d, J=4.9 Hz, 1H), 7.26-7.23 (m, 3H), 6.94 (d, J=9.0 Hz, 2H), 4.43 (s, 1.2H), 4.31 (s, 2H), 3.92 (bs, 2H), 3.35-3.33 (m, 2H), 2.82 (s, 3H); ESI MS m/z 351 [M+H]$^+$.

Example 40

Preparation of 4-(1-(4-chlorophenyl)-4-methyl-2,3,4,5-tetrahydro-1H-benzo[e][1,4]diazepin-7-yl)benzamide, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 4-bromobenzamide (60 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (10.0 mg, 10%) as a colorless oil. To a solution of the benzodiazepine (10.0 mg, 0.025 mmol) in methanol (1 mL) and water (3 mL) was added L-tartaric acid (4.0 mg, 0.025 mmol) and the resultant solution was lyophilized overnight to give 4-(1-(4-chlorophenyl)-4-methyl-2,3,4,5-tetrahydro-1H-benzo[e][1,4]diazepin-7-yl)benzamide, L-tartrate salt (13.6 mg, 97%, AUC HPLC>99%) as a yellow solid: $^1$H NMR (CD$_3$OD, 500 MHz) δ 7.97 (d, J=8.4 Hz, 2H), 7.87 (s, 1H), 7.78-7.75 (m, 3H), 7.28 (d, J=8.3 Hz, 1H), 7.22 (d, J=9.0 Hz, 2H), 6.89 (d, J=9.0 Hz, 2H), 4.43 (s, 1.3H), 4.27 (s, 2H), 3.98 (bs, 2H), 3.35-3.33 (m, 2H), 2.86 (s, 3H); ESI MS m/z 392 [M+H]$^+$.

Example 41

Preparation of 7-([1,2,4]triazolo[1,5-a]pyridin-6-yl)-1-(4-chlorophenyl)-4-methyl-2,3,4,5-tetrahydro-1H-benzo[e][1,4]diazepine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 6-bromo-[1,2,4]triazolo[1,5-a]pyridine (60 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (10.1 mg, 10%) as a colorless oil. To a solution of the benzodiazepine (10.1 mg, 0.026 mmol) in methanol (1 mL) and water (3 mL) was added L-tartaric acid (4.0 mg, 0.026 mmol) and the resultant solution was lyophilized overnight to give 7-([1,2,4]triazolo[1,5-a]pyridin-6-yl)-1-(4-chlorophenyl)-4-methyl-2,3,4,5-tetrahydro-1H-benzo[e][1,4]diazepine, L-tartrate salt (13.8 mg, 98%, AUC HPLC 96.9%) as an off-white solid: $^1$H NMR (CD$_3$OD, 500 MHz) δ 9.12 (s, 1H), 8.46 (s, 1H), 8.05 (d, J=9.3 Hz, 1H), 7.91-7.88

(m, 2H), 7.79 (d, J=8.3 Hz, 1H), 7.31 (d, J=8.3 Hz, 1H), 7.24 (d, J=9.0 Hz, 2H), 6.90 (d, J=9.0 Hz, 2H), 4.44 (s, 1.5H), 4.28 (s, 2H), 3.99 (bs, 2H), 3.35-3.33 (m, 2H), 2.87 (s, 3H); ESI MS m/z 390 [M+H]$^+$.

Example 42

Preparation of 7-([1,2,4]triazolo[4,3-a]pyridin-6-yl)-1-(4-chlorophenyl)-4-methyl-2,3,4,5-tetrahydro-1H-benzo[e][1,4]diazepine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 6-bromo-[1,2,4]triazolo[4,3-a]pyridine (60 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (10.0 mg, 10%) as a colorless oil. To a solution of the benzodiazepine (10.0 mg, 0.026 mmol) in methanol (1 mL) and water (3 mL) was added L-tartaric acid (10.9 mg, 0.026 mmol) and the resultant solution was lyophilized overnight to give 7-([1,2,4]triazolo[4,3-a]pyridin-6-yl)-1-(4-chlorophenyl)-4-methyl-2,3,4,5-tetrahydro-1H-benzo[e][1,4]diazepine, L-tartrate salt (13.2 mg, 94%, AUC HPLC 94.7%) as a brown solid: $^1$H NMR (CD$_3$OD, 500 MHz) δ 9.23 (s, 1H), 8.82 (s, 1H), 7.88 (s, 1H), 7.84 (s, 2H), 7.77 (d, J=6.4 Hz, 1H), 7.30 (d, J=8.3 Hz, 1H), 7.24 (d, J=9.0 Hz, 2H), 6.91 (d, J=9.0 Hz, 2H), 4.46 (s, 1.7H), 4.33 (s, 2H), 4.00 (bs, 2H), 3.40-3.38 (m, 2H), 2.90 (s, 3H); ESI MS m/z 390 [M+H]$^+$.

Example 43

Preparation of 6-(1-(4-chlorophenyl)-4-methyl-2,3,4,5-tetrahydro-1H-benzo[e][1,4]diazepin-7-yl)pyridazin-3-amine, L-tartrate salt Following a procedure similar to the one in Example 36, 1-(4-chlorophenyl)-4-methyl-7-(4,4,5,5-tetramethyl-1,3,2-dioxaborolan-2-yl)-2,3,4,5-tetrahydro-1H-benzo[e][1,4]diazepine (100 mg, 0.251 mmol), 3-amino-6-chloropyridazine (40 mg, 0.301 mmol), cesium carbonate (245 mg, 0.752 mmol) and dichloro[1,1'-bis(diphenylphosphino)ferrocene]palladium(II) dichloromethane adduct (20 mg, 0.0251 mmol) in DMF (2.0 mL) and water (0.5 mL) gave the desired product (6.0 mg, 7%) as a colorless oil. To a solution of the benzodiazepine (6.0 mg, 0.016 mmol) in methanol (1 mL) and water (3 mL) was added L-tartaric acid (2.0 mg, 0.016 mmol) and the resultant solution was lyophilized overnight to give 6-(1-(4-chlorophenyl)-4-methyl-2,3,4,5-tetrahydro-1H-benzo[e][1,4]diazepin-7-yl)pyridazin-3-amine, L-tartrate salt (7.2 mg, 90%, AUC HPLC 97.0%) as a yellow solid: $^1$H NMR (CD$_3$OD, 500 MHz) δ 8.10 (s, 1H), 7.93 (d, J=8.4 Hz, 1H), 7.85 (d, J=9.3 Hz, 2H), 7.26 (d, J=8.4 Hz, 1H), 7.22 (d, J=6.1 Hz, 2H), 7.06 (d, J=9.4 Hz, 1H), 6.90 (d, J=9.1 Hz, 1H). 4.49 (s, 1.5H), 4.31 (s, 2H), 3.98 (bs, 2H), 3.38-3.34 (m, 2H), 2.89 (s, 3H); ESI MS m/z 366 [M+H]$^+$.

Example 44

Primary Binding Assay

Preparation of Membranes

Recombinant HEK-293 cells expressing either the hSERT, hDAT, or hNET proteins were harvested from T-175 flasks as follows. The medium was removed from the flasks and the cells rinsed with HBSS without Ca and without Mg. The cells were then incubated for 5-10 minutes in 10 mM Tris-Cl, pH 7.5, 5 mM EDTA before the cells were lifted with a combination of pipetting and scraping, as needed. The cell suspension was collected into centrifuge bottles and homogenized for 30 seconds with a Polytron homogenizer. The suspension was centrifuged for 30 minutes at 32,000×g, 4° C. The supernatant was decanted and the pellet resuspended and homogenized in 50 mM Tris-Cl, pH 7.5, 1 mM EDTA for 10 seconds. The suspension was then centrifuged again for 30 minutes at 32,000×g, 4° C. The supernatant was decanted and the pellet resuspended in 50 mM Tris-Cl, pH 7.5, 1 mM EDTA and briefly homogenized. A Bradford assay (Bio-rad) was performed and the membrane preparation diluted to 2 mg/ml with 50 mM Tris-Cl, pH 7.5, 1 mM EDTA. Aliquots were prepared, and then frozen and stored at −80° C.

SERT Radioligand Binding Assay

Compounds were dissolved in 100% DMSO at a concentration 100 times the desired highest assay concentration, serially diluted 1:3 in 100% DMSO, and 0.4 μl/well of each solution esd dispensed to a Nunc polypropylene, round bottom, 384-well plate. 100% inhibition is defined with 0.4 μl/well of 1 mM fluoxetine dissolved in DMSO. 20 μl/well of a 2× membrane preparation (15 μg/ml in 50 mM Tris-Cl, pH 7.5, 120 mM NaCl, 5 mM KCl) and 20 μl/well of a 2× radioligand solution (520 μM [$^{125}$I]RTI-55 in 50 mM Tris-Cl, pH 7.5, 120 mM NaCl, 5 mM KCl) were added to each well and the reaction incubated for 1 hour at room temperature. The contents of the assay plate were then transferred to a Millipore Multiscreen$_{HTS}$ GF/B filter plate which has been pretreated with 0.5% PEI for at least one hour. The plate was vacuum filtered and washed with 7 washes of 100 μl/well 50 mM Tris-Cl, pH 7.5, 120 mM NaCl, 5 mM KCl chilled to 4° C. The filtration and washing was completed in less than 90 seconds. The plates were air-dried overnight, 12 μl/well of MicroScint scintillation fluid added, and the plates counted in a Trilux.

DAT Radioligand Binding Assay

Compounds were dissolved in 100% DMSO at a concentration 100 times the desired highest assay concentration, serially diluted 1:3 in 100% DMSO, and 0.4 μl/well of each solution was dispensed to a Nunc polypropylene, round bottom, 384-well plate. 100% inhibition is defined with 0.4 μl/well of 1 mM GBR-12935 dissolved in DMSO. 20 μl/well of a 2× membrane preparation (12.5 μg/ml in 30 mM sodium phosphate buffer, pH 7.9 at 4° C.) and 20 μl/well of a 2× radioligand solution (250 μM [$^{125}$I]RTI-55 in 30 mM sodium phosphate buffer, pH 7.9 at 4° C.) were added to the well and the reaction incubated for 1 hour at room temperature. The contents of the assay plate were then transferred to a Millipore Multiscreen$_{HTS}$ GF/B filter plate which had been pretreated with 0.5% PEI for at least one hour. The plate was vacuum-filtered and washed with 7 washes of 100 μl/well 50 mM Tris-Cl, pH 7.5, 120 mM NaCl, 5 mM KCl chilled to 4° C. The filtration and washing were completed in less than 90 seconds. The plates were air-dried overnight, 12 μl/well of MicroScint scintillation fluid added, and the plates counted in a Trilux.

NET Radioligand Binding Assay

Compounds were dissolved in 100% DMSO at a concentration 100× the desired highest assay concentration, serially diluted 1:3 in 100% DMSO, and 1.0 μl/well of each solution was dispensed to a Nunc polypropylene, round bottom, 384-well plate. 100% inhibition is defined with 1.0 μl/well of 10 mM desipramine dissolved in DMSO. 50 μl/well of a 2× membrane preparation (0.4 mg/ml in 50 mM Tris-Cl, pH 7.5, 120 mM NaCl, 5 mM KCl) and 50 μl/well of a 2× radioligand solution (4 nM [³H]nisoxetine in 50 mM Tris-Cl, pH 7.5, 120 mM NaCl, 5 mM KCl) were added to the well and the reaction incubated for 1 hour at room temperature. The contents of the assay plate were then transferred to a Millipore Multi-screen$_{HTS}$ GF/B filter plate which had been pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing is completed in less than 90 seconds. The plates were air-dried overnight, 12 µl/well of MicroScint scintillation fluid added, and the plates counted in a Trilux.

Data Analysis

The raw data is normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, Y=Bottom+(Top-Bottom)/(1+10^((LogIC$_{50}$−X)*HillSlope)) in order to determine the IC$_{50}$ value for each compound. The radio ligand concentration chosen for each assay corresponds to the K$_d$ concentration determined through saturation binding analysis for each assay.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A compound of formulae I(A-D) having the following structure:

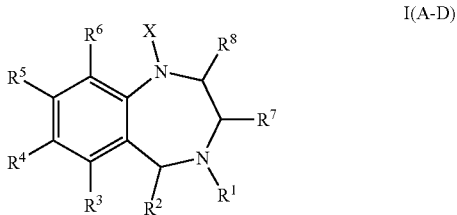

I(A-D)

wherein:

X represents a 5- or 6-membered aromatic monocyclic carbocycle or heterocycle selected from the group consisting of phenyl, pyridyl, 2-oxo-pyridin-1(2H)-yl, pyrimidinyl, pyridazinyl, pyrazinyl, triazinyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, substituted from 1 to 4 times with substituents as defined below in R$^9$, or other 5- or 6-membered aromatic monocyclic carbocycles or heterocycles containing 1-4 heteroatoms selected from the group consisting of oxygen, nitrogen, and sulfur, substituted from 1 to 4 times with substituents as defined below in R$^9$; or X is a [5,5]-, [6,5]-, [6,6]-, or [6,7]-fused bicyclic carbocycle or heterocycle selected from the group consisting of indenyl, benzofuranyl, benzothiophenyl, indolyl, isoindolyl, benzooxazolyl, benzothiazolyl, benzoisothiazolyl, benzoisoxazolyl, indazolyl, benzoimidazolyl, benzotriazolyl, naphthyl, quinolinyl, isoquinolinyl, quinazolinyl, cinnolinyl, phthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, imidazo[1,2-a]pyrazinyl, 3,3-dimethyl-2-oxoindolinyl, [1,2,4]triazolo[4,3-a]pyrazinyl, and 3-oxo-[1,2,4]triazolo[4,3-a]pyridin-2(3H)-yl, substituted from 1 to 4 times with substituents as defined below in R$^9$, or other [5,5]-, [6,5]-, [6,6]-, or [6,7]-fused bicyclic carbocycles or heterocycles containing 1-5 heteroatoms selected from the group consisting of oxygen, nitrogen, and sulfur, substituted from 1 to 4 times with substituents as defined below in R$^9$;

R$^1$ and R$^2$ are each independently selected from the group consisting of H, C$_1$-C$_6$ alkyl, C$_2$-C$_6$ alkenyl, C$_2$-C$_6$-alkynyl, C$_3$-C$_6$ cycloalkyl, and C$_4$-C$_7$ cycloalkylalkyl, each of which is optionally substituted from 1 to 3 times with substituents as defined below in R$^{10}$; or R$^2$ is gem-dimethyl;

R$^3$, R$^5$, and R$^6$ are each independently selected from the group consisting of H, halogen, —OR$^{11}$, —NR$^{12}$R$^{13}$, S(O)$_n$R$^{14}$, —CN, —C(O)R$^{15}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of the C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{10}$; or R$^3$, R$^5$, and R$^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in R$^9$;

R$^4$ is H, halogen, —OR$^{11}$, —NR$^{12}$R$^{13}$, —S(O)$_n$R$^{14}$, —CN, —C(O)R$^{15}$, C$_1$-C$_6$ alkyl, C$_2$-C$_6$ alkenyl, C$_2$-C$_6$ alkynyl, C$_3$-C$_6$ cycloalkyl, or C$_4$-C$_7$ cycloalkylalkyl, where each of the C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{10}$; or R$^4$ is an aromatic monocyclic or bicyclic carbocycle or an aromatic or non-aromatic monocyclic or bicyclic heterocycle selected from the group consisting of phenyl, pyridyl, 2-oxo-pyridin-1(2H)-yl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pynolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]

pyrazinyl, [1,2,4]triazolo[4,3-a]pyrazinyl, and 3-oxo-[1,2,4]triazolo[4,3-a]pyridin-2(3H)-yl, substituted from 1 to 4 times with substituents as defined below in $R^9$, or other 5- or 6-membered monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, substituted from 1 to 4 times with substituents as defined below in $R^9$;

provided that for compounds of formula IA, X is substituted phenyl and $R^4$ is substituted aromatic monocyclic or bicyclic carbocycle or heterocycle;

provided that for compounds of formula IB, X is substituted aromatic bicyclic carbocycle or heterocycle and $R^4$ is substituted aromatic monocyclic or bicyclic carbocycle or heterocycle;

provided that for compounds of formula IC, X is substituted aromatic monocyclic or bicyclic carbocycle or heterocycle and $R^4$ is H, $-OR^{11}$, $-NR^{12}R^{13}$, $-S(O)_nR^{14}$, $-C(O)R^{15}$, $-CN$, halogen or $C_1$-$C_6$ alkyl, wherein $C_1$-$C_6$ alkyl is optionally substituted from 1 to 3 times with substituents as defined below in $R^{10}$; and provided that for compounds of formula ID, X is substituted aromatic monocyclic heterocycle and $R^4$ is substituted aromatic monocyclic or bicyclic carbocycle or heterocycle;

$R^7$ and $R^8$ are each independently selected from the group consisting of H, $C_1$-$C_6$ alkyl, $C_2$-$C_6$ alkenyl, $C_2$-$C_6$-alkynyl, $C_3$-$C_6$ cycloalkyl, and $C_4$-$C_7$ cycloalkylalkyl, each of which is optionally substituted from 1 to 3 times with substituents as defined below in $R^{10}$; or $R^2$, $R^7$, and $R^8$ are gem-dimethyl, with the proviso that only one of $R^7$ and $R^8$ is gem-dimethyl;

$R^9$ is independently selected at each occurrence from a substituent in the group consisting of halogen, $-NO_2$, $-CN$, $-OR^{11}$, $-NR^{12}R^{13}$, $-NR^{12}C(O)_2R^{13}$, $-NR^{12}C(O)NR^{12}R^{13}$, $-S(O)_nR^{14}$, $-C(O)R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$;

$R^{10}$ is independently selected at each occurrence from a substituent in the group consisting of $-CN$, halogen, $C_1$-$C_3$ alkyl, $-OR^{11}$, $-NR^{12}R^{13}$, $-S(O)_nR^{14}$, $C(O)R^{15}$, aryl, and heteroaryl, wherein each of the aryl or heteroaryl groups is optionally substituted from 1 to 4 times with substituents as defined above in $R^9$;

$R^{11}$ is selected from the group consisting of H, $C_1$-$C_4$ alkyl, $C_3$-$C_6$ cycloalkyl, $C_4$-$C_7$ cycloalkylalkyl, and $-C(O)R^{15}$, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{11}$ is selected from the group consisting of phenyl, benzyl, pyridazinyl, pyrimidinyl, pyrazinyl, other 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{12}$ and $R^{13}$ are each independently selected from the group consisting of H, $-C(O)R^{15}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$;

$R^{12}$ and $R^{13}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^9$;

$R^{12}$ and $R^{13}$ are each independently a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, $-S(O)_nR^{14}$, and $-C(O)R^{15}$, with the proviso that only one of $R^{12}$ and $R^{13}$ is a bridged bicyclic ring;

$R^{12}$ and $R^{13}$ are taken together with the nitrogen to which they are attached to form a saturated or partially saturated monocyclic or bicyclic heterocycle selected from the group consisting of piperidine, pyrrolidine, morpholine, thiomorpholine, [1,2]oxazinane, isoxazolidine, 2-oxopiperidine, 2-oxopyrrolidine, 3-oxomorpholine, 3-oxothiomorpholine, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, and is optionally substituted from 1 to 3 times with a substituent selected independently at each occurrence thereof from the group consisting of halogen, cyano, $-OR^{11}$, $-NR^{12}R^{13}$, $-S(O)_nR^{14}$, $-C(O)R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, $-OR^{11}$, $-NR^{12}R^{13}$, $-S(O)_nR^{14}$, $-C(O)R^{15}$, and $C_1$-$C_4$ alkyl, or on the additional nitrogen atom from 1 to 3 times with a substituent selected independently at each occurrence thereof from the group consisting of $S(O)_nR^{14}$, $-C(O)R^{15}$, and $C_1$-$C_4$ alkyl, wherein each of $C_1$-$C_4$ alkyl is optionally substituted from 1 to 3 times with substituents as defined above in $R^{10}$;

$R^{12}$ and $R^{13}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^9$; or when $R^4$ is $-NR^{12}R^{13}$ or $-C(O)NR^{12}R^{13}$, either $R^{12}$ or $R^{13}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{15}$, and —S(O)$_n R^{14}$, or either $R^{12}$ or $R^{13}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —C(O)$R^{15}$, and —S(O)$_n R^{14}$;

$R^{14}$ is selected from the group consisting of H, —N$R^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{14}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

$R^{15}$ is selected from the group consisting of H, —OR, —N$R^{12}R^{13}$, $C_1$-$C_4$ alkyl, $C_3$-$C_6$ cycloalkyl, and $C_4$-$C_7$ cycloalkylalkyl, wherein each of $C_1$-$C_6$ alkyl, $C_3$-$C_6$ cycloalkyl, and $C_4$-$C_7$ cycloalkylalkyl is optionally substituted from 1 to 3 times with substituents as defined above in $R^{10}$; or $R^{15}$ is selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined above in $R^9$;

n is 0, 1 or 2;

with the following proviso that when $R^1$ is n-propyl, X cannot be 3-(trifluoromethyl)phenyl;

or an oxide of, or a pharmaceutically acceptable salt thereof.

2. The compound according to claim 1, wherein X is substituted phenyl and $R^4$ is substituted aromatic monocyclic or bicyclic carbocycle or heterocycle.

3. The compound according to claim 1, wherein X is substituted aromatic bicyclic carbocycle or heterocycle and $R^4$ is substituted aromatic monocyclic or bicyclic carbocycle or heterocycle.

4. The compound according to claim 1, wherein X is substituted aromatic monocyclic or bicyclic carbocycle or heterocycle and $R^4$ is H, —O$R^{11}$, —N$R^{12}R^{13}$, —S(O)$_n R^{14}$, —C(O)$R^{15}$, —CN, halogen, or $C_1$-$C_6$ alkyl, wherein $C_1$-$C_6$ alkyl is optionally substituted from 1 to 3 times with substituents as defined in $R^{10}$.

5. The compound according to claim 1, wherein X is substituted aromatic monocyclic heterocycle and $R^4$ is substituted aromatic monocyclic or bicyclic carbocycle or heterocycle.

6. The compound according to claim 1, wherein:

X is phenyl, substituted from 1 to 4 times with substituents as defined in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where $C_1$-$C_4$ alkyl is optionally substituted from 1 to 3 times with substituents as defined in $R^{10}$; and $R^8$ is H, gem-dimethyl, or $C_1$-$C_4$ alkyl, where $C_1$-$C_4$ alkyl is optionally substituted from 1 to 3 times with substituents as defined in $R^{10}$.

7. The compound according to claim 6, wherein $R^4$ is H, halogen, —OR, —N$R^{12}R^{13}$, —S(O)$_n R^{14}$, —CN, —C(O)$R^{15}$, or $C_1$-$C_6$ alkyl, where $C_1$-$C_6$ alkyl is optionally substituted from 1 to 3 times with substituents as defined in $R^{10}$.

8. The compound according to claim 6, wherein $R^4$ is phenyl, pyridyl, 2-oxo-pyridin-1(2H)-yl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, substituted from 1 to 4 times with substituents as defined in $R^9$.

9. The compound according to claim 1, wherein:

X represents a 5- or 6-membered aromatic monocyclic heterocycle selected from the group consisting of pyridyl, 2-oxo-pyridin-1(2H)-yl, pyrimidinyl, pyridazinyl, pyrazinyl, triazinyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, substituted from 1 to 4 times with substituents as defined in $R^9$;

$R^1$ is H, methyl, ethyl, or isopropyl;

$R^2$ is H, methyl, or gem-dimethyl;

$R^3$ is H, methyl, hydroxyl, methoxy, fluoro, chloro, cyano, trifluoromethyl, or trifluoromethoxy;

$R^5$ is H, methyl, hydroxyl, methoxy, fluoro, chloro, cyano, trifluoromethyl, or trifluoromethoxy;

$R^6$ is H, methyl, hydroxyl, methoxy, fluoro, chloro, cyano, trifluoromethyl, or trifluoromethoxy;

$R^7$ is H, gem-dimethyl, or $C_1$-$C_4$ alkyl, where $C_1$-$C_4$ alkyl is optionally substituted from 1 to 3 times with substituents as defined in $R^{10}$; and $R^8$ is H, gem-dimethyl, or $C_1$-$C_4$ alkyl, where $C_1$-$C_4$ alkyl is optionally substituted from 1 to 3 times with substituents as defined in $R^{10}$.

10. The compound according to claim 9, wherein $R^4$ is H, halogen, —O$R^{11}$, —N$R^{12}R^{13}$, —S(O)$_n R^{14}$, —CN, —C(O)

$R^{15}$, or $C_1$-$C_6$ alkyl, where $C_1$-$C_6$ alkyl is optionally substituted from 1 to 3 times with substituents as defined in $R^{10}$.

11. The compound according to claim 9, wherein $R^4$ is phenyl, pyridyl, 2-oxo-pyridin-1(2H)-yl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, substituted from 1 to 4 times with substituents as defined in $R^9$.

12. The compound according to claim 1, wherein:
X is a [5,5]-, [6,5]-, [6,6]-, or [6,7]-fused bicyclic carbocycle or heterocycle selected from the group consisting of indenyl, benzofuranyl, benzothiophenyl, indolyl, isoindolyl, benzooxazolyl, benzothiazolyl, benzoisothiazolyl, benzoisoxazolyl, indazolyl, benzoimidazolyl, benzotriazolyl, naphthyl, quinolinyl, isoquinolinyl, quinazolinyl, cinnolinyl, phthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, imidazo[1,2-a]pyrazinyl, 3,3-dimethyl-2-oxoindolinyl, [1,2,4]triazolo[4,3-a]pyrazinyl, and 3-oxo-[1,2,4]triazolo[4,3-a]pyridin-2(3H)-yl, substituted from 1 to 4 times with substituents as defined in $R^9$;
$R^1$ is H, methyl, ethyl, or isopropyl;
$R^2$ is H, methyl, or gem-dimethyl;
$R^3$ is H, methyl, hydroxyl, methoxy, fluoro, chloro, cyano, trifluoromethyl, or trifluoromethoxy;
$R^5$ is H, methyl, hydroxyl, methoxy, fluoro, chloro, cyano, trifluoromethyl, or trifluoromethoxy;
$R^6$ is H, methyl, hydroxyl, methoxy, fluoro, chloro, cyano, trifluoromethyl, or trifluoromethoxy;
$R^7$ is H, gem-dimethyl, or $C_1$-$C_4$ alkyl, where $C_1$-$C_4$ alkyl is optionally substituted from 1 to 3 times with substituents as defined in $R^{10}$; and
$R^8$ is H, gem-dimethyl, or $C_1$-$C_4$ alkyl, where $C_1$-$C_4$ alkyl is optionally substituted from 1 to 3 times with substituents as defined in $R^{10}$.

13. The compound according to claim 12, wherein $R^4$ is H, halogen, —$OR^{11}$, —$NR^{12}R^{13}$, —$S(O)_nR^{14}$, —CN, —C(O)$R^{15}$, or $C_1$-$C_6$ alkyl, where $C_1$-$C_6$ alkyl is optionally substituted from 1 to 3 times with substituents as defined in $R^{10}$.

14. The compound according to claim 12, wherein $R^4$ is phenyl, pyridyl, 2-oxo-pyridin-1(2H)-yl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indenyl, indolyl, isoindolyl, benzofuranyl, benzothiophenyl, indolinyl, indazolyl, benzimidazolyl, benzooxazolyl, benzothiazolyl, benzoisoxazolyl, benzoisothiazolyl, benzotriazolyl, naphthyl, quinolinyl, isoquinolinyl, quinazolinyl, cinnolinyl, pthalazinyl, quinoxalinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 3,3-dimethyl-2-oxoindolinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, substituted from 1 to 4 times with substituents as defined in $R^9$.

15. The compound according to claim 1, wherein:
X is a 5- or 6-membered aromatic monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, substituted from 1 to 4 times with substituents as defined in $R^9$;
$R^1$ is H, methyl, ethyl, or isopropyl;
$R^2$ is H, methyl, or gem-dimethyl;
$R^4$ is H, methyl, hydroxyl, methoxy, fluoro, chloro, cyano, trifluoromethyl, or trifluoromethoxy;
$R^3$, $R^5$, and $R^6$ are each independently selected from the group consisting of H, halogen, —$OR^{11}$, —$NR^{12}R^{13}$, $S(O)_nR^{14}$, —CN, —C(O)$R^{15}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{10}$; or
$R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined in $R^9$, with the proviso that only one of $R^3$, $R^5$, and $R^6$ is 5- or 6-membered monocyclic carbocycle or heterocycle or a [5,5]-, [6,5]-, [6,6]-, or [6,7]-fused bicyclic carbocycle or heterocycle;
$R^7$ is H, gem-dimethyl, or $C_1$-$C_4$ alkyl, where $C_1$-$C_4$ alkyl is optionally substituted from 1 to 3 times with substituents as defined in $R^{10}$; and
$R^8$ is H, gem-dimethyl, or $C_1$-$C_4$ alkyl, where $C_1$-$C_4$ alkyl is optionally substituted from 1 to 3 times with substituents as defined in $R^{10}$.

16. The compound according to claim 1, wherein:
X is phenyl, pyridinyl, naphthyl, benzo[b]thiophenyl, or benzofuranyl, substituted with from 1 to 3 substituents selected independently from the group consisting of fluoro, chloro, bromo, methoxy, cyano, trifluoromethyl, difluoromethoxy, carbamoyl, $C_1$-$C_3$ alkyl-substituted carbamoyl, trifluoromethoxy, acetamido, methanesulfonyl, and substituted $C_1$-$C_3$ alkyl;

$R^1$ is H, methyl, ethyl, or isopropyl;

$R^2$ is H;

$R^3$ is H or fluoro;

$R^4$ is H, methoxy, fluoro, chloro, bromo, cyano, trifluoromethyl, acetyl, morpholino, piperazinyl, 4-acetylpiperazin-1-yl, 4-(ethylsulfonyl)piperazin-1-yl, 2-cyanophenyl, 3-cyanophenyl, 4-cyanophenyl, 2-(methanesulfonyl)phenyl, 3-(methanesulfonyl)phenyl, 4-(methanesulfonyl)phenyl, 1H-pyrazol-1-yl, 1H-pyrazol-4-yl, oxazol-2-yl, thiazol-2-yl, 1,3,4-oxadiazol-2-yl, 1,3,4-thiadiazol-2-yl, 1,2,4-thiadiazol-3-yl, 1,2,4-thiadiazol-5-yl, 1H-1,2,4-triazol-1-yl, pyridin-2-yl, pyridin-3-yl, pyridin-4-yl, 6-aminopyridin-2-yl, pyridazin-3-yl, 6-methylpyridazin-3-yl, 6-(hydroxymethyl)pyridazin-3-yl, 6-(trifluoromethyl)pyridazin-3-yl, 6-(difluoromethyl)pyridazin-3-yl, 6-(difluoromethoxy)pyridazin-3-yl, 6-aminopyridazin-3-yl, pyrimidin-2-yl, pyrimidin-2-ylamino, pyrimidin-5-yl, pyrazin-2-yl, 2-oxopyridin-1(2H)-yl, 3-oxo-[1,2,4]triazolo[4,3-a]pyridin-2(3H)-yl, [1,2,4]triazolo[1,5-a]pyridin-6-yl, or [1,2,4]triazolo[4,3-a]pyridin-6-yl;

$R^5$ is H or fluoro;

$R^6$ is H or fluoro;

$R^7$ is H; and $R^8$ is H.

17. The compound according to claim 1, wherein $R^9$ is independently selected at each occurrence from a substituent in the group consisting of halogen, —CN, —OR$^{11}$, —NR$^{12}$R$^{13}$, —NR$^{12}$C(O)$_2$R$^{13}$, —NR$^{12}$C(O)NR$^{12}$R$^{13}$, —S(O)$_n$R$^{14}$, —C(O)R$^5$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined in $R^{10}$.

18. The compound according to claim 9, wherein X represents a 5- or 6-membered aromatic monocyclic heterocycle selected from the group consisting of 2-oxo-pyridin-1(2H)-yl, pyrimidinyl, pyridazinyl, pyrazinyl, triazinyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, substituted from 1 to 4 times with substituents as defined in $R^9$.

19. A compound selected from the group consisting of:
1-(1-fluoronaphthalen-2-yl)-4-methyl-7-(pyridazin-3-yl)-2,3,4,5-tetrahydro-1H-benzo[e][1,4]diazepine;
4-methyl-1-(4-(methylsulfonyl)phenyl)-7-(pyridazin-3-yl)-2,3,4,5-tetrahydro-1H-benzo[e][1,4]diazepine;
1-(3,5-difluorophenyl)-4-methyl-7-(pyridazin-3-yl)-2,3,4,5-tetrahydro-1H-benzo[e][1,4]diazepine;
1-(2,4-difluorophenyl)-4-methyl-7-(pyridazin-3-yl)-2,3,4,5-tetrahydro-1H-benzo[e][1,4]diazepine;
4-methyl-7-(pyridazin-3-yl)-1-(3-(trifluoromethyl)phenyl)-2,3,4,5-tetrahydro-1H-benzo[e][1,4]diazepine;
1-(5-fluoronaphthalen-2-yl)-4-methyl-7-(pyridazin-3-yl)-2,3,4,5-tetrahydro-1H-benzo[e][1,4]diazepine;
1-(4-fluoronaphthalen-2-yl)-4-methyl-7-(pyridazin-3-yl)-2,3,4,5-tetrahydro-1H-benzo[e][1,4]diazepine;
3-(4-methyl-7-(pyridazin-3-yl)-2,3,4,5-tetrahydro-1H-benzo[e][1,4]diazepin-1-yl)benzonitrile;
1-(benzo[d][1,3]dioxol-5-yl)-4-methyl-7-(pyridazin-3-yl)-2,3,4,5-tetrahydro-1H-benzo[e][1,4]diazepine;
4-methyl-1-(naphthalen-1-yl)-7-(pyridazin-3-yl)-2,3,4,5-tetrahydro-1H-benzo[e][1,4]diazepine;
4-methyl-1-phenyl-2,3,4,5-tetrahydro-1H-benzo[e][1,4]diazepine;
1-(3,4-difluorophenyl)-4-methyl-7-(pyridazin-3-yl)-2,3,4,5-tetrahydro-1H-benzo[e][1,4]diazepine;
1-(3-fluorophenyl)-4-methyl-7-(pyridazin-3-yl)-2,3,4,5-tetrahydro-1H-benzo[e][1,4]diazepine;
4-methyl-1-(naphthalen-2-yl)-7-(pyridazin-3-yl)-2,3,4,5-tetrahydro-1H-benzo[e][1,4]diazepine;
1-(3,4-dichlorophenyl)-4-methyl-7-(pyridazin-3-yl)-2,3,4,5-tetrahydro-1H-benzo[e][1,4]diazepine;
1-(2-fluorophenyl)-4-methyl-7-(pyridazin-3-yl)-2,3,4,5-tetrahydro-1H-benzo[e][1,4]diazepine;
1-(3-chlorophenyl)-4-methyl-7-(pyridazin-3-yl)-2,3,4,5-tetrahydro-1H-benzo[e][1,4]diazepine;
4-methyl-1-phenyl-7-(pyridazin-3-yl)-2,3,4,5-tetrahydro-1H-benzo[e][1,4]diazepine;
1-(1-(4-chlorophenyl)-4-methyl-2,3,4,5-tetrahydro-1H-benzo[e][1,4]diazepin-7-yl)pyridin-2(1H)-one;
1-(4-chlorophenyl)-4-methyl-7-(pyridazin-3-yl)-2,3,4,5-tetrahydro-1H-benzo[e][1,4]diazepine;
1-(4-fluorophenyl)-4-methyl-7-(pyridazin-3-yl)-2,3,4,5-tetrahydro-1H-benzo[e][1,4]diazepine;
4-methyl-7-(6-methylpyridazin-3-yl)-1-phenyl-2,3,4,5-tetrahydro-1H-benzo[e][1,4]diazepine;
1-(4-fluorophenyl)-4-methyl-7-(6-(trifluoromethyl)pyridazin-3-yl)-2,3,4,5-tetrahydro-1H-benzo[e][1,4]diazepine;
1-(4-methyl-1-(naphthalen-2-yl)-2,3,4,5-tetrahydro-1H-benzo[e][1,4]diazepin-7-yl)pyridin-2(1H)one;
7-(4-(ethylsulfonyl)piperazin-1-yl)-4-methyl-1-(naphthalen-2-yl)-2,3,4,5-tetrahydro-1H-benzo[e][1,4]diazepine;
4-methyl-1-(naphthalen-2-yl)-7-(pyridin-3-yl)-2,3,4,5-tetrahydro-1H-benzo[e][1,4]diazepine;
4-methyl-1-(naphthalen-2-yl)-N-(pyrimidin-2-yl)-2,3,4,5-tetrahydro-1H-benzo[e][1,4]diazepin-7-amine;
4-methyl-1-(naphthalen-2-yl)-7-(pyrazin-2-yl)-2,3,4,5-tetrahydro-1H-benzo[e][1,4]diazepine;
4-methyl-7-(4-(methanesulfonyl)phenyl)-1-(naphthalen-2-yl)-2,3,4,5-tetrahydro-1H-benzo[e][1,4]diazepine;
4-methyl-1-(naphthalen-2-yl)-7-(1H-pyrazol-1-yl)-2,3,4,5-tetrahydro-1H-benzo[e][1,4]diazepine;
4-methyl-7-(6-methylpyridazin-3-yl)-1-(naphthalen-2-yl)-2,3,4,5-tetrahydro-1H-benzo[e][1,4]diazepine;
7-([1,2,4]triazolo[1,5-a]pyridin-6-yl)-4-methyl-1-(naphthalen-2-yl)-2,3,4,5-tetrahydro-1H-benzo[e][1,4]diazepine;
7-([1,2,4]triazolo[4,3-a]pyridin-6-yl)-4-methyl-1-(naphthalen-2-yl)-2,3,4,5-tetrahydro-1H-benzo[e][1,4]diazepine;
4-methyl-1-(naphthalen-2-yl)-7-(pyrimidin-5-yl)-2,3,4,5-tetrahydro-1H-benzo[e][1,4]diazepine;
4-methyl-1-(naphthalen-2-yl)-7-(pyrimidin-2-yl)-2,3,4,5-tetrahydro-1H-benzo[e][1,4]diazepine;
1-(4-chlorophenyl)-4-methyl-7-(pyrazin-2-yl)-2,3,4,5-tetrahydro-1H-benzo[e][1,4]diazepine;
1-(4-chlorophenyl)-4-methyl-7-(4-(methylsulfonyl)phenyl)-2,3,4,5-tetrahydro-1H-benzo[e][1,4]diazepine;
1-(4-chlorophenyl)-4-methyl-7-(pyrimidin-5-yl)-2,3,4,5-tetrahydro-1H-benzo[e][1,4]diazepine;
1-(4-chlorophenyl)-4-methyl-7-(pyrimidin-2-yl)-2,3,4,5-tetrahydro-1H-benzo[e][1,4]diazepine;
4-(1-(4-chlorophenyl)-4-methyl-2,3,4,5-tetrahydro-1H-benzo[e][1,4]diazepin-7-yl)benzamide;
7-([1,2,4]triazolo[1,5-a]pyridin-6-yl)-1-(4-chlorophenyl)-4-methyl-2,3,4,5-tetrahydro-1H-benzo[e][1,4]diazepine;

7-([1,2,4]triazolo[4,3-a]pyridin-6-yl)-1-(4-chlorophenyl)-4-methyl-2,3,4,5-tetrahydro-1H-benzo[e][1,4]diazepine; and 6-(1-(4-chlorophenyl)-4-methyl-2,3,4,5-tetrahydro-1H-benzo[e][1,4]diazepin-7-yl)pyridazin-3-amine.

20. The compound according to claim 19 selected from the group consisting of:

1-(benzo[d][1,3]dioxol-5-yl)-4-methyl-7-(pyridazin-3-yl)-2,3,4,5-tetrahydro-1H-benzo[e][1,4]diazepine;

4-methyl-1-(naphthalen-1-yl)-7-(pyridazin-3-yl)-2,3,4,5-tetrahydro-1H-benzo[e][1,4]diazepine;

4-methyl-1-phenyl-2,3,4,5-tetrahydro-1H-benzo[e][1,4]diazepine;

4-methyl-1-(naphthalen-2-yl)-7-(pyridazin-3-yl)-2,3,4,5-tetrahydro-1H-benzo[e][1,4]diazepine;

4-methyl-1-phenyl-7-(pyridazin-3-yl)-2,3,4,5-tetrahydro-1H-benzo[e][1,4]diazepine;

4-methyl-7-(6-methylpyridazin-3-yl)-1-phenyl-2,3,4,5-tetrahydro-1H-benzo[e][1,4]diazepine;

1-(4-methyl-1-(naphthalen-2-yl)-2,3,4,5-tetrahydro-1H-benzo[e][1,4]diazepin-7-yl)pyridin-2(1H)one;

7-(4-(ethylsulfonyl)piperazin-1-yl)-4-methyl-1-(naphthalen-2-yl)-2,3,4,5-tetrahydro-1H-benzo[e][1,4]diazepine;

4-methyl-1-(naphthalen-2-yl)-7-(pyridin-3-yl)-2,3,4,5-tetrahydro-1H-benzo[e][1,4]diazepine;

4-methyl-1-(naphthalen-2-yl)-N-(pyrimidin-2-yl)-2,3,4,5-tetrahydro-1H-benzo[e][1,4]diazepin-7-amine;

4-methyl-1-(naphthalen-2-yl)-7-(pyrazin-2-yl)-2,3,4,5-tetrahydro-1H-benzo[e][1,4]diazepine;

4-methyl-7-(4-(methanesulfonyl)phenyl)-1-(naphthalen-2-yl)-2,3,4,5-tetrahydro-1H-benzo[e][1,4]diazepine;

4-methyl-1-(naphthalen-2-yl)-7-(1H-pyrazol-1-yl)-2,3,4,5-tetrahydro-1H-benzo[e][1,4]diazepine;

4-methyl-7-(6-methylpyridazin-3-yl)-1-(naphthalen-2-yl)-2,3,4,5-tetrahydro-1H-benzo[e][1,4]diazepine;

7-([1,2,4]triazolo[1,5-a]pyridin-6-yl)-4-methyl-1-(naphthalen-2-yl)-2,3,4,5-tetrahydro-1H-benzo[e][1,4]diazepine;

7-([1,2,4]triazolo[4,3-a]pyridin-6-yl)-4-methyl-1-(naphthalen-2-yl)-2,3,4,5-tetrahydro-1H-benzo[e][1,4]diazepine;

4-methyl-1-(naphthalen-2-yl)-7-(pyrimidin-5-yl)-2,3,4,5-tetrahydro-1H-benzo[e][1,4]diazepine; and 4-methyl-1-(naphthalen-2-yl)-7-(pyrimidin-2-yl)-2,3,4,5-tetrahydro-1H-benzo[e][1,4]diazepine.

21. A pharmaceutical composition comprising a pharmaceutically acceptable carrier and a therapeutically effective amount of the compound according to claim 1.

\* \* \* \* \*